US012771925B2

(12) United States Patent
Mikawa et al.

(10) Patent No.: US 12,771,925 B2
(45) Date of Patent: Oct. 20, 2026

(54) IMAGING APPARATUS, CONTROL METHOD, AND STORAGE MEDIUM

(71) Applicant: CANON KABUSHIKI KAISHA, Tokyo (JP)

(72) Inventors: Chiaki Mikawa, Kanagawa (JP); Sho Ichikawa, Kanagawa (JP); Genki Cho, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 511 days.

(21) Appl. No.: 18/453,124

(22) Filed: Aug. 21, 2023

(65) Prior Publication Data

US 2024/0007734 A1 Jan. 4, 2024

Related U.S. Application Data

(63) Continuation of application No. PCT/JP2022/004173, filed on Feb. 3, 2022.

(30) Foreign Application Priority Data

Feb. 24, 2021 (JP) ................................ 2021-027613
Dec. 16, 2021 (JP) ................................ 2021-204385

(51) Int. Cl.
*H04N 23/62* (2023.01)
*A61B 5/00* (2006.01)
(Continued)

(52) U.S. Cl.
CPC ........... *H04N 23/62* (2023.01); *A61B 5/0013* (2013.01); *A61B 5/0077* (2013.01); *A61B 5/445* (2013.01);
(Continued)

(58) Field of Classification Search
CPC ...... H04N 23/62; H04N 7/185; H04N 23/611; H04N 23/635; H04N 23/64; H04N 23/695;
(Continued)

(56) References Cited

U.S. PATENT DOCUMENTS

2014/0049652 A1* 2/2014 Moon .................... H04N 23/64 348/207.1
2015/0078527 A1* 3/2015 Iwamoto ............. A61B 6/4283 378/91
(Continued)

FOREIGN PATENT DOCUMENTS

CN 107773210 A 3/2018
CN 109938698 A 6/2019
(Continued)

*Primary Examiner* — Stephen P Coleman
(74) *Attorney, Agent, or Firm* — Canon U.S.A., Inc. IP Division

(57) ABSTRACT

An imaging apparatus, including an imaging unit configured to capture an image for an examination, and a communication unit configured to communicate with a predetermined system, includes a selection unit configured to select an examination purpose, an acquisition unit configured to acquire image capturing control information corresponding to the selected examination purpose from the system via the communication unit, and a control unit configured to set at least one of a setting value of an image capturing condition, display content to be displayed on a display unit together with an image to be captured by the imaging unit, and an item of information to be associated with an image captured by the imaging unit based on the image capturing control information acquired in accordance with the examination purpose.

37 Claims, 35 Drawing Sheets

(51) Int. Cl.

| | |
|---|---|
| ***G16H 30/20*** | (2018.01) |
| ***H04N 7/18*** | (2006.01) |
| ***H04N 23/60*** | (2023.01) |
| ***H04N 23/611*** | (2023.01) |
| ***H04N 23/63*** | (2023.01) |
| ***H04N 23/695*** | (2023.01) |

(52) U.S. Cl.

CPC ........... *A61B 5/7435* (2013.01); *G16H 30/20* (2018.01); *H04N 7/185* (2013.01); *H04N 23/611* (2023.01); *H04N 23/635* (2023.01); *H04N 23/64* (2023.01); *H04N 23/695* (2023.01)

(58) Field of Classification Search

CPC .... H04N 23/661; H04N 23/72; A61B 5/0013; A61B 5/0077; A61B 5/445; A61B 5/7435; A61B 5/742; A61B 5/7475; A61B 5/7485; A61B 5/4547; A61B 5/743; G16H 30/20; G03B 2205/0007; G03B 2205/0046; G03B 3/00; G03B 5/00; G03B 15/14

USPC .......................................................... 382/128

See application file for complete search history.

(56) References Cited

U.S. PATENT DOCUMENTS

| | | | | |
|---|---|---|---|---|
| 2015/0134361 | A1* | 5/2015 | Molenda | G16H 15/00 705/3 |
| 2015/0272703 | A1* | 10/2015 | Arima | A61B 6/461 378/62 |
| 2017/0061609 | A1 | 3/2017 | Son | |
| 2018/0146911 | A1 | 5/2018 | Teicher | |
| 2018/0263583 | A1 | 9/2018 | Rintamäki | |
| 2018/0344160 | A1 | 12/2018 | Sagalovich | |
| 2019/0038135 | A1 | 2/2019 | Lee | |
| 2020/0169762 | A1* | 5/2020 | Goluguri | H04N 21/47202 |
| 2020/0193601 | A1* | 6/2020 | Sugimoto | G06F 3/0488 |
| 2020/0261016 | A1* | 8/2020 | Baker | G16H 30/40 |
| 2020/0311920 | A1 | 10/2020 | Gunji | |

FOREIGN PATENT DOCUMENTS

| | | | |
|---|---|---|---|
| JP | 2008289706 | A | 12/2008 |
| JP | 2018175848 | A | 11/2018 |
| JP | 2020160853 | A | 10/2020 |
| JP | 2021028808 | A | 2/2021 |
| WO | 2019/134760 | A1 | 7/2019 |

* cited by examiner

FIG.5A

| 501 | 502 | 503 | 504 | 505 | 506 | 507 | 508 | 509 | 510 |
|---|---|---|---|---|---|---|---|---|---|
| EXAMINATION PURPOSE | IMAGE CAPTURING CONDITION | REGION CANDIDATES | ASSISTING GRAPHIC | CONFIRMATION CONDITION | WHETHER TO DISPLAY INFERENCE RESULT | EVALUATION ITEM | EVALUATION VALUE | DETERMINATION BASED ON MULTIPLE IMAGES | WHETHER IMAGE CAPTURING OF MULTIPLE REGIONS IS REQUIRED |
| PRESSURE SORE | FOCUS POSITION: CENTER<br>ZOOM POSITION: TELE<br>EXPOSURE: 0<br>ISO: 400 OR LESS AUTO<br>Tv: 1/100 OR LESS AUTO<br>Av: f/11<br>WB: FLUORESCENT<br>COLOR ADJUSTMENT: TRUE COLOR<br>ELECTRONIC FLASH: OFF | HEAD, RIGHT HAND, LEFT HAND, RIGHT ARM, LEFT ARM, BACK, LOWER BACK, RIGHT LEG, LEFT LEG, RIGHT FOOT, LEFT FOOT | AFFECTED PART OUTLINE OF SELECTED REGION IN LAST IMAGE CAPTURING | IN-FOCUS POSITION: CENTER<br>SUBJECT DISTANCE: 20-100 cm<br>FACING SUBJECT<br>CUT-OFF REGION IN WHICH PREDETERMINED COLOR IS DISTRIBUTED: N/A<br>BRIGHTNESS/EDGE EVALUATION VALUE: WITHIN PREDETERMINED ALUE RANGE | DISPLAY<br>AREA OF AFFECTED PART, PRESSURE SORE PORTION, NECROTIC PORTION, INFLAMED/INFECTED PORTION, GRANULATION TISSUE PORTION, DEPTH INFORMATION | DESI<br>GN-R | [Depth]d0,d1,d2,D3,D4,D5,DU<br>[Exudate]e0,e1,e3,E6<br>[Size]s0,s3.s6.s8.s9.s12.S15<br>[Inflammation]i0,I1.I3,I9<br>[Granulation]g0,g1,g3,G4,G5,G6<br>[Necrotic tissue]n0,N3,N6<br>[Pocket]p0,P6,P9,P12,P24 | NOT EXECUTE | — |

511

FIG.5B

| | | | | | | | | | | |
|---|---|---|---|---|---|---|---|---|---|---|
| 512 | BURN INJURY | FOCUS POSITION: CENTER<br>EXPOSURE: 0<br>ISO: 100<br>Tv: 1/200<br>Av: f/11<br>WB: ELECTRONIC FLASH<br>COLOR ADJUSTMENT: TRUE COLOR<br>ELECTRONIC FLASH: ON<br><br><TOTAL BODY FLAG ON><br>ZOOM POSITION: MANUAL<br><br><TOTAL BODY FLAG OFF><br>ZOOM POSITION: TELE | <TOTAL BODY FLAG ON><br>HEAD/NECK, BODY TRUNK, UPPER EXTREMITY, LOWER EXTREMITY<br><br><TOTAL BODY FLAG OFF><br>HEAD, RIGHT HAND, LEFT HAND, RIGHT ARM, LEFT ARM, BACK, LOWER BACK, RIGHT LEG, LEFT LEG, RIGHT FOOT, LEFT FOOT | <TOTAL BODY FLAG ON><br>BODY OUTLINE OF SELECTED REGION<br><br><TOTAL BODY FLAG OFF><br>N/A | <TOTAL BODY FLAG ON><br>IN-FOCUS POSITION: CENTER<br>SUBJECT DISTANCE: 50 cm TO 5 m<br>PERCENTAGE OF OUTLINE AND SUBJECT IMAGE FALLS WITHIN PREDETERMINED VALUE RANGE<br>BRIGHTNESS/EDGE EVALUATION VALUE: WITHIN PREDETERMINED ALUE RANGE<br><br><TOTAL BODY FLAG OFF><br>IN-FOCUS POSITION: CENTER<br>SUBJECT DISTANCE: 20-100 cm<br>FACING SUBJECT<br>CUT-OFF REGION IN WHICH PREDETERMINED COLOR IS DISTRIBUTED: N/A<br>BRIGHTNESS/EDGE EVALUATION VALUE: WITHIN PREDETERMINED ALUE RANGE | DISPLAY AREA OF AFFECTED PART, BURN PORTION, BURN DEPTH | TBSA, BURN DEPTH | [BURN DEPTH] FIRST DEGREE,<br>SECOND-DEGREE SUPERFICIAL BURN,<br>SECOND-DEGREE DEEP BURN, THIRD DEGREE | EXECUTE | <TOTAL BODY FLAG ON><br>REQUIRED HEAD/NECK, BODY TRUNK, UPPER EXTREMITY, LOWER EXTREMITY |
| 513 | ASTEATOSIS CUTIS | SAME AS ABOVE | SAME AS ABOVE | SAME AS ABOVE | SAME AS ABOVE | DISPLAY AREA OF AFFECTED PART, ASTEATOSIS CUTIS PORTION, AREA OF AFFECTED PART, SKIN ROUGHNESS, SKIN REDNESS, SKIN CRACKS AND FISSURES PORTION | SRRC | [Scaling] 0,1,2,3,4<br>[Roughness] 0,1,2,3,4<br>[Redness] 0,1,2,3,4<br>[Cracksfisseres] 0,1,2,3,4 | EXECUTE | SAME AS ABOVE |

FIG.5C

| | | | | | | | | | | |
|---|---|---|---|---|---|---|---|---|---|---|
| 514 | ATOPIC DERMATITIS | SAME AS ABOVE | SAME AS ABOVE | SAME AS ABOVE | SAME AS ABOVE | DISPLAY<br>AREA OF AFFECTED PART, ERYTHEMATOUS PORTION, EROSION/ PAPULAR PORTION, SCRATCHED PORTION, LICHENIFIED PORTION | EASI | [ERYTHEMA]0,1,2,3<br>[EROSION/PAPULA]0,1,2,3<br>[SCRATCH]0,1,2,3<br>[LICHENIFICATION]0,1,2,3 | EXECUTE | SAME AS ABOVE |
| 515 | PSORA | SAME AS ABOVE | SAME AS ABOVE | SAME AS ABOVE | SAME AS ABOVE | DISPLAY<br>AREA OF AFFECTED PART, ERYTHEMATOUS PORTION, EROSION PORTION, DESQUAMATED PORTION | PASI | [ERYTHEMA]0,1,2,3,4<br>[EROSION]0,1,2,3,4<br>[DESQUAMATION]0,1,2,3,4 | EXECUTE | SAME AS ABOVE |
| 516 | HIVES | SAME AS ABOVE | SAME AS ABOVE | SAME AS ABOVE | SAME AS ABOVE | DISPLAY<br>AREA OF AFFECTED PART, WHEAL PORTION, NUMBER OF HIVES | UAS | [NUMBER OF HIVES]0,1,2,3<br>[ITCH] 0,1,2,3 | EXECUTE | SAME AS ABOVE |
| 517 | TEETH | FOCUS POSITION: TOOTH POSITION ON IMAGE CAPTURING PLANE<br>ZOOM POSITION: 1:3<br>ISO: 100<br>Tv: 1/200<br>Av: f/22<br>WB: ELECTRONIC FLASH<br>COLOR ADJUSTMENT: TRUE COLOR<br>ELECTRONIC FLASH: ON | UPPER JAW, LOWER JAW, FRONT SIDE, LEFT SIDE, RIGHT SIDE | <UPPER JAW, LOWER JAW><br>OUTLINE OF DENTAL ARCH AND VERTICAL LINE PASSING THROUGH CENTER<br><FRONT SIDE, LEFT SIDE, RIGHT SIDE><br>HORIZONTAL LINE AND VERTICAL LINE PASSING THROUGH CENTER | IN-FOCUS POSITION:<br><UPPER JAW, LOWER JAW><br>OUTLINE POSITION<br><FRONT SIDE, LEFT SIDE, RIGHT SIDE><br>CENTER<br>SUBJECT DISTANCE: PREDETERMINED VALUE RANGE<br>OUTLINE AND REGION IN WHICH PREDETERMINED COLOR IS DISTRIBUTED FALL WITHIN PREDETERMINED VALUE RANGE<br>BRIGHTNESS/EDGE EVALUATION VALUE: WITHIN PREDETERMINED VALUE RANGE | NOT DISPLAY | N/A | N/A | EXECUTE | UPPER JAW, LOWER JAW |

FIG.17A

| | 501 | 1701 | 503 | 504 | 505 | 506 | 507 | 508 | 509 | 510 |
|---|---|---|---|---|---|---|---|---|---|---|
| | EXAMINATION PURPOSE | IMAGE CAPTURING CONDITION | REGION CANDIDATES | ASSISTING GRAPHIC | CONFIRMATION CONDITION | WHETHER TO DISPLAY INFERENCE RESULT | EVALUATION ITEM | EVALUATION VALUE | DETERMINATION BASED ON MULTIPLE IMAGES | WHETHER IMAGE CAPTURING OF MULTIPLE REGIONS IS REQUIRED |
| 511 | PRESSURE SORE | FOCUS POSITION: CENTER<br>ZOOM POSITION: TELE<br>EXPOSURE: 0<br>ISO: 400 OR LESS AUTO<br>Tv: 1/100 OR LESS AUTO<br>Av: f/11<br>WB: FLUORESCENT<br>COLOR ADJUSTMENT: TRUE COLOR<br>ELECTRONIC FLASH: OFF | HEAD, RIGHT HAND, LEFT HAND, RIGHT ARM, LEFT ARM, BACK, LOWER BACK, RIGHT LEG, LEFT LEG, RIGHT FOOT, LEFT FOOT | AFFECTED PART OUTLINE OF SELECTED REGION IN LAST IMAGE CAPTURING | IN-FOCUS POSITION: CENTER<br>SUBJECT DISTANCE: 20-100 cm<br>FACING SUBJECT<br>CUT-OFF REGION IN WHICH PREDETERMINED COLOR IS DISTRIBUTED: N/A<br>BRIGHTNESS/EDGE EVALUATION VALUE: WITHIN PREDETERMINED ALUE RANGE | DISPLAY<br>AREA OF AFFECTED PART, PRESSURE SORE PORTION, NECROTIC PORTION, INFLAMED/INFECTED PORTION, GRANULATION TISSUE PORTION, DEPTH INFORMATION | DESI GN-R | [Depth]d0,d1,d2,D3,D4,D5,DU<br>[Exudate]e0,e1,e3,E6<br>[Size]s0,s3.s6.s8.s9.s12.S15<br>[Inflammation]i0,I1.I3,I9<br>[Granulation]g0,g1,g3,G4,G5,G6<br>[Necrotic tissue]n0,N3,N6<br>[Pocket]p0,P6,P9,P12,P24 | NOT EXECUTE | — |

FIG.17B

| | | | | | | | | | | |
|---|---|---|---|---|---|---|---|---|---|---|
| 512 | BURN INJURY | FOCUS POSITION: CENTER<br>EXPOSURE: 0<br>ISO: 100<br>Tv: 1/200<br>Av: f/11<br>WB: ELECTRONIC FLASH<br>COLOR ADJUSTMENT: TRUE COLOR<br>ELECTRONIC FLASH: ON<br><br><TOTAL BODY FLAG ON><br>ZOOM POSITION: MANUAL<br><br><TOTAL BODY FLAG OFF><br>ZOOM POSITION: TELE | <TOTAL BODY FLAG ON><br>HEAD/NECK, BODY TRUNK, UPPER EXTREMITY, LOWER EXTREMITY<br><br><TOTAL BODY FLAG OFF><br>HEAD, RIGHT HAND, LEFT HAND, RIGHT ARM, LEFT ARM, BACK, LOWER BACK, RIGHT LEG, LEFT LEG, RIGHT FOOT, LEFT FOOT | <TOTAL BODY FLAG ON><br>BODY OUTLINE OF SELECTED REGION<br><br><TOTAL BODY FLAG OFF><br>N/A | <TOTAL BODY FLAG ON><br>IN-FOCUS POSITION: CENTER<br>SUBJECT DISTANCE: 50 cm TO 5 m<br>PERCENTAGE OF OUTLINE AND SUBJECT IMAGE FALLS WITHIN PREDETERMINED VALUE RANGE<br>BRIGHTNESS/EDGE EVALUATION VALUE: WITHIN PREDETERMINED ALUE RANGE<br><br><TOTAL BODY FLAG OFF><br>IN-FOCUS POSITION: CENTER<br>SUBJECT DISTANCE: 20-100 cm<br>FACING SUBJECT<br>CUT-OFF REGION IN WHICH PREDETERMINED COLOR IS DISTRIBUTED: N/A<br>BRIGHTNESS/EDGE EVALUATION VALUE: WITHIN PREDETERMINED ALUE RANGE | DISPLAY AREA OF AFFECTED PART, BURN PORTION, BURN DEPTH | TBSA, BURN DEPTH | [BURN DEPTH] FIRST DEGREE, SECOND-DEGREE SUPERFICIAL BURN, SECOND-DEGREE DEEP BURN, THIRD DEGREE | EXECUTE | <TOTAL BODY FLAG ON><br>REQUIRED HEAD/NECK, BODY TRUNK, UPPER EXTREMITY, LOWER EXTREMITY |
| 513 | ASTEATOSIS CUTIS | SAME AS ABOVE EXCEPT FOR FOLLOWING CHANGE<br>ZOOM POSITION: MANUAL | SAME AS ABOVE | SAME AS ABOVE | SAME AS ABOVE | DISPLAY AREA OF AFFECTED PART, ASTEATOSIS CUTIS PORTION, AREA OF AFFECTED PART, SKIN ROUGHNESS, SKIN REDNESS, SKIN CRACKS AND FISSURES PORTION | SRRC | [Scaling] 0,1,2,3,4<br>[Roughness] 0,1,2,3,4<br>[Redness] 0,1,2,3,4<br>[Cracksfisseres] 0,1,2,3,4 | EXECUTE | SAME AS ABOVE |

FIG.17C

| | | | | | | | | | | |
|---|---|---|---|---|---|---|---|---|---|---|
| 514 | ATOPIC DERMATITIS | SAME AS ABOVE | SAME AS ABOVE | SAME AS ABOVE | SAME AS ABOVE | DISPLAY<br>AREA OF AFFECTED PART, ERYTHEMATOUS PORTION, EROSION/ PAPULAR PORTION, SCRATCHED PORTION, LICHENIFIED PORTION | EASI | [ERYTHEMA]0,1,2,3<br>[EROSION/PAPULA]0,1,2,3<br>[SCRATCH]0,1,2,3<br>[LICHENIFICATION]0,1,2,3 | EXECUTE | SAME AS ABOVE |
| 515 | PSORA | SAME AS ABOVE | SAME AS ABOVE | SAME AS ABOVE | SAME AS ABOVE | DISPLAY<br>AREA OF AFFECTED PART, ERYTHEMATOUS PORTION, EROSION PORTION, DESQUAMATED PORTION | PASI | [ERYTHEMA]0,1,2,3,4<br>[EROSION]0,1,2,3,4<br>[DESQUAMATION]0,1,2,3,4 | EXECUTE | SAME AS ABOVE |
| 516 | HIVES | SAME AS ABOVE | SAME AS ABOVE | SAME AS ABOVE | SAME AS ABOVE | DISPLAY<br>AREA OF AFFECTED PART, WHEAL PORTION, NUMBER OF HIVES | UAS | [NUMBER OF HIVES]0,1,2,3<br>[ITCH] 0,1,2,3 | EXECUTE | SAME AS ABOVE |
| 517 | TEETH | FOCUS POSITION: TOOTH POSITION ON IMAGE CAPTURING PLANE<br>ZOOM POSITION: 1:3<br>ISO: 100<br>Tv: 1/200<br>Av: f/22<br>WB: ELECTRONIC FLASH<br>COLOR ADJUSTMENT: TRUE COLOR<br>ELECTRONIC FLASH: ON | UPPER JAW, LOWER JAW, FRONT SIDE, LEFT SIDE, RIGHT SIDE | <UPPER JAW, LOWER JAW><br>VERTICAL LINE PASSING THROUGH OUTLINE AND CENTER OF DENTAL ARCH<br><FRONT SIDE, LEFT SIDE, RIGHT SIDE><br>HORIZONTAL LINE AND VERTICAL LINE PASSING THROUGH CENTER | IN-FOCUS POSITION:<br><UPPER JAW, LOWER JAW><br>OUTLINE POSITION<br><FRONT SIDE, LEFT SIDE, RIGHT SIDE><br>CENTER<br>SUBJECT DISTANCE: PREDETERMINED VALUE RANGE<br>OUTLINE AND REGION IN WHICH PREDETERMINED COLOR IS DISTRIBUTED FALL WITHIN PREDETERMINED VALUE RANGE<br>BRIGHTNESS/EDGE EVALUATION VALUE: WITHIN PREDETERMINED ALUE RANGE | NOT DISPLAY | N/A | N/A | EXECUTE | UPPER JAW, LOWER JAW |

FIG.26

| EXAMINATION PURPOSE | REGION CANDIDATES | IMAGE CAPTURING CONDITION | CONFIRMATION CONDITION |
|---|---|---|---|
| PRESSURE SORE | HEAD | FOCUS POSITION: CENTER<br>ZOOM POSITION: TELE<br>EXPOSURE: 0<br>ISO: 400 OR LESS AUTO<br>Tv: 1/100 OR LESS AUTO<br>Av: f/6<br>WB: FLUORESCENT<br>COLOR ADJUSTMENT: TRUE COLOR<br>ELECTRONIC FLASH: OFF | IN-FOCUS POSITION: CENTER<br>SUBJECT DISTANCE: 50-80 cm<br>FACING SUBJECT<br>CUT-OFF REGION IN WHICH PREDETERMINED COLOR IS DISTRIBUTED: N/A<br>BRIGHTNESS/EDGE EVALUATION VALUE: WITHIN PREDETERMINED VALUE RANGE |
| | HAND, ARM | FOCUS POSITION: CENTER<br>ZOOM POSITION: TELE<br>EXPOSURE: 0<br>ISO: 400 OR LESS AUTO<br>Tv: 1/100 OR LESS AUTO<br>Av: f/6<br>WB: FLUORESCENT<br>COLOR ADJUSTMENT: TRUE COLOR<br>ELECTRONIC FLASH: OFF | IN-FOCUS POSITION: CENTER<br>SUBJECT DISTANCE: 30-70 cm<br>FACING SUBJECT<br>CUT-OFF REGION IN WHICH PREDETERMINED COLOR IS DISTRIBUTED: N/A<br>BRIGHTNESS/EDGE EVALUATION VALUE: WITHIN PREDETERMINED VALUE RANGE |
| | BACK, LOWER BACK | FOCUS POSITION: ENTIRETY<br>ZOOM POSITION: TELE<br>EXPOSURE: 0<br>ISO: 400 OR LESS AUTO<br>Tv: 1/100 OR LESS AUTO<br>Av: f/11<br>WB: FLUORESCENT<br>COLOR ADJUSTMENT: TRUE COLOR<br>ELECTRONIC FLASH: OFF | IN-FOCUS POSITION: ENTIRETYY<br>SUBJECT DISTANCE: 80-120 cm<br>FACING SUBJECT<br>CUT-OFF REGION IN WHICH PREDETERMINED COLOR IS DISTRIBUTED: N/A<br>BRIGHTNESS/EDGE EVALUATION VALUE: WITHIN PREDETERMINED VALUE RANGE |
| | LEG, FOOT | FOCUS POSITION: ENTIRETY<br>ZOOM POSITION: TELE<br>EXPOSURE: 0<br>ISO: 3000<br>Tv: 1/50<br>Av: f/20<br>WB: FLUORESCENT<br>COLOR ADJUSTMENT: TRUE COLOR<br>ELECTRONIC FLASH: OFF | IN-FOCUS POSITION: CENTER<br>SUBJECT DISTANCE: 100-120 cm<br>FACING SUBJECT<br>CUT-OFF REGION IN WHICH PREDETERMINED COLOR IS DISTRIBUTED: N/A<br>BRIGHTNESS/EDGE EVALUATION VALUE: WITHIN PREDETERMINED VALUE RANGE |

IMAGING APPARATUS, CONTROL METHOD, AND STORAGE MEDIUM

CROSS-REFERENCE TO RELATED APPLICATIONS

This application is a Continuation of International Patent Application No. PCT/JP2022/004173, filed Feb. 3, 2022, which claims the benefit of Japanese Patent Applications No. 2021-027613, filed Feb. 24, 2021, and No. 2021-204385, filed Dec. 16, 2021, all of which are hereby incorporated by reference herein in their entirety.

BACKGROUND OF THE INVENTION

Field of the Invention

The present invention relates to an imaging apparatus that captures an image of an affected part of a patient for an examination on a medical setting or the like, for example.

Background Art

There has been a medical imaging apparatus that captures an image for assisting the diagnosis of an affected part. Patent Literature (PTL) 1 discusses a medical imaging apparatus including two light sources, namely a first light source and a second light source, that emit light in different directions, and discusses that the first light source is used in a first image capturing state in which image capturing of an affected part is performed in a normal image capturing state, and the second light source is used in a second image capturing state in which image capturing of an affected part is performed in an image capturing state different from the normal image capturing state.

CITATION LIST

Patent Literature

PTL 1: Japanese Patent Application Laid-Open No. 2018-175848

In PTL 1, a light source to be used is varied between the first image capturing state in which image capturing of an affected part is performed in the normal image capturing state and the second image capturing state in which image capturing of an affected part is performed in the image capturing state different from the normal image capturing state. Nevertheless, an operator sometimes fails to capture an image in an image capturing state suitable for a patient or a type of examination, and fails to acquire information necessary for the examination.

SUMMARY OF THE INVENTION

In view of the foregoing, the present invention is directed to providing an imaging apparatus that captures an image for an examination, and can acquire information necessary for the examination.

According to an aspect of the present invention, an imaging apparatus including an imaging unit configured to capture an image for an examination, and a communication unit configured to communicate with a predetermined system, includes a selection unit configured to select an examination purpose, an acquisition unit configured to acquire image capturing control information corresponding to the examination purpose selected by the selection unit from the system via the communication unit, and a control unit configured to set at least one of a setting value of an image capturing condition, display content to be displayed on a display unit together with an image to be captured by the imaging unit, and an item of information to be associated with an image captured by the imaging unit based on the image capturing control information acquired in accordance with the examination purpose.

Other features and advantages of the present invention will become apparent from the following description with reference to the attached drawings. In the attached drawings, the same or similar components are assigned the same reference numerals.

Further features of the present invention will become apparent from the following description of exemplary embodiments with reference to the attached drawings.

BRIEF DESCRIPTION OF THE DRAWINGS

The attached drawings, which are incorporated in and constitute a part of the specification, illustrate exemplary embodiments of the present invention and are used to explain the principles of the present invention, together with the description.

FIGS. 5A, 5B, and 5C are conceptual diagrams illustrating correspondence relationship between image capturing control information and examination purposes.

FIGS. 17A, 17B, and 17C, are conceptual diagrams illustrating correspondence relationship between image capturing control information and examination purposes.

FIG. 26 is a conceptual diagram illustrating correspondence relationship between image capturing control information and an examination purpose.

DESCRIPTION OF THE EMBODIMENTS

First Exemplary Embodiment

An imaging apparatus that captures an image of an affected part of a patient and assists diagnosis on a medical setting, in a medical system according to the present exemplary embodiment will be described. The description will be provided using, as an example, pressure sore as a single affected part to be image-captured and diagnosed.

Names, ages, genders, medical histories, and the like of patients to be managed by the medical system according to the present exemplary embodiment are pre-registered in an electronic medical chart system to be described below, and a patient management number for uniquely identifying each patient is preliminarily allocated to the patient. Then, a barcode indicating the patient management number is attached to an arm of the corresponding patient as a wristband.

In addition, in the medical system according to the present exemplary embodiment, information for controlling a change in a setting value of an image capturing condition in an imaging apparatus, screen display content (image capturing assisting graphic, etc.), and image additional information (examination evaluation item, etc.) will be described as image capturing control information. Details of the image capturing control information and details of a control method of an imaging apparatus will be described below.

In addition, the above-described image capturing condition indicates parameters (setting values) in an imaging apparatus that are to be used during image capturing. Specifically, the image capturing condition includes parameters (setting values) of a focus position, a zoom position, an ISO sensitivity, an exposure, a time value (Tv) (shutter speed), an aperture value (Av), white balance, electronic flash on/off, color adjustment processing, and edge enhancement processing.

System Configuration

Figure 1:
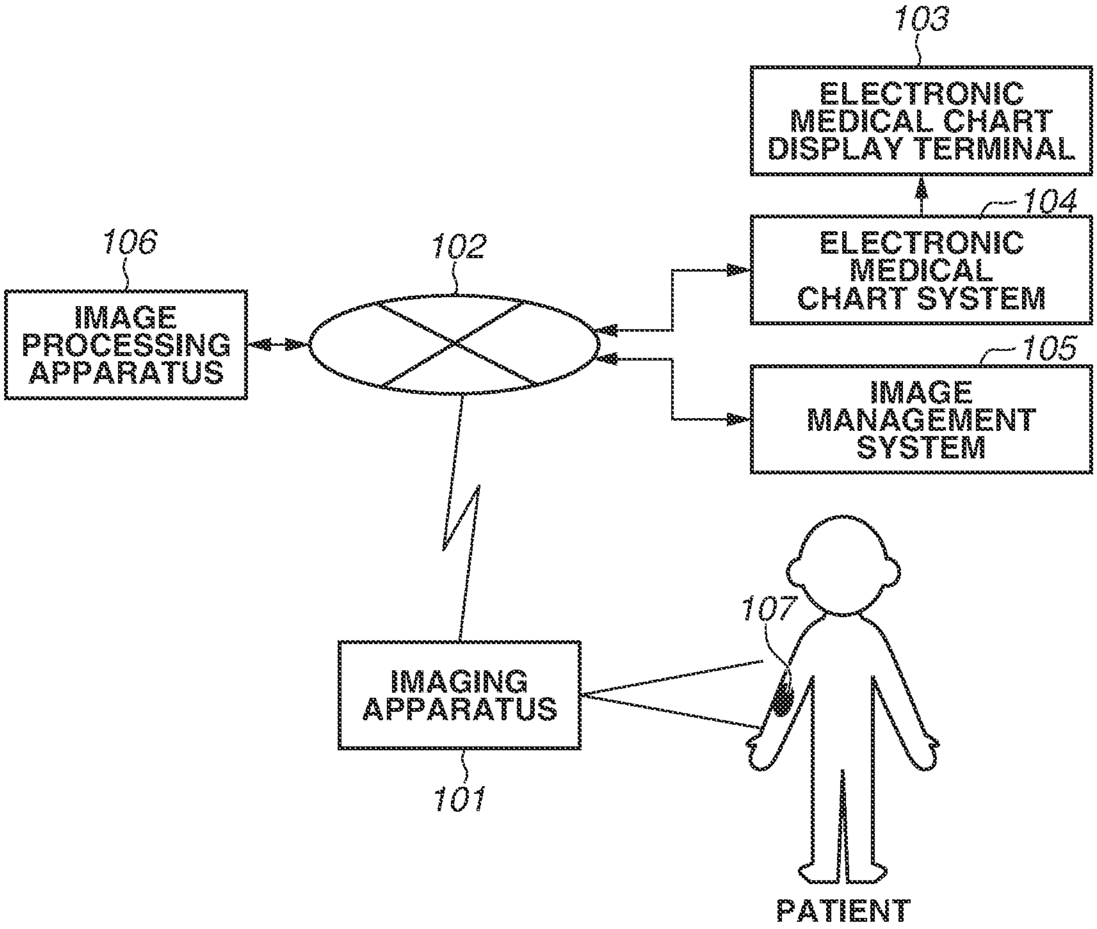
FIG. 1 is a medical system apparatus configuration diagram illustrating an apparatus configuration of a medical system.

FIG. 1 is a medical system apparatus configuration diagram illustrating an apparatus configuration of a medical system according to the present exemplary embodiment. The medical system according to the present exemplary embodiment includes an apparatus that performs the following processing.

An imaging apparatus 101 being the present invention generates visible light image data by capturing an image of an affected part 107 of a patient, which will be described below. In the following description, an image captured by the imaging apparatus 101 is described as being the visible light image data. The imaging apparatus 101 adds patient information, such as the patient management number associated with the patient, to the image data obtained by image capturing, and transmits the image data to an image processing apparatus 106 to be described below. Similarly to a commercially-available digital camera, the imaging apparatus 101 is a portable compact imaging apparatus, and includes a display device on which captured images can be checked, and an input-output device for various operations, such as selection of patient information. Simultaneously with the power being turned on by an operator, the imaging apparatus 101 connects with a network 102 to be described below, and becomes able to communicate with another apparatus in the medical system via the network 102. Then, the imaging apparatus 101 continuously keeps a communication-executable state until the power is turned off.

The image processing apparatus 106 communicates with the imaging apparatus 101, transmits an examination purpose to be described below, transmits image capturing control information, executes inference depending on the examination purpose, transmits an inference result, and acquires patient information from an electronic medical chart system 104.

Upon receiving a request from an electronic medical chart display terminal 103 to be described below, the electronic medical chart system 104 communicates with the image processing apparatus 106 and an image management system 105 to be described below, and performs electronic medical chart creation and data transmission and reception accompanying editing processing. The electronic medical chart system 104 according to the present exemplary embodiment stores, in an internal storage device, the management number of a patient in the medical system, the name, the age, the gender, the medical history, a position in a body of a past disease, and a diagnosis result. Then, in response to a patient information acquisition request from the image processing apparatus 106, the electronic medical chart system 104 can acquire a series of pieces of information regarding the patient based on the management number of the patient. Furthermore, in response to the patient information acquisition request from the image processing apparatus 106, the electronic medical chart system 104 can communicate with the image management system 105 to be described below, and can also acquire image data associated with the diagnosis of a past disease, and an image of an inference result to be described below.

The electronic medical chart display terminal 103 communicates with the electronic medical chart system 104, displays an electronic medical chart, receives entries made when the electronic medical chart is created, and performs processing of adding information to an image.

The image management system 105 receives image data obtained by image capturing executed by the imaging apparatus 101, via the image processing apparatus 106, and records, in the internal storage device, the received image data in association with a patient management number and an image capturing date and time. Then, in a case where an image data acquisition request is issued from the electronic medical chart system 104 or the image processing apparatus 106, the image management system 105 transmits image data satisfying a designated condition, to a request source.

The affected part 107 of the patient indicates a part to be diagnosed in the medical system. There are a case of diagnosing a disease state based on appearance of a symptom throughout a total body, and a case of diagnosing a disease state based on appearance of a symptom on a partial region. In the case of diagnosing a disease state based on the appearance of the symptom throughout the total body, a large area, such as the head, the body trunk, a lower extremity, or an upper extremity, is to be diagnosed.

The image processing apparatus 106, the imaging apparatus 101, the electronic medical chart system 104, and the image management system 105 communicate with each other via the network 102. In addition, the electronic medical chart display terminal 103 and the electronic medical chart system 104 perform communicate via a High-Definition Multimedia Interface (HDMI) (registered trademark) cable or the like. While a network, an HDMI (registered trademark), and a universal serial bus (USB) are used as examples of a communication means, the communication means is not limited to them.

In the medical system of the present exemplary embodiment, the imaging apparatus 101, the electronic medical chart display terminal 103, the electronic medical chart system 104, the image management system 105, and the image processing apparatus 106 are described as separate apparatuses. Nevertheless, by the electronic medical chart display terminal 103 including components of the imaging apparatus 101, for example, functions of two or more apparatuses may be implemented by one apparatus.

Imaging Apparatus

A digital still camera operating as the imaging apparatus 101 of the present exemplary embodiment will be described.

Figure 2:
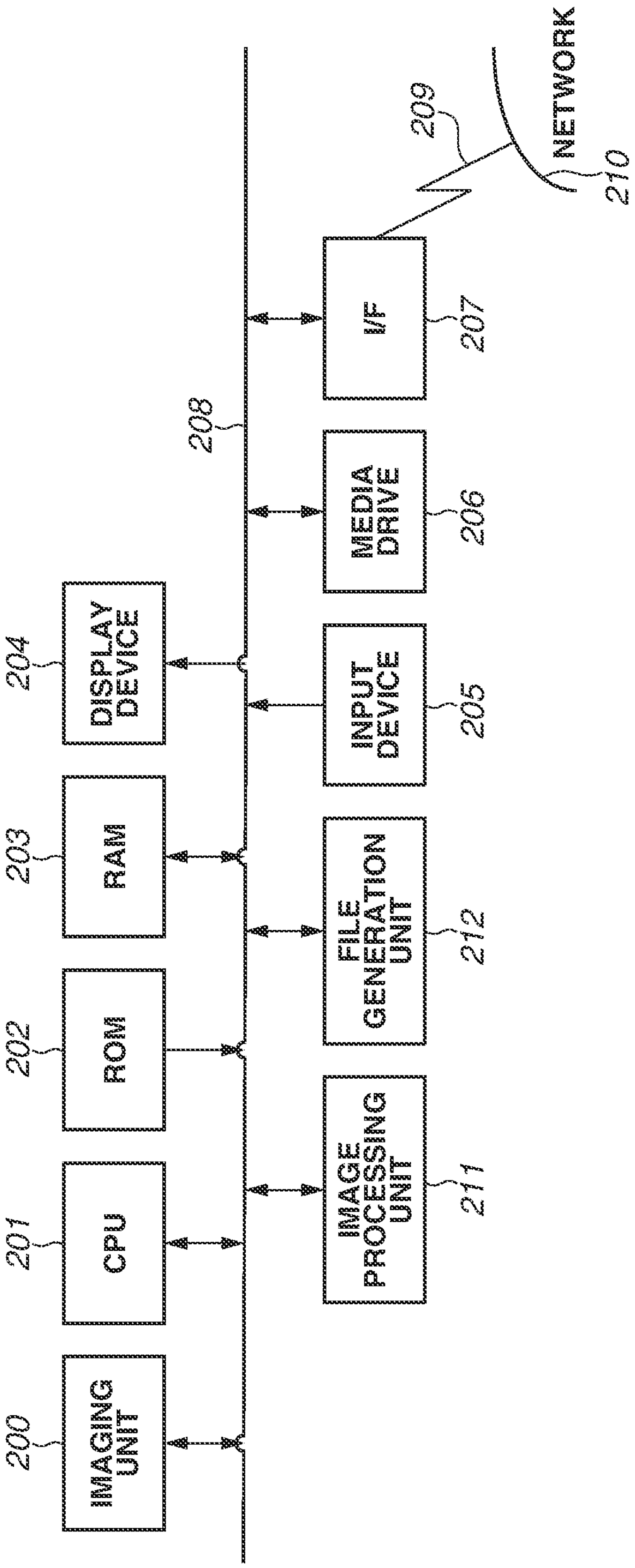
FIG. 2 is a block diagram of a digital still camera operating as an imaging apparatus.

FIG. 2 is a block diagram illustrating a digital still camera operating as an imaging apparatus according to an exemplary embodiment of the present invention. By executing a predetermined control program, the digital still camera implements image capturing processing to be described below, and functions as the imaging apparatus.

In FIG. 2, an imaging unit 200 reads an optical image using a solid-state image sensor, and generates electronic image data by performing analog-to-digital conversion. A central processing unit (CPU) 201 controls the entire digital still camera. A read-only memory (ROM) 202 stores an operation processing procedure of the CPU 201 (e.g., programs of processing to be executed when the power of the digital still camera is turned on, basic input-output processing, etc.). A random access memory (RAM) 203 functions as a main memory of the CPU 201. Various programs including a control program for implementing processing to be described below are loaded onto the RAM 203 from the ROM 202 or the like, and executed by the CPU 201. The RAM 203 provides a work area to be used when the CPU 201 executes various types of processing. A display device (display unit) 204 performs various types of display under the control of the CPU 201. For example, the display device 204 displays data stored in a storage medium. The display device 204 also displays a live view image captured by the imaging unit 200, a captured image captured by the imaging unit 200 in response to input of an image capturing instruction by an operation on a release button (shutter button), and various setting screens. An input device 205 includes a button or the like for performing various operations. For example, the input device 205 includes the release button positioned on the top of the digital still camera, and arrow keys, a setting key, and the like that are positioned in a back side portion. In addition, a touch panel and the like that are provided on the display device 204 are also included in the input device. A user (operator) can input various instructions to the digital still camera (the imaging apparatus 101) by performing user operations on the input device. To a media drive 206, a removable storage medium can be attached, so that data can be stored therein and the stored data can be read therefrom. A network interface (IF) (communication unit) 207 is connected with a computer network 210 via a wireless communication line 209. By the network interface, data is transmitted to or received from a server computer and a personal computer. A system bus 208 (including an address bus, a data bus, and a control bus) connects the above-described components. An image processing unit 211 is an image processing unit. The CPU 201 temporarily stores, in the RAM 203, image data generated by the imaging unit 200, and attribute information about the image data. Then, the CPU 201 performs a series of image processes in the image processing unit 211 as necessary in such a manner that the image data becomes image data suitable for visual characteristics of a person. A file generation unit 212 is a file generation unit. The CPU 201 converts the format of image data into a general-purpose still image format in the file generation unit. In the present exemplary embodiment, the image data is converted into Joint Photographic Experts Group (JPEG) image data.

A hardware configuration of the imaging apparatus 101 according to the present exemplary embodiment is the same as that of a normal digital camera, and the imaging apparatus 101 is assumed to be a compact portable digital camera (portable type imaging apparatus). Then, a control program specialized for the medical system of the present exemplary embodiment is assumed to be installed as a control program of the imaging apparatus 101 and stored in the ROM 202. Thus, by newly preparing a control program for the medical system, the imaging apparatus 101 of the present exemplary embodiment can be implemented using an existing normal imaging apparatus without preparing a new imaging apparatus for the medical system of the present exemplary embodiment.

Image Processing Apparatus

A computer operating as the image processing apparatus 106 of the present exemplary embodiment will be described.

Figure 3:
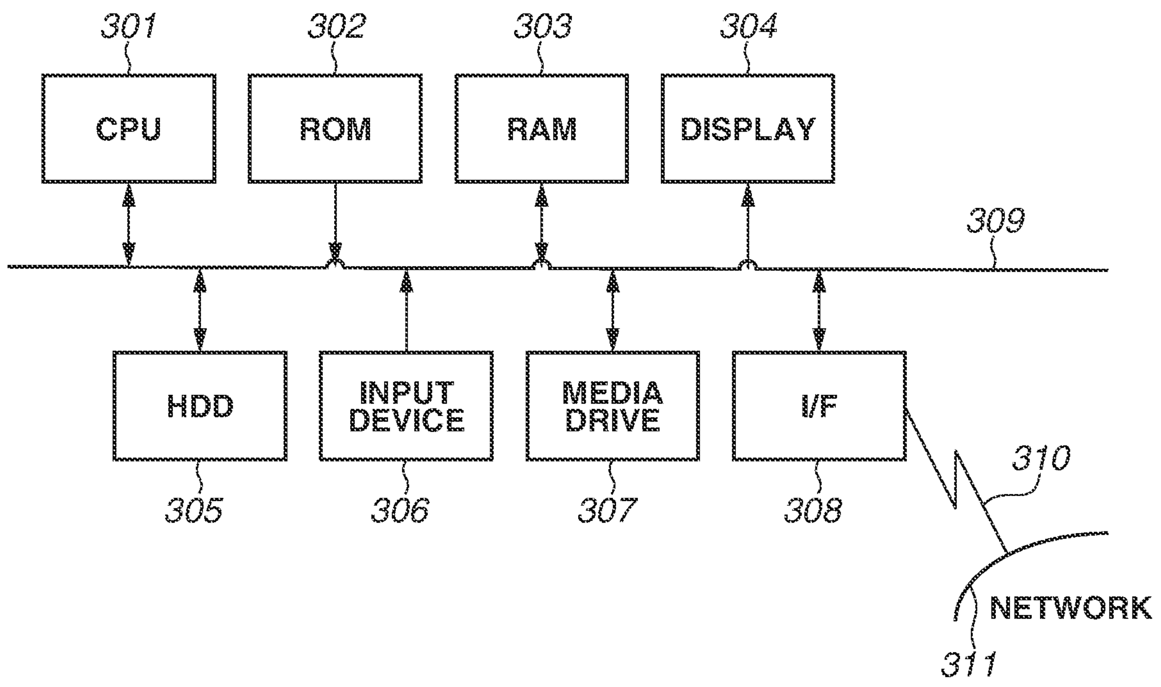
FIG. 3 is a block diagram illustrating a computer operating as an image processing apparatus.

FIG. 3 is a block diagram illustrating a computer operating as an image processing apparatus according to an exemplary embodiment of the present invention. By executing a predetermined control program, the computer performs image processing to be described below, and functions as the image processing apparatus.

In FIG. 3, a CPU 301 controls the image processing apparatus. A ROM 302 stores an operation processing procedure of the CPU 301 (e.g., programs of computer start-up processing, basic input-output processing, etc.). A RAM 303 functions as a main memory of the CPU 301. Various programs including a control program for implementing processing to be described below are loaded onto the RAM 303 from a hard disc drive (HDD) 305 or the like, and executed by the CPU 301. In addition, the RAM 303 provides a work area to be used when the CPU 301 executes various types of processing. A display 304 performs various types of display under the control of the CPU 301. The HDD 305 is used for storing and reading an application program, data, and a library. An input device 306 includes a pointing device, a keyboard, and the like. To a storage medium attachment unit (media drive) 307, a removable storage medium can be attached, so that data obtained by image capturing executed by the digital still camera can be read therefrom. A network interface (I/F) (communication unit) 308 is connected with a computer network 311 via a wireless or wired communication line 310. By the network interface 308, data is transmitted to or received from a device with which communication can be performed. In the present exemplary embodiment, the image processing apparatus connects with the imaging apparatus 101 via the network interface, and the CPU 301 transmits and receives various types of data to and from the imaging apparatus 101, acquires a captured image from the imaging apparatus 101, and records the captured image into the HDD 305. A system bus 309 (including an address bus, a data bus, and a control bus) connects the above-described components.

Sequence of Processing of Recording Disease State

Figure 4:
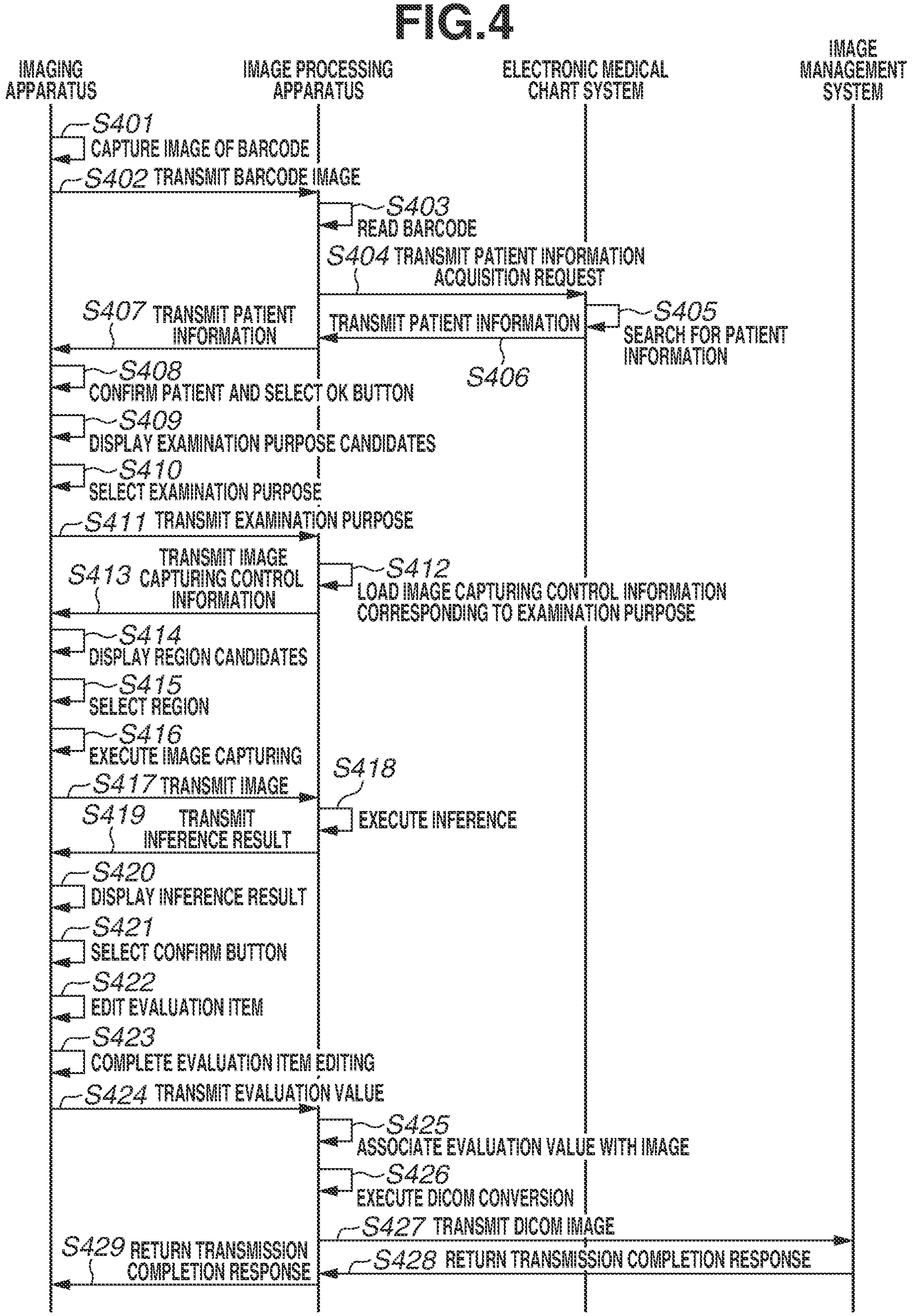
FIG. 4 is a sequence diagram illustrating processing of recording a disease state of a patient using the medical system.

FIG. 4 is a sequence diagram illustrating processing of recording a disease state of a patient using the medical system according to the present exemplary embodiment. In FIG. 4, the description will be mainly provided of a flow of data transmission and reception between apparatuses included in the medical system. These processes are implemented by the apparatuses and the system executing the processes based on control programs of the apparatuses and the system.

In step S401, the imaging apparatus 101 prompts an operator to capture an image of a barcode on a wristband of a patient, performs image capturing control in response to a shutter button operation performed by the operator, and records the barcode as image data.

In step S402, the imaging apparatus 101 transmits the image data of the barcode recorded in step S401, i.e., patient image data corresponding to the patient, to the image processing apparatus 106.

In step S403, the image processing apparatus 106 receives the image data of the barcode from the imaging apparatus 101, and performs barcode reading processing by analyzing the image data. The barcode reading processing is assumed to be general reading processing, and symbols and numbers indicated by the barcode are acquired. In the present exemplary embodiment, the patient management number of the patient wearing the wristband is acquired.

In step S404, the image processing apparatus 106 transmits a patient information acquisition request to the electronic medical chart system 104 using the patient management number acquired in step S403 as a search condition. At the time, in a case where information regarding a medical examination result of a past disease is stored, the image processing apparatus 106 transmits the acquisition request for patient information including an examination for a disease executed on a predetermined recent date and time. In the present exemplary embodiment, the predetermined recent date and time means within one month.

In step S405, based on the patient information acquisition request transmitted in step S404, the electronic medical chart system 104 searches for the patient information based on the patient management number.

In step S406, the electronic medical chart system 104 transmits the patient information that is a result of the search executed in step S405 to the image processing apparatus 106.

In step S407, the image processing apparatus 106 transmits the patient information received from the electronic medical chart system 104 in step S406 to the imaging apparatus 101.

In step S408, the imaging apparatus 101 displays a patient name, age, and gender included in the patient information received from the image processing apparatus 106 in step S407 as well as an OK button and an NG button on the display device 204 in the imaging apparatus 101. Then, the imaging apparatus 101 prompts the operator to confirm whether the displayed information matches information about a patient to be examined. In a case where the operator has selected the OK button, the processing proceeds to step S409 to be described below. In a case where the operator has selected the NG button, the processing returns to step S401.

In step S409, in a case where the patient information includes a plurality of examinations for a disease executed within one month, the imaging apparatus 101 displays the examinations on the display device 204 as examination purpose candidates. In addition, in a case where the patient information includes no examination, the imaging apparatus 101 displays all examination purposes on the display device 204 as candidates. Hereinafter, a screen for displaying the examination purpose candidates will be described as an examination purpose selection screen. A display method will be described below.

In step S410, the imaging apparatus 101 determines whether or not an examination purpose selection operation has been performed by the operator. In a case where the examination purpose selection operation has been performed, the processing proceeds to step S411. In a case where the examination purpose selection operation has not been performed, the imaging apparatus 101 continues to display the examination purpose candidates in step S409.

In step S411, the imaging apparatus 101 transmits an examination purpose selected by the operator in step S410, to the image processing apparatus 106.

In step S412, the image processing apparatus 106 loads image capturing control information corresponding to the examination purpose from the HDD 305 onto the RAM 303. The correspondence between examination purposes and image capturing control information will be described below.

In step S413, the image processing apparatus 106 transmits the image capturing control information to the imaging apparatus 101.

In step S414, the imaging apparatus 101 stores the image capturing control information in the RAM 203, and displays region candidates of the patient on the display device 204 based on the image capturing control information. Then, the imaging apparatus 101 prompts the operator to select a region. Hereinafter, a screen for displaying the region candidates will be described as a region selection screen. The display method will be described below.

In step S415, the imaging apparatus 101 determines whether or not a region selection operation has been performed by the operator. In a case where the region selection operation has been performed, the state transitions to a state of receiving an image capturing operation, and the processing proceeds to step S416 to be described below. In a case where the region selection operation has not been performed, the imaging apparatus 101 continues to display the region candidates in step S414.

In step S416, the imaging apparatus 101 performs a series of image capturing processes in accordance with an image capturing operation (image capturing instruction) performed by the operator on the shutter button, and stores generated image data in the media drive 206 as an affected part image. At the time, an image ID that enables the image data to be uniquely identified in the medical system of the present exemplary embodiment is generated, and recorded in a header of the image data.

In step S417, the imaging apparatus 101 transmits the image data (affected part image) generated in step S416 to the image processing apparatus 106 together with an image capturing condition used during the image capturing, the examination purpose selected in step S410, the patient information and the patient management number received in step S407, and the image capturing target region selected in step S415. These pieces of information may be included in an image file of the image data and transmitted, or may be transmitted as a separate file. It is sufficient that image data and each piece of information are associated with each other.

In step S418, the image processing apparatus 106 stores the image data, the image capturing condition, the examination purpose, the image capturing target region, and the patient management number that have been received from the imaging apparatus 101 in the HDD 305 in association with an image ID. Then, the image processing apparatus 106 loads the image data onto the RAM 303 depending on the examination purpose, analyze the image data, and executes inference for diagnostic aid. The inference for diagnostic aid is inference of a region and a state of an affected part that is performed by machine learning. A learning model to be used in the machine learning is stored in the HDD 305 and loaded onto the RAM 303 when the inference is executed. Then, the image processing apparatus 106 also calculates information regarding an area and the state of the affected part that can be converted into numbers. In the case of pressure sore, the image processing apparatus 106 analyzes an area of the affected part, a pressure sore portion, a necrotic portion, an inflamed/infected portion, a granulation tissue portion, and depth information. As for the pressure sore portion, a necrotic tissue portion, the inflamed/infected portion, the granulation tissue portion, and the depth information, from captured images of instances of pressure sore, the image processing apparatus 106 preliminarily creates supervised data indicating to which state each pixel corresponds based on colors and the distribution of pixels included in the image. Then, the image processing apparatus 106 creates a learning model by performing machine learning using the supervised data, and executes inference. The depth information of pressure sore is not information regarding a physical depth, but is information indicating a degree to which a tissue beneath the skin is exposed. In other cases of a medical examination of asteatosis cutis, atopic dermatitis, psora, burn injury, hives, and teeth, the image processing apparatus 106 creates supervised data from images of their symptoms. Then, similarly to the case of pressure sore, the image processing apparatus 106 creates a learning model, executes inference, and outputs an inference result (analysis result). In the following description of the present exemplary embodiment, it is described that inference processing is executed by creating the above-described learning model that uses machine learning. Nevertheless, analysis may be performed using luminance information, color information, hue information, gradient information, or the like of an image, for example, and inference processing may be performed using the gradient information or a distribution of regional color or intensity information. The inference processing may be performed based on feature matching that uses shape feature information of a grayscale distribution or luminance gradient, or the inference processing may be performed by extracting pixels with a luminance gradient of a fixed value or more as edge information, and using, in combination, rule-based image processing such as detection of pixel positions, centroid, and gradient.

In step S419, the image processing apparatus 106 transmits, to the imaging apparatus 101, image data serving as an inference result (analysis result), and numerical information indicating a state, together with the image ID of image data that is a target of the inference. The imaging apparatus 101 receives the inference result (analysis result) and the image ID that have been transmitted from the image processing apparatus 106 (image analysis result reception).

In step S420, the imaging apparatus 101 displays the numerical information indicating a state, which serves as an inference result (analysis result), on the display device 204 in a superimposed manner on the image data obtained by image capturing executed in step S416 (image data corresponding to the received image ID). Moreover, the imaging apparatus 101 displays a confirm button and a retake button, and prompts the operator to confirm the target image and the inference result for any mistakes. Hereinafter, a screen for displaying an inference result will be described as an inference result display screen. The display method will be described below.

In step S421, in a case where the imaging apparatus 101 determines that the confirm button has been selected by the operator, the processing proceeds to step S422. In a case where the imaging apparatus 101 determines that the retake button has been selected, the processing returns to step S416.

In step S422, based on the image capturing control information, the imaging apparatus 101 displays, on the display device 204, a screen for selecting an evaluation item and an evaluation value to be a candidate associated with the evaluation item. Then, the imaging apparatus 101 prompts the operator to edit the evaluation value. Hereinafter, a screen for editing the evaluation value will be described as an evaluation value edit screen. In a case where a state has been acquired from the inference result as a numerical value, an evaluation value corresponding to the numerical value is displayed in a selected state on the evaluation value edit screen. In a case where a state has not been acquired from the inference result as a numerical value, an evaluation value is displayed in an unselected state. In addition, a complete button is arranged on the evaluation value edit screen. The display method will be described below.

In step S423, in a case where the imaging apparatus 101 determines that the complete button has been selected by the operator, the processing proceeds to step S424. In a case where a selection operation has not been performed on the complete button, the imaging apparatus 101 continues to display the evaluation value edit screen in step S422.

In step S424, the imaging apparatus 101 transmits the evaluation value selected on the evaluation value edit screen to the image processing apparatus 106 together with the image ID and the patient management number.

In step S425, the image processing apparatus 106 stores, in the RAM 303, the image data that is the target of the inference and the evaluation value received from the imaging apparatus 101 in association with each other using the image ID.

In step S426, the image processing apparatus 106 converts the format of the image into a medical image format "Digital Imaging and Communications in Medicine" (registered trademark) (hereinafter, abbreviated as DICOM) in the form including patient information, an examination purpose, an image capturing target region, an evaluation value, and image data.

In step S427, the image processing apparatus 106 transmits the DICOM (registered trademark) image to the image management system 105 together with the patient information (patient management number, etc.), the examination purpose, the image capturing target region, and the inference result image.

In step S428, the image management system 105 returns a transmission completion response to the image processing apparatus 106.

In step S429, the image processing apparatus 106 returns a transmission completion response to the imaging apparatus 101.

Image Capturing Control Information

FIG. 5 is a conceptual diagram illustrating a correspondence relationship between image capturing control information and examination purposes according to the present exemplary embodiment. In the present exemplary embodiment, the information illustrated in FIG. 5 is stored in the HDD 305 in the image processing apparatus 106, and is information to be used when image capturing control information corresponding to the examination purpose received from the imaging apparatus 101 in step S411 is loaded in step S412.

A column 501 indicates examination purposes. The column 501 is associated with a disease of an affected part of a patient.

A column 502 indicates image capturing conditions. An image capturing condition to be designated in the imaging apparatus 101 to capture an image appropriate for medical examination aid is held for each examination purpose, and made unmodifiable by an operation of the operator. A parameter not designated in the image capturing condition is modifiable by a user operation performed by the operator on the input device 205 on the imaging apparatus 101.

A column 503 indicates region candidates. The region candidates are region candidates to be displayed on the imaging apparatus 101. Region candidates appropriate for each examination purpose are held. Depending on examination purposes, the disease state is diagnosed based on the appearance of a symptom throughout the total body in some cases, and the disease state is diagnosed based on the appearance of a symptom on a partial region in other cases. The region candidates can be switched based on the selection made by the operator with regard to which image to record using the imaging apparatus 101.

A column 504 indicates assisting graphics to be displayed at the time of image capturing. The column 504 indicates graphics to be displayed on the display device 204 in a superimposed manner on a subject image, when an image of an affected part is captured by the imaging apparatus 101. Depending on examination purposes, the disease state is diagnosed based on the appearance of a symptom throughout the total body in some cases, and the disease state is diagnosed based on the appearance of a symptom on a partial region in other cases. In a case where the disease state is diagnosed based on the appearance of a symptom throughout the total body, the assisting graphic is switched depending on a selected region.

A column 505 indicates confirmation conditions. A condition for determining whether or not an image suitable for diagnosis has been captured for each examination purpose is held. _The confirmation condition for determining whether or not an image suitable for diagnosis has been captured varies between the case where the disease state is diagnosed based on the appearance of a symptom throughout the total body and the case where the disease state is diagnosed based on the appearance of a symptom on a partial region. The confirmation condition can be switched based on the selection made by the operator with regard to which image to record using the imaging apparatus 101.

A column 506 indicates information regarding inference result display. Whether or not to display an inference result obtained by the image processing apparatus 106 on the imaging apparatus 101, and information to be the inference result are held.

A column 507 indicates evaluation items. Evaluation items suitable for each examination purpose are held.

A column 508 indicates evaluation values for each evaluation item. Values included in the evaluation item associated with each examination purpose are held.

A column 509 indicates whether or not determination based on multiple images is executable. Depending on examination purposes, the disease state can be determined based on multiple images in some cases, and the disease state can be determined based on a single image in other cases. Information indicating either case is held.

A column 510 indicates whether or not image capturing of multiple regions is required. Depending on examination purposes, there is a case where images of a plurality of regions are always required to be captured to determine a state, and the column 510 holds whether there is the plurality of regions to be image-captured. In addition, the column 510 may also hold information regarding a region where an image is required to be captured. Furthermore, information may be held in such a manner that information to be applied varies between a case where a symptom is determined based on the total body (total body flag on), and a case where a symptom is not determined based on the total body.

A row 511 indicates image capturing control information to be loaded in a case where a disease set as the examination purpose is pressure sore.

A row 512 indicates image capturing control information to be loaded in a case where the disease set as the examination purpose is burn injury.

A row 513 indicates image capturing control information to be loaded in a case where the disease set as the examination purpose is asteatosis cutis.

A row 514 indicates image capturing control information to be loaded in a case where the disease set as the examination purpose is atopic dermatitis.

A row 515 indicates image capturing control information to be loaded in a case where the disease set as the examination purpose is psora.

A row 516 indicates image capturing control information to be loaded in a case where the disease set as the examination purpose is hives.

A row 517 indicates image capturing control information to be loaded in a case where a target set as the examination purpose is teeth.

In a case where the examination purpose is pressure sore in step S411, in step S412, the image processing apparatus 106 loads information in the row 511 that corresponds to pressure sore onto the RAM 303 by the control of the CPU 301. Then, in step S413, the image processing apparatus 106 transmits the image capturing control information to the imaging apparatus 101.

In a case where the examination purpose is burn injury in step S411, the image processing apparatus 106 similarly loads information in the row 512 that corresponds to burn injury onto the RAM 303, and in step S413, transmits the image capturing control information to the imaging apparatus 101.

In a case where the examination purpose is asteatosis cutis, atopic dermatitis, psora, hives, or teeth, image capturing control information on the row corresponding to each examination purpose is similarly transmitted to the imaging apparatus 101.

Image Capturing Control Processing

Figure 6A:
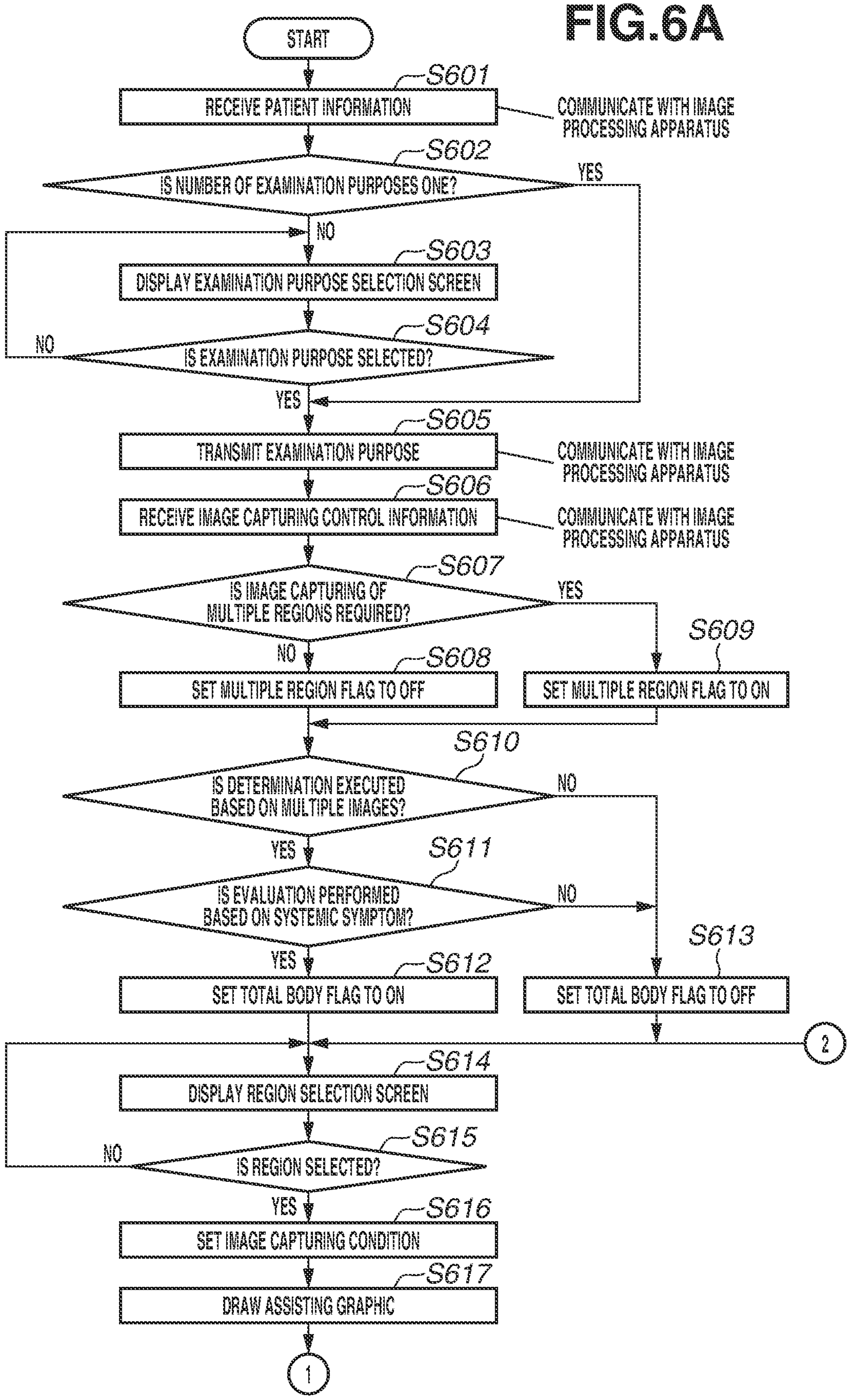
FIGS. 6A and 6B are flowcharts illustrating image capturing control processing.
Figure 6B:
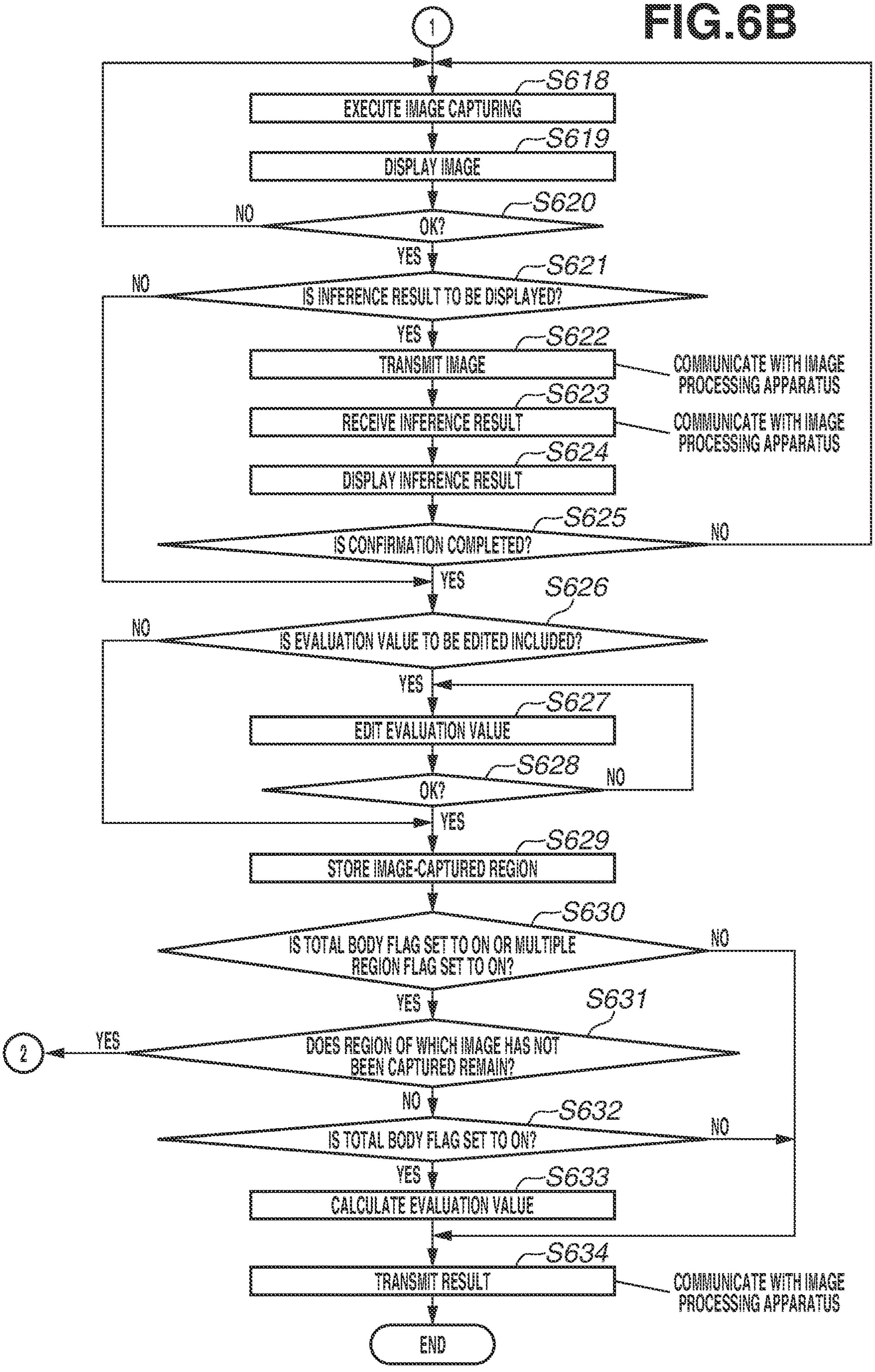

FIG. 6 is a flowchart illustrating image capturing control processing according to the present exemplary embodiment. A method of changing an image capturing condition, screen display content, and image additional information based on the image capturing control information in the imaging apparatus 101 will be described with reference to FIGS. 5 and 6. For a process that has already been described with reference to FIG. 4, a corresponding step number will be described. In FIG. 4, the description has been mainly provided of the flow of data transmission and reception between the apparatuses included in the medical system. In FIG. 6, processing in the imaging apparatus 101 will be described in detail. The processing in the flowchart is implemented by the imaging apparatus 101 reading a control program and executing processing based on the read control program.

In step S601, the CPU 201 acquires patient information from the image processing apparatus 106. The processing in step S601 corresponds to the processing in step S407. Since patient confirmation in step S408 has been described with reference to FIG. 4, the description will be omitted.

The processing in steps S602 and S603 corresponds to the processing in step S409.

In step S602, the CPU 201 determines whether or not the number of examination purposes included in the patient information is one. In a case where the number of examination purposes included in the patient information is one, it is determined that the examination purpose has been uniquely identified, and the examination purpose is automatically selected without displaying the examination purpose selection screen to be described below, and the processing proceeds to step S605. In a case where the number of examination purposes included in the patient information is not one, the processing proceeds to step S603.

In step S603, in a case where a plurality of examinations for a disease executed within one month is included in the patient information, the CPU 201 displays, on the display device 204, the examinations for a disease as the examination purpose candidates on the examination purpose selection screen to be described below. In addition, in a case where no examination is included in the patient information, the CPU 201 displays, on the display device 204, all examination purposes as the candidates on the examination purpose selection screen to be described below.

In step S604, the CPU 201 determines whether or not an examination purpose selection operation has been performed by the operator. The processing in step S604 corresponds to the processing in step S410. In a case where it is determined that the examination purpose selection operation has been performed, the processing proceeds to step S605. In a case where the examination purpose selection operation has not been performed, the processing returns to step S603, and the CPU 201 continues to display the examination purpose selection screen.

In step S605, the CPU 201 transmits the examination purpose selected by the operator in step S604, or the examination purpose uniquely identified in step S602, to the image processing apparatus 106. The processing in step S605 corresponds to the processing in step S411.

In step S606, the CPU 201 receives the image capturing control information from the image processing apparatus 106 and stores the received image capturing control information in the RAM 203. The processing in step S606 corresponds to the processing in step S413.

The processing in steps S607 to S617 corresponds to the processing in steps S414 to S416, and the processing in the imaging apparatus 101 is described in more detail.

In step S607, the CPU 201 refers to information in the column 510 in the image capturing control information, and determines whether or not image capturing of multiple regions is required. In a case where it is determined that the image capturing of multiple regions is required, the processing proceeds to step S609. In a case where it is determined that the image capturing of multiple regions is not required, the processing proceeds to step S608.

In step S608, the CPU 201 sets a multiple region flag indicating that image capturing of multiple regions is required to off.

In step S609, the CPU 201 sets the multiple region flag indicating that image capturing of multiple regions is required to on.

In step S610, the CPU 201 refers to information in the column 509 in the image capturing control information, and determines whether or not determination based on multiple images is executable. In a case where the determination based on multiple images is to be executed, the processing proceeds to step S611. In a case where the determination based on multiple images is not to be executed, the processing proceeds to step S613.

In step S611, the CPU 201 displays, on the display device 204, a screen for prompting the operator to select whether or not to make evaluation based on a systemic symptom, and determines whether or not the operator has performed an operation of selecting the evaluation based on a systemic symptom. In a case where the evaluation based on a systemic symptom has been selected, at the time of the evaluation, the systemic symptom is evaluated based not only on evaluation of a single region but also on evaluation of a plurality of regions. In a case where the operator has selected the evaluation based on a systemic symptom, the processing proceeds to step S612. In a case where the operator has not selected the evaluation based on a systemic symptom, the processing proceeds to step S613.

In step S612, the CPU 201 captures images of a plurality of regions, and sets the total body flag indicating that evaluation that is based on a systemic symptom is to be executed based on the captured images of the plurality of regions, to on.

In step S613, the CPU 201 sets the total body flag indicating that the evaluation that is based on a systemic symptom is to be executed, to off.

In step S614, the CPU 201 refers to information in the column 503 in the image capturing control information, and displays, on the display device 204, the region selection screen for selecting an image capturing target region from among the region candidates. The CPU 201 refers to the image capturing control information, and displays only regions selectable by the operator on the region selection screen as the region candidates, and does not display unselectable regions on the region selection screen. In a case where the region candidates vary depending on whether the total body flag is set to on or off, the CPU 201 displays regions conforming to the total body flag on the region selection screen as the region candidates, and brings the regions into an operator-selectable state. When displaying the region selection screen, the CPU 201 refers to information in the column 510 in the image capturing control information, and displays the region selection screen in such a manner that a region required to be image-captured is identifiable as the region required to be image-captured. For example, the CPU 201 desirably displays a character, a symbol, or a mark indicating that image capturing is required together with a region candidate, or displays the region candidates while varying color between region candidates required to be image-captured and region candidates not required to be image-captured.

In step S615, the CPU 201 determines whether or not a region selection operation has been performed by the operator on the region selection screen. The processing in step S615 corresponds to the processing in step S415. In a case where the region selection operation has been performed, the CPU 201 determines the selected region as an image capturing target region, and the processing proceeds to step S616 to perform image capturing of the determined image capturing target region. In a case where the selection operation has not been performed, the CPU 201 continues to display the region selection screen in step S614.

In step S616, the CPU 201 refers to information in the image capturing condition column 502 in the image capturing control information, and controls the imaging unit 200 in such a manner that image capturing can be executed with a parameter satisfying an image capturing condition. In a case where the image capturing condition varies depending on whether the total body flag is set to on or off, an image capturing condition conforming to the total body flag is employed as the parameter.

In step S617, the CPU 201 refers to information in the assisting graphic column 504 in the image capturing control information, and displays an image capturing assisting graphic in a superimposed manner on a captured live view image. The image capturing assisting graphic is a graphic for assisting the operator to capture an appropriate examination image, and the type of assisting graphic to be displayed in the superimposed manner on the live view image is changed in accordance with image capturing control information. In addition, in a case where the image capturing assisting graphic varies depending on whether the total body flag is set to on or off, an image capturing assisting graphic conforming to the total body flag is employed. In a case where the image capturing assisting graphic is an affected part outline of a selected region in the last image capturing (in the last examination), the affected part image in the last image capturing that has been acquired as the patient information in step S601 is read, and an outline of the affected part is drawn. Nevertheless, in a case where there is no applicable image within a predetermined period, the image capturing assisting graphic is not drawn. In the present exemplary embodiment, the predetermined period is set to one month.

In step S618, in accordance with an image capturing operation performed by the operator, the CPU 201 performs a series of image capturing processes using the imaging unit 200, the image processing unit 211, and the file generation unit 212, and stores generated image data in the media drive 206. The processing in step S618 corresponds to the processing in step S416.

In step S619, the CPU 201 displays the image data generated in step S618 on the display device 204.

In step S620, the CPU 201 refers to information in the confirmation condition column 505 in the image capturing control information, and determines whether or not image data suitable for the examination purpose has been generated. In a case where a confirmation condition varies depending on whether the total body flag is set to on or off, a confirmation condition conforming to the total body flag is employed. In a case where the confirmation condition is satisfied, it is determined that an image suitable for the examination purpose has been generated. In a case where the confirmation condition is unsatisfied, it is determined that an image suitable for the examination purpose has not been generated. In a case where it is determined that the image suitable for the examination purpose has been generated, the processing proceeds to step S621. In a case where it is determined that the image suitable for the examination purpose has not been generated, the CPU 201 displays information for assisting image capturing depending on the unsatisfied confirmation condition, returns the processing to step S618, and prompts the operator to execute image capturing again. The confirmation processing executed in step S620 will be described below with reference to FIG. 7.

In step S621, the CPU 201 refers to information in the column 506 indicating whether to display an inference result in the image capturing control information, and determines whether or not to display an inference result on the display device 204 of the imaging apparatus 101. In a case where it is determined that an inference result is to be displayed, the processing proceeds to step S622. In a case where it is determined that an inference result is not to be displayed, the processing proceeds to step S626.

In step S622, the CPU 201 transmits image data to the image processing apparatus 106 together with an image capturing condition used during the image capturing, an examination purpose, and a patient management number. The processing in step S622 corresponds to the processing in step S417.

In step S623, the CPU 201 receives, from the image processing apparatus 106, the image data serving as an inference result, and numerical information indicating a state, together with an image ID of the image data that is a target of the inference. The processing in step S623 corresponds to the processing in step S419.

In step S624, the CPU 201 displays the inference result and the numerical information indicating the state in a superimposed manner on the image data obtained by image capturing. The processing in step S624 corresponds to the processing in step S420.

In step S625, the CPU 201 determines whether or not inference result confirmation has been completed. In a case where it is determined that the confirm button has been selected by the operator, the processing proceeds to step S626. In a case where it is determined that the retake button has been selected, the processing returns to step S618. The processing in step S625 corresponds to the processing in step S421.

In step S626, the CPU 201 refers to the evaluation item column 507 in the image capturing control information, and determines whether or not an evaluation value to be edited on the imaging apparatus 101 is included. In a case where it is determined that an evaluation value to be edited on the imaging apparatus 101 is included, the processing proceeds to step S627. In a case where it is determined that an evaluation value to be edited on the imaging apparatus 101 is not included, the processing proceeds to step S629.

In step S627, the CPU 201 configures a screen based on information on the evaluation item column 507 and the evaluation value column 508 in the image capturing control information, and displays the evaluation value edit screen, to be described below, on the display device 204. The processing in step S627 corresponds to the processing in step S422.

In step S628, the CPU 201 determines whether or not an edit completion button has been selected by the operator. In a case where it is determined that the edit completion button has been selected, the processing proceeds to step S629. In a case where the edit completion button has not been selected, the processing returns to step S627, and the CPU 201 continues to display the evaluation value edit screen. The processing in step S628 corresponds to the processing in step S423.

In step S629, the CPU 201 stores an image-captured region in the RAM 203.

In step S630, the CPU 201 determines whether or not the total body flag or the multiple region flag is set to on. In a case where the total body flag or the multiple region flag is set to on, the processing proceeds to step S631. In a case where both the total body flag and the multiple region flag are set to off, it is determined that image capturing of multiple regions is not required, and the processing proceeds to step S634.

In step S631, the CPU 201 refers to the column 510 indicating whether image capturing of multiple regions is required in the image capturing control information, checks the multiple regions against the image-captured region stored in the RAM 203 in step S629, and determines whether or not a region of which image capturing has not been executed remains. In a case where a region required to be image-captured varies depending on whether the total body flag is set to on or off, information regarding a region that conforms to the total body flag is employed. In a case where it is determined that a region of which image capturing has not been executed remains, the processing returns to step S614. In a case where it is determined that a region of which image capturing has not been executed is not left, the processing proceeds to step S632.

In step S632, the CPU 201 determines whether or not the total body flag is set to on. In a case where the total body flag is set to on, the processing proceeds to step S633. In a case where the total body flag is set to off, the processing proceeds to step S634.

In step S633, the CPU 201 calculates an evaluation value to evaluate a disease based on a symptom throughout the total body. A method of calculating a total body evaluation value of atopic dermatitis as an Eczema Area and Severity Index (EASI) Score is represented by Formula 1. In Formula 1, evaluation values of erythema, erosion/papula, scratch, and lichenification and a region score for an area of erosion of a head/neck are denoted by head1, head2, head3, head4, and head5, respectively. Evaluation values of erythema, erosion/papula, scratch, and lichenification and a region score for an area of erosion of a body trunk are denoted by body1, body2, body3, body4, and body5, respectively. Evaluation values of erythema, erosion/papula, scratch, and lichenification and a region score for an area of erosion of an upper extremity are denoted by arm1, arm2, arm3, arm4, and arm5, respectively. Evaluation values of erythema, erosion/papula, scratch, and lichenification and a region score for an area of erosion of a lower extremity are denoted by foot1, foot2, foot3, foot4, and foot5, respectively.

$$\text{EASI Score}=(\text{head1}+\text{head2}+\text{head3}+\text{head4})\times\text{head5}\times 0.1+(\text{body1}+\text{body2}+\text{body3}+\text{body4})\times\text{body5}\times 0.3+(\text{arm1}+\text{arm2}+\text{arm3}+\text{arm4})\times\text{arm5}\times 0.2+(\text{foot1}+\text{foot2}+\text{foot3}+\text{foot4})\times\text{foot5}\times 0.4 \qquad \text{(Formula 1)}$$

In a similar manner, evaluation values of burn injury, asteatosis cutis, psora, and hives are calculated based on general disease evaluation formulas from systemic symptoms.

In step S634, the CPU 201 transmits the evaluation value selected in step S627 and the evaluation value calculated in step S633 to the image processing apparatus 106 together with the image ID and the patient management number. In a case where there is no evaluation value, the CPU 201 transmits unsent image data to the image processing apparatus 106 together with the patient management number.

Captured Image Confirmation Processing

Figure 7:
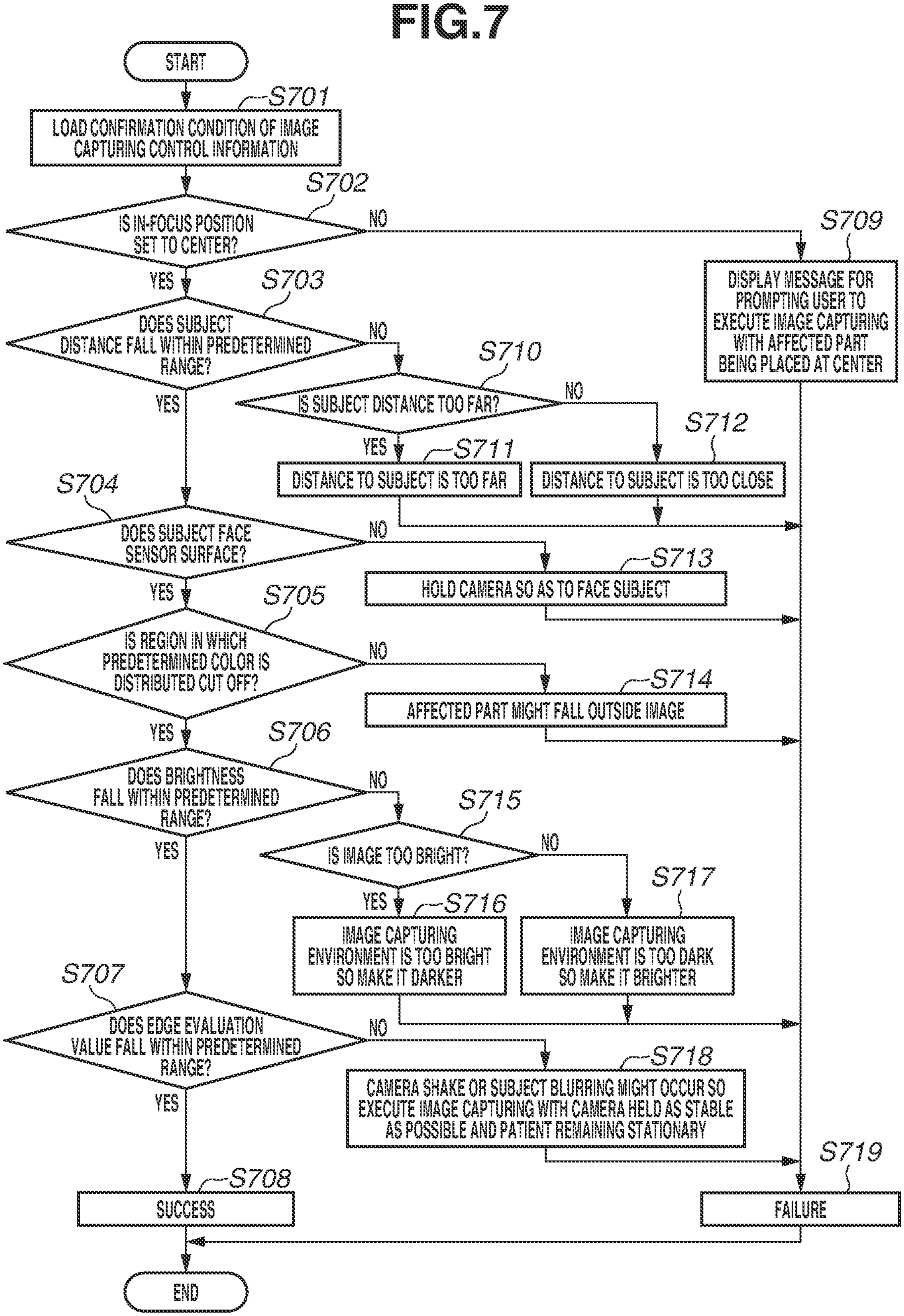
FIG. 7 is a flowchart illustrating captured image confirmation processing.

FIG. 7 is a flowchart illustrating captured image confirmation processing according to the present exemplary embodiment. By the processing, whether an image suitable for an examination purpose has been generated is confirmed. The above-described processing in step S620 will be described in detail. The description will be provided of an example where the examination purpose is pressure sore. The processing in the flowchart is implemented by the imaging apparatus 101 reading a control program and executing processing based on the read control program.

In step S701, the CPU 201 loads information in the confirmation condition column 505 in the image capturing control information onto the RAM 203. In a case where the examination purpose is pressure sore, in step S702 and subsequent steps to be described below, it is confirmed that an in-focus position is set to the center, a subject distance falls within a predetermined value range, a sensor surface faces a subject, a region in which a predetermined color is distributed is not cut off, and a brightness/edge evaluation value falls within a predetermined value range. In the evaluation, image data, an image capturing condition stored in the RAM 203 in association with the image data, and measurement information obtained by a ranging sensor for focusing are used.

In step S702, the CPU 201 determines whether or not an in-focus position in image capturing is the center of an image. The in-focus position in the image is held in header information added to the image data as coordinate information. If the in-focus position falls within a predetermined range from a center coordinate of the image, it is determined that the in-focus position is the center, and the processing proceeds to step S703. In a case where it is determined that the in-focus position is not the center, the processing proceeds to step S709.

In step S703, the CPU 201 determines whether or not a distance between a sensor surface of the imaging apparatus 101 and a subject falls within a predetermined range. The distance between the sensor surface and the subject can be calculated based on information obtained by the ranging sensor during image capturing. Then, a numerical value indicating the distance is held as subject distance information in the header information added to the image data. In a case where it is determined that a subject distance falls within a predetermined range, the processing proceeds to step S704. In a case where it is determined that the subject distance falls outside the predetermined range, the processing proceeds to step S710.

In step S704, the CPU 201 determines whether or not the sensor surface of the imaging apparatus 101 faces the subject. Whether or not the sensor surface of the imaging apparatus 101 faces the subject is determined using a distance measurement evaluation value on the image, and in a case where the subject distance drastically varies among an upper portion, a lower portion, a right portion, and a left portion on the image, it is determined that the sensor surface does not face the subject. In a case where it is determined that the subject faces the sensor surface, the processing proceeds to step S705. In a case where it is determined that the subject does not face the sensor surface, the processing proceeds to step S713.

In step S705, the CPU 201 determines whether or not a region in which a predetermined color is distributed is cut off from the image. In the case of pressure sore, the predetermined color is a color with higher redness than normal skin color. The determination is made based on whether or not the region in which the predetermined color is distributed protrudes from an end of the image. In a case where it is determined that the region protrudes, the processing proceeds to step S714. In a case where it is determined that the region does not protrude, the processing proceeds to step S706.

In step S706, the CPU 201 determines whether or not brightness of the image falls within a predetermined range. Whether or not the brightness of the image falls within a predetermined range is determined based on whether or not an average value of pixel values of pixels constituting the image falls within a predetermined range. In a case where it is determined that the brightness of the image falls within a predetermined range, the processing proceeds to step S707. In a case where it is determined that the brightness of the image falls outside a predetermined range, the processing proceeds to step S715.

In step S707, the CPU 201 determines whether or not an edge evaluation value falls within a predetermined range. The edge evaluation value is calculated by applying a smoothing filter to luminance pixel values of the image and calculating an average value of differences in luminance pixel value between an original image and a smoothed image. Then, in a case where the edge evaluation value is smaller than a predetermined value, it is determined that the image data is image data lacking fineness. In a case where it is determined that the edge evaluation value falls within a predetermined range, the processing proceeds to step S708. In a case where it is determined that the edge evaluation value falls outside a predetermined range, the processing proceeds to step S718.

In step S708, the CPU 201 determines that an image suitable for the examination purpose has been generated, and stores a confirmation result indicating a success in the RAM 203 in association with the image data.

In step S709, to notify the operator that the in-focus position is shifted from the center, the CPU 201 displays a message for prompting the operator to execute image capturing with an affected part placed at the center, on the display device 204.

In step S710, the CPU 201 determines whether or not the subject distance is too far. In a case where it is determined that the subject distance is too far, the processing proceeds to step S711. In a case where it is determined that the subject distance is not too far, i.e., too close, the processing proceeds to step S712.

In step S711, to notify the operator that the subject distance is too far, the CPU 201 displays a message indicating that the distance to the subject is too far, on the display device 204.

In step S712, to notify the operator that the subject distance is too close, the CPU 201 displays a message indicating that the distance to the subject is too close, on the display device 204.

In step S713, to notify the operator that the subject is not facing the imaging apparatus, the CPU 201 displays a message for prompting the operator to hold the camera so as to face the subject, on the display device 204.

In step S714, to notify the operator that a region of an affected part protrudes from the image, the CPU 201 displays a message indicating that the affected part might fall outside the image, on the display device 204.

In step S715, the CPU 201 determines whether or not the brightness of the image is too bright. In a case where it is determined that the brightness of the image is too bright, the processing proceeds to step S716. In a case where it is determined that the brightness of the image is not too bright, i.e., too dark, the processing proceeds to step S717.

In step S716, to notify the operator that an image capturing environment is too bright, the CPU 201 displays a message indicating that an image capturing environment is too bright and is to be made darker, on the display device 204.

In step S717, to notify the operator that an image capturing environment is too dark, the CPU 201 displays a message indicating that an image capturing environment is too dark and is to be made brighter, on the display device 204.

In step S718, the CPU 201 notifies the operator that the image data significantly lacks edges and fineness. In the notification, for example, the CPU 201 displays a message indicating that "camera shake or subject blurring might have occurred, and image capturing is to be executed with the camera being held as stable as possible and the patient remaining stationary," on the display device 204.

In step S719, the CPU 201 determines that an image suitable for the examination purpose has not been generated, and stores a confirmation result indicating a failure in the RAM 203 in association with the image data. Then, the CPU 201 prompts the operator to execute image capturing again.

User Interface on Imaging Apparatus

Figure 8:
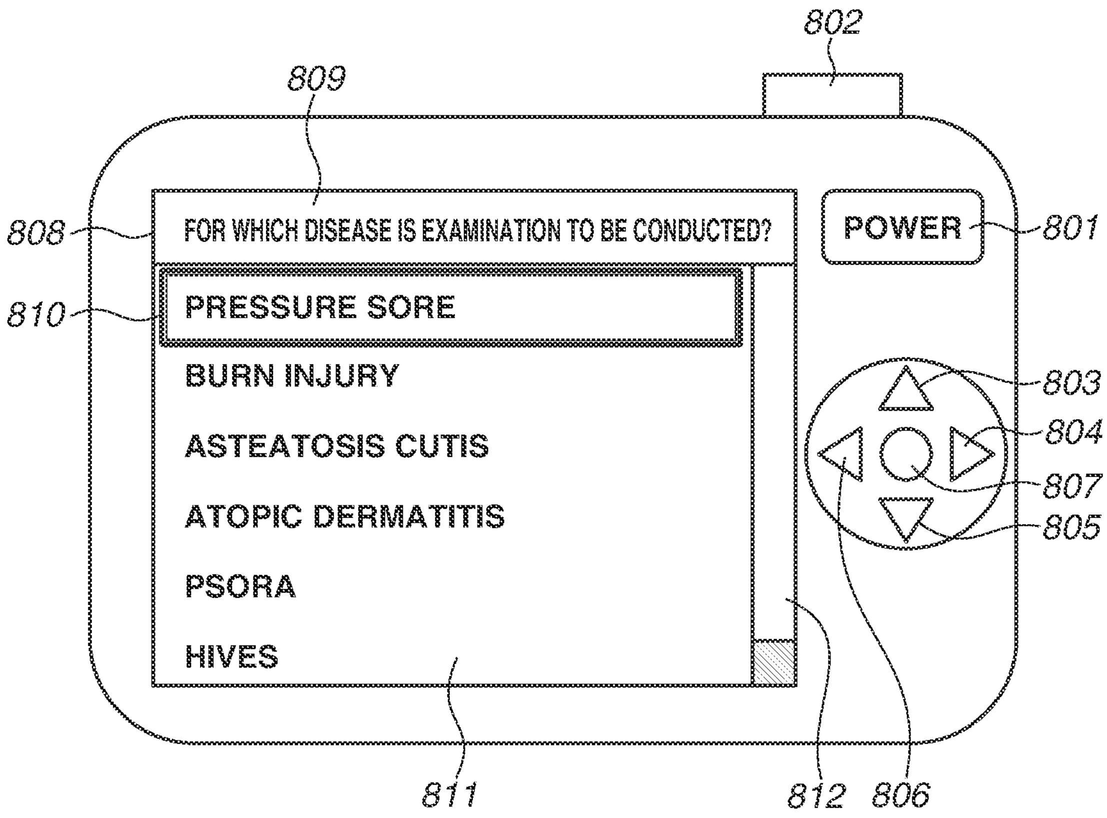
FIG. 8 is a diagram illustrating a state in which a digital still camera is viewed from the back side.

FIG. 8 illustrates a state in which a digital still camera operating as an imaging apparatus according to an exemplary embodiment of the present invention is viewed from the back side. Details of various buttons and a user interface of the digital still camera operating as the imaging apparatus according to the present exemplary embodiment will be described with reference to FIG. 8. FIG. 8 illustrates an example in which the above-described examination purpose selection screen is displayed. Operations on all buttons other than a power button 801 that are to be performed when the digital still camera is powered on will be described.

The power button 801 is a button for switching between on and off of the power. If the operator presses the power button 801 in a state in which the digital still camera is powered off, the CPU 201 determines that a power input instruction has been issued by the operator, and powers on the digital still camera. If the operator presses the power button 801 in a state in which the digital still camera is powered on, the CPU 201 determines that a power off instruction has been issued by the operator, and powers off the digital still camera.

A release button 802 is a release button. In a case where the operator has pressed the release button 802, the CPU 201 determines that a still image capturing instruction has been issued.

An up button 803, a right button 804, a down button 805, a left button 806, and a determination button 807 fulfill a function of the input device 205. In a case where the operator has pressed any button of the buttons 803 to 806, the CPU 201 determines that a selection target switching operation has been performed by the operator, and switches a selection target on a display 808 to be described below. In a case where the operator has pressed the button 807, the CPU 201 determines that a determination operation has been performed by the operator, and stores selected information in the RAM 203 and switches the state of the imaging apparatus 101. Such an operation corresponds to the selection operation in step S604 and the selection operation in step S615, which have been described above.

The display 808 has a function of the display device 204. The display 808 has a touch panel function in addition to a display function, and fulfills the function of the input device 205. When the operator has pressed any point on a screen with a finger, the CPU 201 determines that an input instruction has been issued by the operator, determines an operation content based on a pressed position, and performs various types of processing such as display update.

A screen title 809 displays a character string for informing the operator what to select.

A focus frame 810 is a frame for informing the operator of an item in a selected state.

A selection item display region 811 is a region for listing option candidates.

A scroll bar 812 is used for switching a display region in a case where candidates of selection items cannot be displayed in the selection item display region.

With regard to the focus frame 810, in a case where the operator has pressed any button of the buttons 803 to 806, the CPU 201 determines that a selection change operation has been performed by the operator, and moves the focus frame 810 within the selection item display region 811.

Figure 9:
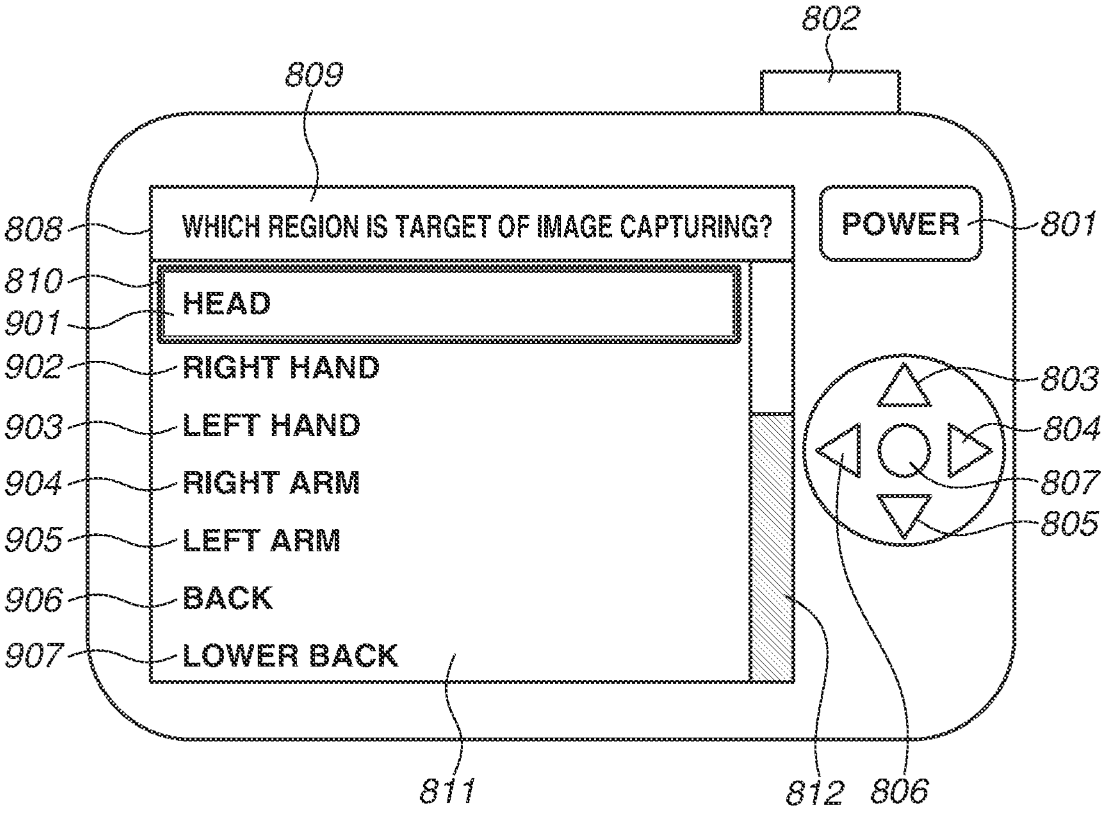
FIG. 9 is a diagram illustrating a state in which the digital still camera is viewed from the back side.

FIG. 9 is a diagram illustrating a state in which a digital still camera operating as an imaging apparatus according to an exemplary embodiment of the present invention is viewed from the back side. FIG. 9 illustrates an example of a region selection screen to be displayed in a case where an examination purpose is pressure sore. Members fulfilling the same functions as those illustrated in FIG. 8 are assigned the same reference numerals as those illustrated in FIG. 8.

Candidate regions 901, 902, 903, 904, 905, 906, and 907 are candidates of regions. As described in step S614, information in the region candidate column 503 in the row 511 for pressure sore set as the examination purpose in the image capturing control information is displayed.

Figure 10:
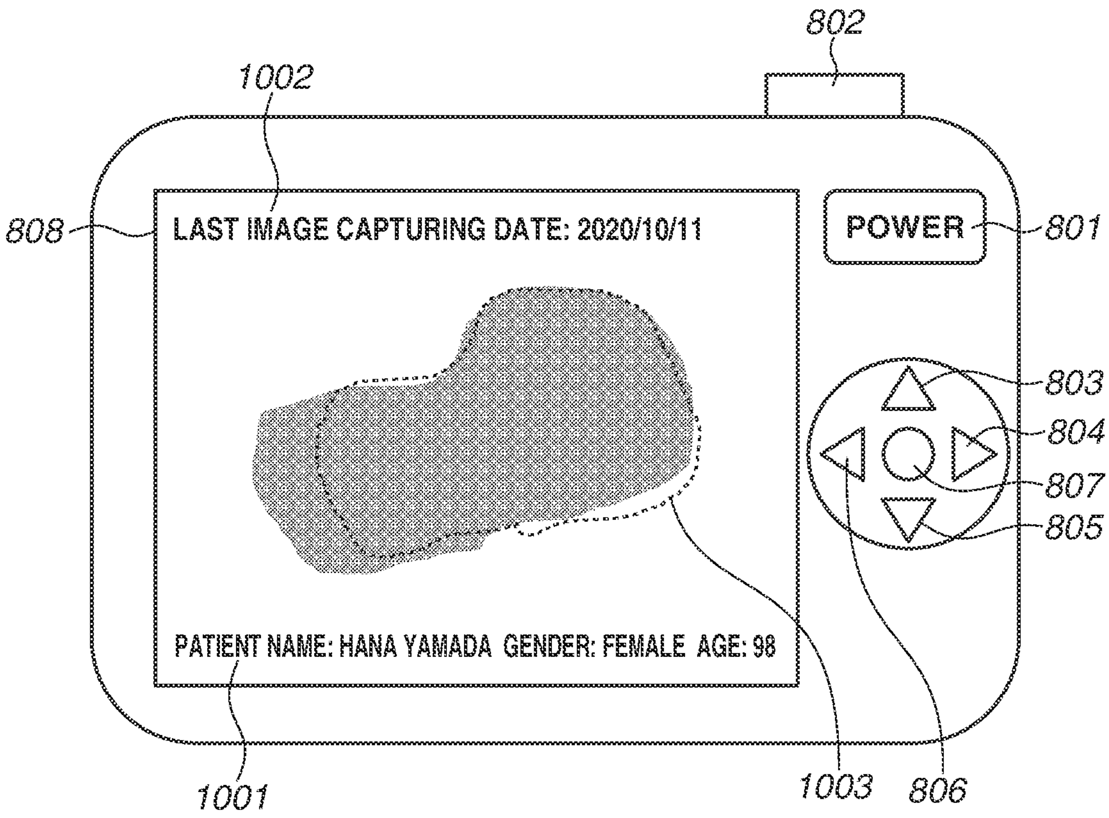
FIG. 10 is a diagram illustrating a state in which the digital still camera is viewed from the back side.

FIG. 10 is a diagram illustrating a state in which a digital still camera operating as an imaging apparatus according to an exemplary embodiment of the present invention is viewed from the back side. FIG. 10 illustrates an example in which an image capturing assisting graphic is drawn in a case where the examination purpose is pressure sore.

Information 1001 indicates an example of a patient information display, and displays the name, gender, and age of a patient. To prevent the operator from misidentifying the patient, at the time of image capturing, the patient information display is displayed in a superimposed manner on a subject image.

Information 1002 indicates a date of last image capturing.

Information 1003 indicates an outline of an affected part in the last image capturing. The drawing is performed so that easily-comparable image data can be obtained in a case where a medical examination of the same region of the same patient is performed.

Pieces of information 1001 to 1003 are included in the patient information received from the image processing apparatus 106 in step S601.

Figure 11:
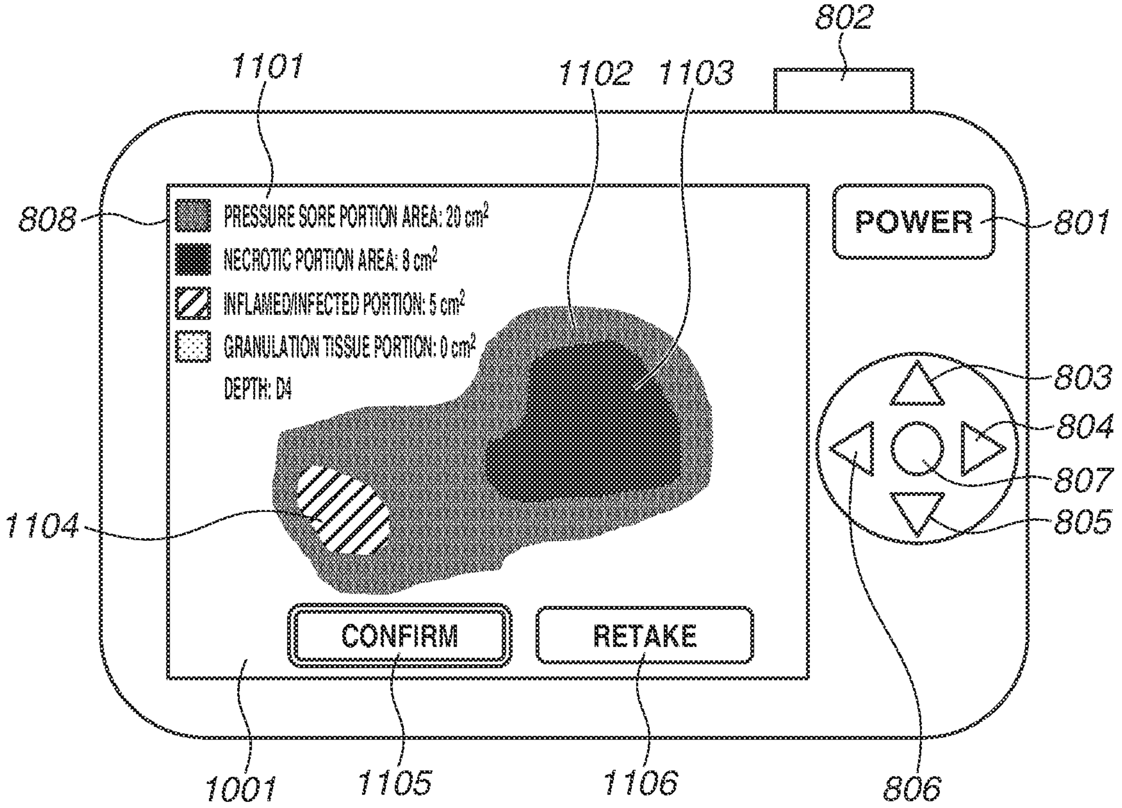
FIG. 11 is a diagram illustrating a state in which the digital still camera is viewed from the back side.

FIG. 11 is a diagram illustrating a state in which a digital still camera operating as an imaging apparatus according to an exemplary embodiment of the present invention is viewed from the back side. FIG. 11 illustrates an example of an inference result display screen to be displayed in a case where an examination purpose is pressure sore.

An example 1101 is a display example of a numerically-converted inference result. A result obtained by calculating areas of a pressure sore portion, a necrotic portion, an inflamed/infected portion, and a granulation tissue portion in pressure sore are displayed. As area calculation, the image processing apparatus 106 calculates correspondence between a distance on an image and a distance in a real world from a subject distance and a field angle in image capturing using a trigonometric function, and an area is calculated from the number of pixels included in the image.

An example 1102 is an example in which the pressure sore portion is colored and superimposed on the image.

An example 1103 is an example in which the necrotic portion is colored and superimposed on the image.

An example 1104 is an example in which the inflamed/infected portion is colored and superimposed on the image.

A confirm button 1105 is a confirm button. In a case where the confirm button 1105 has been selected by operating the left button 806, and then the operator has pressed the determination button 807, the CPU 201 determines that the confirm button has been selected by the operator.

A retake button 1106 is a retake button. In a case where the retake button 1106 has been selected by operating the right button 804, and then the operator has pressed the determination button 807, the CPU 201 determines that the retake button has been selected by the operator. The selection operation corresponds to the processing in steps S421 and S625.

Figure 12:
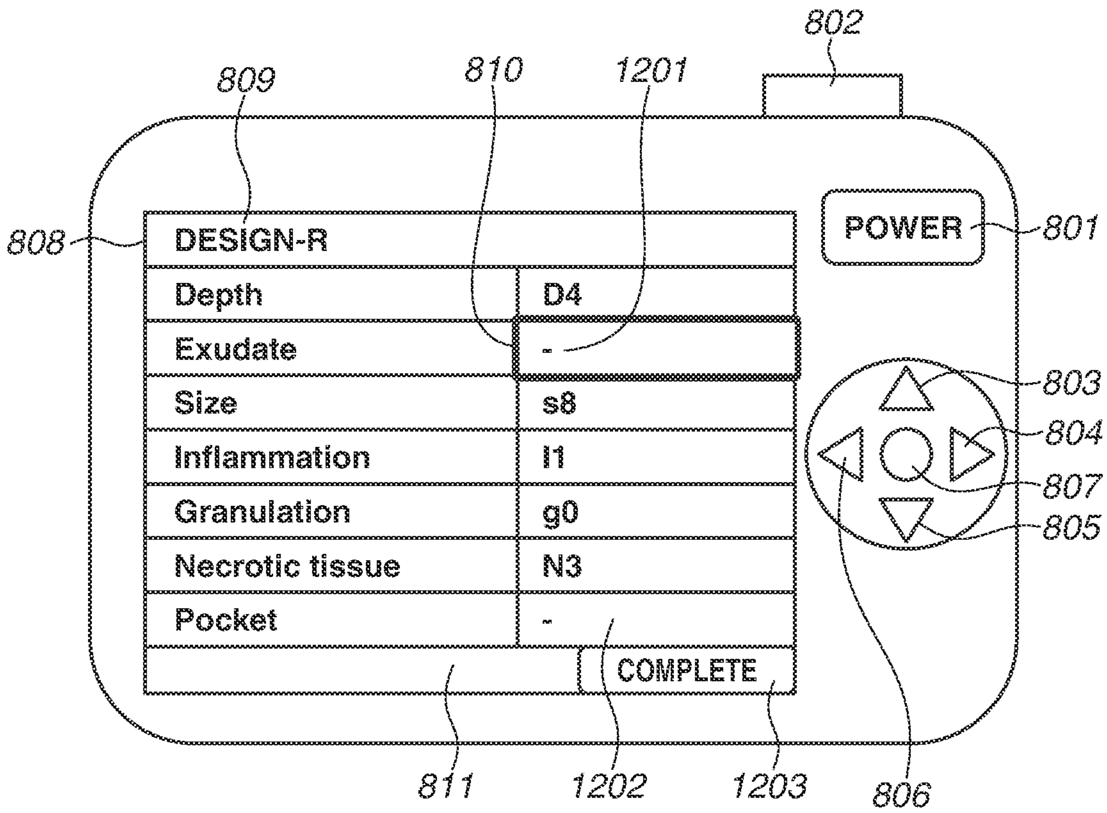
FIG. 12 is a diagram illustrating a state in which the digital still camera is viewed from the back side.

FIG. 12 is a diagram illustrating a state in which a digital still camera operating as an imaging apparatus according to an exemplary embodiment of the present invention is viewed from the back side. FIG. 12 illustrates an example of an evaluation value edit screen to be displayed in a case where an examination purpose is pressure sore.

Examples 1201 and 1202 are display examples of evaluation values that have not been calculated from inference. Even if an evaluation value has not been acquired by inference executed based on image data, by observing an affected part, an evaluation value to be recorded at the same time can be instantly entered. In addition, in a case where the operator has determined, by observing an affected part, that an evaluation value acquired by inference is to be changed, the operator performs an operation of changing the evaluation value. If the operator sets the focus frame 810 to the evaluation value to be changed using the up, down, left, and right buttons 803, 804, 805, and 806, and presses the determination button 807, the CPU 201 determines that an evaluation value change operation has been performed by the operator, and displays evaluation value candidates. Then, if the operator moves the focus frame 810 using the up or down button 803 or 805, and presses the determination button 807, the CPU 201 determines that an evaluation value selection operation has been performed. Then, the CPU 201 updates the display to the selected evaluation value, and stores the selected evaluation value in the RAM 203.

A complete button 1203 is a complete button. In a case where the complete button 1203 has been selected by operating the down button 805, and then the operator has pressed the determination button 807, the CPU 201 determines that the complete button has been selected by the operator. The selection operation corresponds to the processing in steps S423 and S628.

In the present exemplary embodiment, it has been described that, in step S634, the evaluation values are transmitted to the image processing apparatus 106 together with the image ID and the patient management number. Nevertheless, in a case where an affected part image on which the evaluation value is based is stored in the RAM 203 or the media drive 206 of the imaging apparatus 101, the evaluation value may be transmitted to the image processing apparatus 106 together with image data by writing the evaluation value as header information of the image. Accordingly, the evaluation value can be held as additional information of the image without associating an image ID with a targeted image after the image processing apparatus 106 receives the evaluation value and the image ID.

In the present exemplary embodiment, the description has been given of an example in which the examination purpose selection screen of the imaging apparatus is not displayed when the number of examination purposes associated with a patient is one, but all examination purposes may be always displayed as candidates, or examination purpose candidates may be set on the image processing apparatus depending on a clinical department that manages the imaging apparatus. If a configuration of displaying all the examination purposes as candidates and selecting an examination purpose on the imaging apparatus is employed, various examinations can be simultaneously executed on one patient. In addition, if a configuration in which the image processing apparatus selects an examination purpose and the imaging apparatus receives the selected examination purpose is employed, and an examination purpose is set on the image processing apparatus, it is possible to prevent the operator from selecting a wrong examination purpose.

In the present exemplary embodiment, it has been described that, if a disease set as the examination purpose is pressure sore, the DESIGN-R (registered trademark) is used as an evaluation item, and if a disease set as the examination purpose is asteatosis cutis, the specified symptom sum score system with grading of scaling, roughness, redness and cracks (hereinafter, abbreviated as SRRC) is used as an evaluation item. It has been described that, if a disease set as the examination purpose is atopic dermatitis, the Eczema Area and Severity Index (hereinafter, abbreviated as EASI) is used as an evaluation item. It has been described that, if a disease set as the examination purpose is psora, the Psoriasis Area Severity Index (hereinafter, abbreviated as PASI) is used as an evaluation item. It has been described that, if a disease set as the examination purpose is burn injury, the Total Body Surface Area (hereinafter, abbreviated as TBSA) and a burn depth are used as an evaluation item. Nevertheless, in a case where the evaluation item and the evaluation value vary depending on the country or the area, the evaluation item column 507 and the evaluation value column 508 in the image capturing control information illustrated in FIG. 5 may be changed. Accordingly, a new evaluation item and evaluation value can be dealt with without altering a program in the imaging apparatus.

As described above, with the imaging apparatus of the present exemplary embodiment, since image capturing control information is received from the image processing apparatus depending on an examination purpose, and an image capturing condition, screen display content, and image additional information are changed, even if a new examination purpose is added, the new examination purpose may be added to the image capturing control information illustrated in FIG. 5. Accordingly, the new examination purpose can be dealt with without altering a program in the imaging apparatus.

As described above, with the imaging apparatus of the present exemplary embodiment, it is determined whether or not the examination purpose can be confirmed from a captured image, and the operator is notified of a determination result. The operator can accordingly confirm whether an appropriate image has been captured. Furthermore, since the operator is notified of an issue in the image capturing, it becomes possible to record stable image data irrespective of a skill level of the operator.

In the present exemplary embodiment, the description has been provided of the example in which, with regard to the pressure sore, an inference result includes the area of an affected part, the pressure sore portion, the necrotic portion, the inflamed/infected portion, the granulation tissue portion, and the depth information as described with reference to FIG. 11. As for other examination purposes, as illustrated in the inference result display column 506 in FIG. 5, an inference result obtained by the image processing apparatus may be displayed. If the examination purpose is asteatosis cutis, an area of an affected part, an asteatosis cutis portion, an area of an affected part, skin roughness, skin redness, a skin cracks and fissures portion are displayed. If the examination purpose is atopic dermatitis, an area of an affected part, an erythematous portion, an erosion/papular portion, a scratched portion, and a lichenified portion are displayed. If the examination purpose is psora, an area of an affected part, an erythematous portion, an erosion portion, and a desquamated portion are displayed. If the examination purpose is burn injury, an area of an affected part, a burn portion, and a burn depth are displayed. If the examination purpose is hives, an area of an affected part, a wheal portion, and the number of hives are displayed. In addition, in a case where the examination purpose is teeth, i.e., a disease in the oral cavity, the type of teeth, the presence or absence of teeth, the presence or absence of a prosthetic appliance, the presence or absence of tooth decay, a tooth decay portion, and a periodontal disease portion may be displayed on the imaging apparatus. Furthermore, if it becomes possible to acquire information useful for disease evaluation due to inference performance improvement in the image processing apparatus, the information may be added. In a case where it is difficult to merge all inference results on the inference result display screen of the imaging apparatus, an image expected to be displayed on the imaging apparatus may be generated by the image processing apparatus and transmitted.

As described above, with the system including the imaging apparatus and the image processing apparatus of the present exemplary embodiment, based on the image capturing control information, a captured image is transmitted to the image processing apparatus, the image processing apparatus performs inference execution, and the imaging apparatus receives an inference result. Thus, even in a case where the performance of inference or an image processing algorithm improves along with the performance improvement of a learning model of machine learning, an inference algorithm, or an image processing algorithm, a benefit of performance improvement can be enjoyed without altering a program in the imaging apparatus. Moreover, in a case where it is difficult to merge inference results on the imaging apparatus, it becomes possible to generate a merged image on the image processing apparatus, transmit the merged image, and display the received image on the imaging apparatus.

As described above, with the imaging apparatus of the present exemplary embodiment, based on the image capturing control information, an examination evaluation item is changed to an examination evaluation item suitable for the examination purpose. Then, an evaluation value of the examination evaluation item is stored while being attached to an image. With this configuration, it is possible to instantly record the evaluation value corresponding to the examination purpose. It is therefore possible to prevent an omission in recording from occurring. In addition, also in a case where an inference result obtained by the image processing apparatus is inappropriate, the inference result can be instantly corrected easily.

As described above, with the imaging apparatus of the present exemplary embodiment, image capturing is executed under an image capturing condition suitable for the examination purpose based on the image capturing control information. It therefore becomes possible to record stable image data irrespective of the skill level of the operator.

As described above, with the imaging apparatus of the present exemplary embodiment, region candidates are changed depending on the selection of on or off of the total body flag, and in a case where the total body flag is set to on, regions to be displayed as the region candidates are increased in size, and in a case where the total body flag is set to off, regions to be displayed as the region candidates are decreased in size. In other words, the granularity of region information is changed depending on whether or not a disease set as the examination purpose is to be diagnosed based on a percentage in the total body of the patient. In a case where the examination purpose is an examination purpose for which a disease state is evaluated from the symptom throughout the total body, the operator is prompted to execute image capturing of a plurality of regions, but by enhancing the granularity, it is possible to reduce the number of times the image capturing is executed to capture the image of the total body. In addition, it is possible to prevent the operator from forgetting to capture an image of a region candidate, and calculate an evaluation value of the disease for the total body.

In the present exemplary embodiment, drawing an outline of an affected part in the last image capturing as the image capturing assisting graphic has been described as an example, but an outline corresponding to a body region may be displayed depending on the examination purpose, the total body flag, and an image capturing target region. For example, if the image capturing target region is set to a body trunk for a disease to be diagnosed based on the percentage of the symptom throughout the total body, outlines of a shoulder and a torso may be displayed. If the image capturing target region is a head/neck, an outline of a head extending to a neck may be displayed. If the image capturing target region is an upper extremity, an outline of an upper extremity may be displayed. If the image capturing target region is a lower extremity, an outline of a lower extremity is displayed.

As described above, with the imaging apparatus of the present exemplary embodiment, based the image capturing control information, an image capturing assisting graphic suitable for the examination purpose is displayed in a superimposed manner on a live view image. It therefore becomes possible to record stable image data based on which comparison can be easily made even if an operator or an image capturing date varies.

As described above, with the imaging apparatus of the present exemplary embodiment, the examination purpose, patient information, image data, an inference result, and an evaluation value are transmitted to the image management system in association with each other. Thus, it becomes easier to execute follow-up of a patient for each examination purpose, and by displaying the examination purpose, region selection, and an assisting graphic at the time of the next image capturing, it becomes easier to perform a selection operation and an image capturing operation in the imaging apparatus.

As described above, with the imaging apparatus of the present exemplary embodiment, the image capturing control information includes information indicating whether or not image capturing is required for each examination purpose and each region. Then, as for a region of which image-capturing is required, in a case where a region of which image capturing has not been executed remains, the operator is notified thereof. It therefore becomes possible to prevent the operator from forgetting to capture an image of a region of which image-capturing is required.

As described above, with the imaging apparatus of the present exemplary embodiment, even in a case where a condition, such as a relative position between the imaging apparatus and a subject and a light source in an image capturing environment, cannot be controlled, appropriate image capturing, image processing, and examination item recording that are suitable for the examination purpose can be executed.

Second Exemplary Embodiment

In the present exemplary embodiment, description will be provided using, as an example, a medical examination of teeth to be diagnosed on an image processing apparatus based on a plurality of captured images of a plurality of affected parts.

First, image capturing control processing to be executed in a case where the examination purpose is teeth will be described with reference to FIG. 6. The description will be mainly provided of image capturing control processing specific to the medical examination of teeth, and in a case where the processing is the same as the processing for other examination purposes, the description will be omitted.

In step S605, the CPU 201 transmits the examination purpose which is teeth to the image processing apparatus 106.

In step S606, the CPU 201 receives the image capturing control information from the image processing apparatus 106 and stores the received image capturing control information in the RAM 203. In a case where the examination purpose is teeth, the CPU 201 receives information in the row 517 for a medical examination of teeth as the image capturing control information.

In step S607, the CPU 201 refers to information in the column 510 in the image capturing control information, and determines whether or not image capturing of multiple regions is required. As in the image capturing control information in the row 517 for a medical examination of teeth, since the image capturing of multiple regions is required, the processing proceeds to step S609.

In step S610, the CPU 201 refers to information in the column 509 in the image capturing control information, and determines whether or not determination based on multiple images is executable. As in the image capturing control information in the row 517 for a medical examination of teeth, since the determination based on multiple images is to be executed, the processing proceeds to step S611.

In step S611, the CPU 201 displays a screen for prompting the operator to select whether or not to make evaluation based on a systemic symptom, and determines whether or not the operator has performed an operation of selecting the evaluation based on a systemic symptom. Since determination is not made based on a systemic symptom in the case of a medical examination of teeth, the processing proceeds to step S613.

Figure 13:
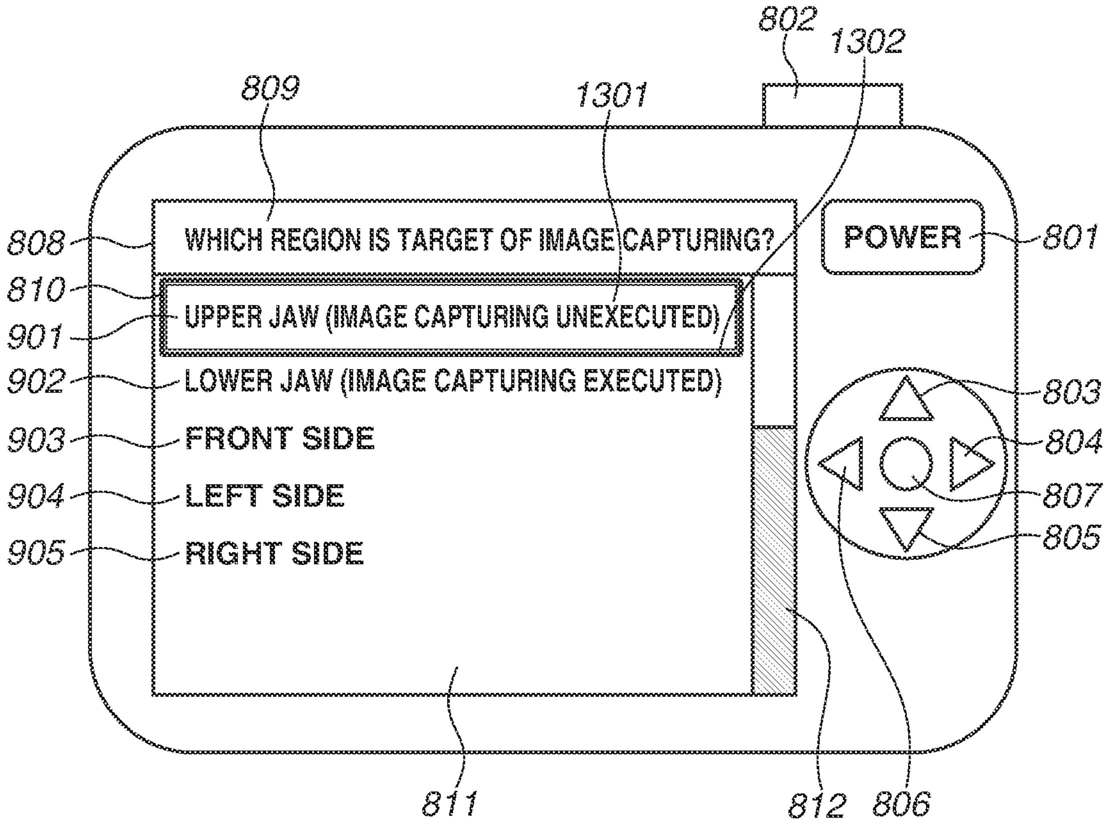
FIG. 13 is a diagram illustrating a state in which the digital still camera is viewed from the back side.

In step S614, the CPU 201 refers to information on the column 503 in the image capturing control information, and displays region candidates on the region selection screen. As in the image capturing control information in the row 517 for a medical examination of teeth, an upper jaw, a lower jaw, a front side, a left side, and a right side are listed. FIG. 13 illustrates an example of a region selection screen to be displayed in the case of a medical examination of teeth. The description of FIG. 13 will be provided below.

In step S616, the CPU 201 refers to information in the image capturing condition column 502 in the image capturing control information, and controls the imaging unit 200 in such a manner that image capturing can be executed with a parameter satisfying an image capturing condition. As in the image capturing control information in the row 517 for a medical examination of teeth, a focus position, a zoom position, an exposure, an ISO, a Tv value, an Av value, WB, and electronic flash are set. The focus position is set to a position on an image plane of teeth selected in region selection. In a case where the upper jaw is selected, the focus position is set to a position of a dental arch in a convex direction. In a case where a lower jaw is selected, the focus position is set to a position of a dental arch in a concave direction. In a case where the front side, the left side, or the right side is selected, the focus position is set to the center position.

Figure 14:
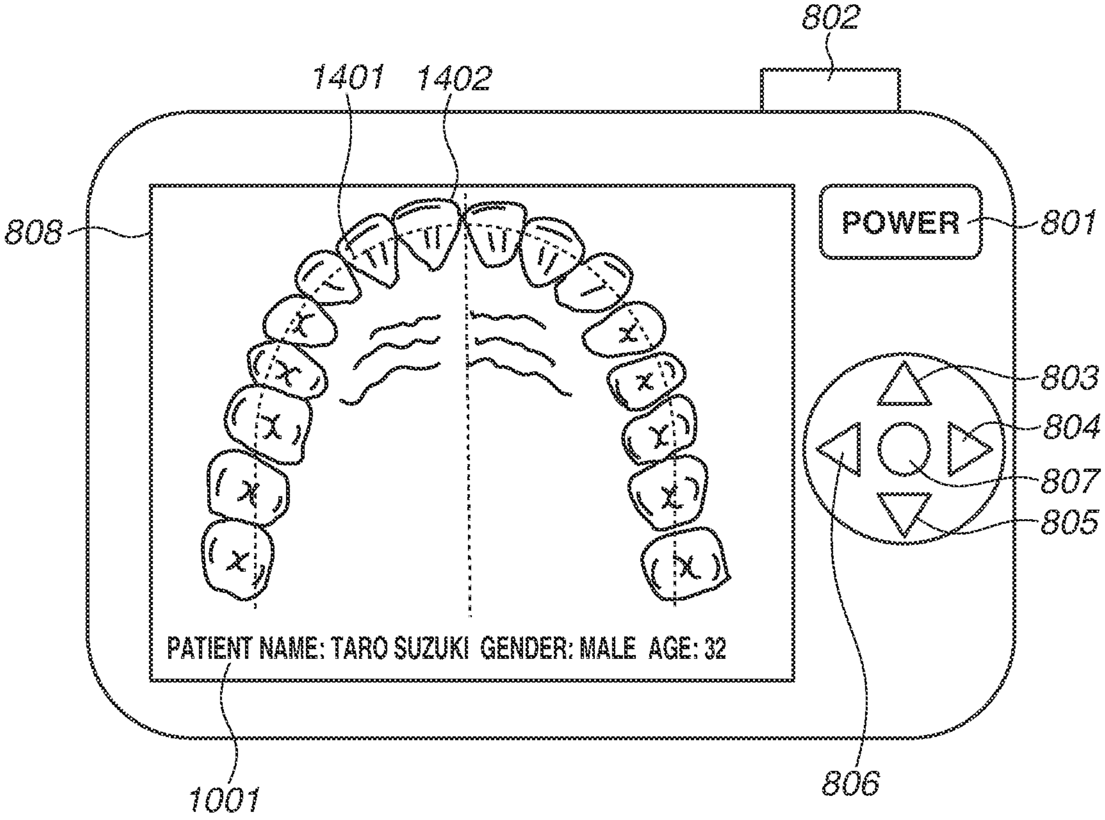
FIG. 14 is a diagram illustrating a state in which the digital still camera is viewed from the back side.

In step S617, the CPU 201 refers to information in the assisting graphic column 504 in the image capturing control information, and draws an image capturing assisting graphic in a superimposed manner on a formed subject image. As in the image capturing control information in the row 517 for a medical examination of teeth, in the case of the upper jaw or the lower jaw, the CPU 201 draws an outline of the dental arch and a vertical line passing through the center. In the case of the front side, the left side, or the right side, the CPU 201 draws the vertical line passing through the center and a horizontal line. FIG. 14 illustrates an example of an image capturing assisting screen in the case of the medical examination of teeth. The description of FIG. 14 will be provided below.

In step S620, the CPU 201 refers to information in the confirmation condition column 505 in the image capturing control information, and determines whether or not image data suitable for the examination purpose has been generated. As in the image capturing control information in the row 517 for a medical examination of teeth, the determination is made. The confirmation processing executed in step S620 will be described below with reference to FIG. 15.

In step S621, the CPU 201 refers to information in the column 506 indicating whether to display an inference result in the image capturing control information, and determines whether or not to display an inference result on the display device 204 of the imaging apparatus 101. As in the image capturing control information in the row 517 for a medical examination of teeth, an inference result is not to be displayed. Thus, the processing proceeds to step S626.

In step S626, the CPU 201 refers to the evaluation item column 507 in the image capturing control information, and determines whether or not an evaluation value to be edited on the imaging apparatus 101 is included. As in the image capturing control information in the row 517 for a medical examination of teeth, "N/A" is set. Thus, the processing proceeds to step S629.

In step S629, the CPU 201 stores an image-captured region in the RAM 203.

In step S630, the CPU 201 determines whether or not the total body flag or the multiple region flag is set to on. In the case of a medical examination of teeth, the multiple region flag is set to on as described above. Thus, the processing proceeds to step S631.

In step S631, the CPU 201 refers to the column 510 indicating whether image capturing of multiple regions is required in the image capturing control information, checks the multiple regions against the image-captured region stored in the RAM 203 in step S629, and determines whether or not a region of which image capturing has not been executed remains. As in the image capturing control information on the row 517 for a medical examination of teeth, since the upper jaw and the lower jaw are required, the CPU 201 checks the multiple regions against the image-captured region stored in the RAM 203, and in a case where it is determined that a region of which image capturing has not been executed remains, the processing returns to step S614. In a case where it is determined that a region of which image capturing has not been executed is not left, the processing proceeds to step S632.

In step S632, the CPU 201 determines whether or not the total body flag is set to on. In the case of a medical examination of teeth, the total body flag is set to off as described above. Thus, the processing proceeds to step S634.

In step S634, the CPU 201 transmits the evaluation value selected in step S627 and the evaluation value calculated in step S633 to the image processing apparatus 106 together with the image ID. In a case where there is no evaluation value, the CPU 201 transmits unsent image data to the image processing apparatus 106 together with an image capturing condition used during the image capturing, an examination purpose, and a patient management number. In the case of a medical examination of teeth, since there is no evaluation value, the CPU 201 transmits unsent image data to the image processing apparatus 106 together with an image capturing condition used during the image capturing, an examination purpose, and a patient management number.

FIG. 13 is a diagram illustrating a state in which a digital still camera operating as an imaging apparatus according to an exemplary embodiment of the present invention is viewed from the back side. FIG. 13 illustrates an example of a region selection screen to be displayed in a case where an examination purpose is teeth. The members fulfilling the same functions as those illustrated in FIGS. 8 and 9 are assigned the same numerals as those illustrated in FIGS. 8 and 9.

States 1301 and 1302 both indicate image capturing states.

The state 1301 indicates that image capturing of a region 901 of a target patient has not been executed.

The state 1302 indicates that image capturing of a region 902 of the target patient has been executed.

Whether or not the image capturing has been executed is determined based on whether or not the CPU 201 has stored a region in the RAM 203 as an image-captured region. As for image-captured regions, information indicating that image capturing has been executed is desirably displayed for all regions. On the other hand, as for regions of which image capturing has not been executed, information indicating that image capturing has not been executed may be displayed for only a region required to be image-captured.

FIG. 14 is a diagram illustrating a state in which a digital still camera operating as an imaging apparatus according to an exemplary embodiment of the present invention is viewed from the back side. FIG. 14 illustrates an example in which image capturing assisting graphics are drawn in a case where an examination purpose is teeth, and in a case where an image capturing target region is an upper jaw. The members fulfilling the same functions as those illustrated in FIGS. 8 and 10 are assigned the same numerals as those illustrated in FIGS. 8 and 10.

Information 1001 indicates an example of the patient information display, and displays the name, gender, and age of a patient. To prevent the operator from misidentifying the patient, at the time of image capturing, the patient information display is displayed in a superimposed manner on a subject image.

An outline 1401 is an outline of a dental arch. In a case where an image capturing target region is an upper jaw, a graphic of a convex direction arch is drawn. In a case where an image capturing target region is a lower jaw, a graphic of a concave direction arch is drawn.

A vertical line 1402 is a vertical line passing through a center point of a field angle corresponding to a subject image.

By capturing an image of an affected part with reference to image capturing assisting graphics indicated by the outline 1401 and the vertical line 1402, any operator can capture an image at a similar position irrespective of the skill level of the operator.

Captured Image Confirmation Processing

Figure 15:
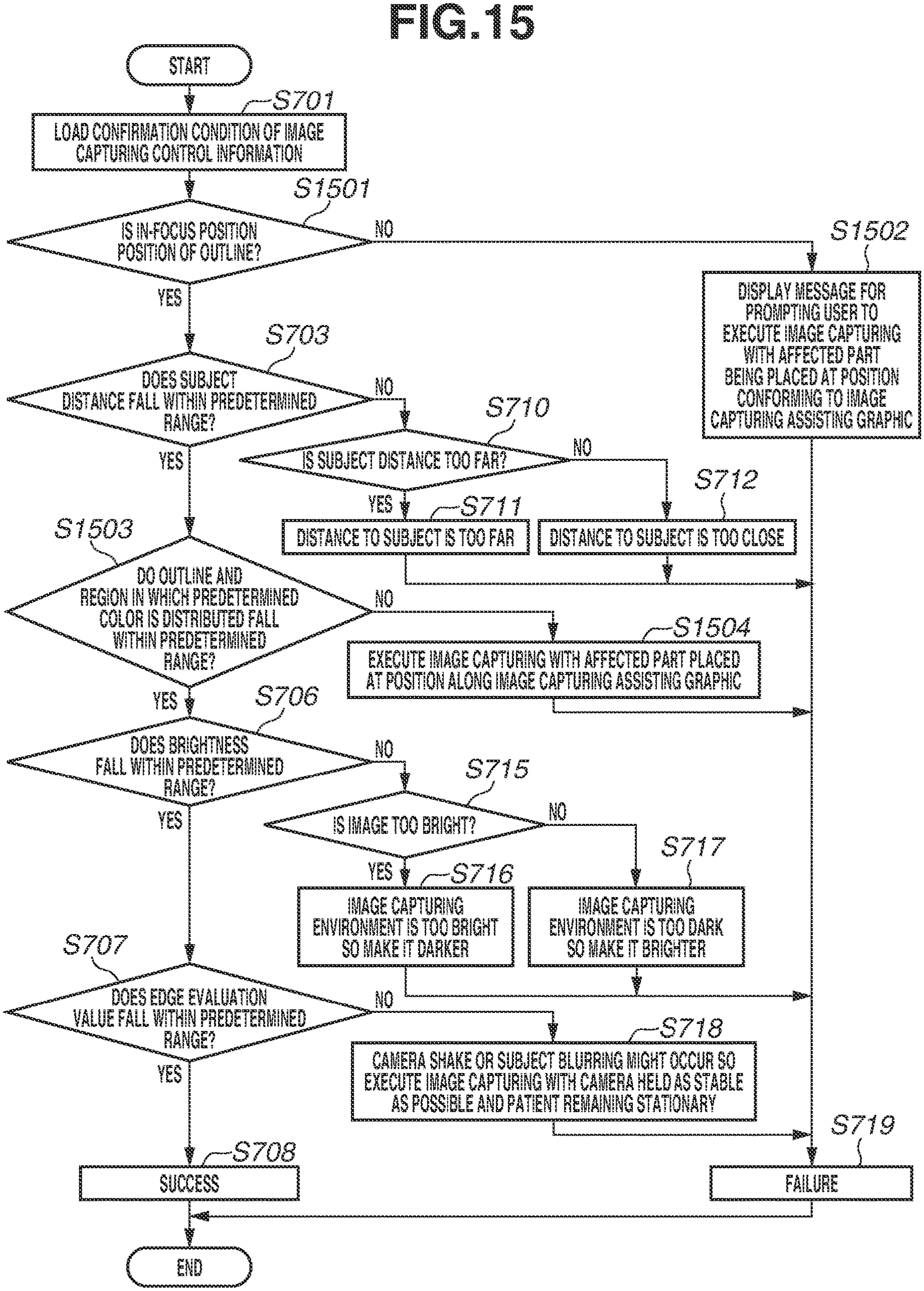
FIG. 15 is a flowchart illustrating captured image confirmation processing.

FIG. 15 is a flowchart illustrating captured image confirmation processing according to the present exemplary embodiment. By the processing, whether an image suitable for an examination purpose has been generated is confirmed. The above-described processing in step S620 will be described in detail. The description will be provided of an example where the examination purpose is teeth, and the image capturing target region is an upper jaw. Processes similar to the processes in FIG. 7 are assigned the same numbers as those in FIG. 7, and descriptions will be omitted.

In step S1501, the CPU 201 determines whether an in-focus position in image capturing is near a coordinate of an outline of an image capturing assisting graphic in the image. The in-focus position in the image is held in header information added to the image data as coordinate information. If the in-focus position falls within a predetermined range from the coordinate of the outline in the image, it is determined that the in-focus position is near the coordinate of the outline, and the processing proceeds to step S703. In a case where it is determined that the in-focus position is not near the coordinate of the outline, the processing proceeds to step S1502.

In step S1502, to notify the operator that the in-focus position is shifted from the position of teeth, the CPU 201 displays a message for prompting the operator to execute image capturing with an affected part placed at a position along the image capturing assisting graphic, on the display device 204.

In step S1503, the CPU 201 determines whether or not a region in which a predetermined color is distributed is distributed near the coordinate of the outline of the image capturing assisting graphic. In the case of teeth, the predetermined color is white. In the case of a prosthetic appliance or an orthotic, the predetermined color is silver or gold. In a case where it is determined that the region is distributed near the coordinate of the outline, the processing proceeds to step S706. In a case where it is determined that the region is not distributed near the coordinate of the outline, the processing proceeds to step S1504.

In step S1504, to notify the operator that image capturing of teeth has failed to be executed along the outline, the CPU 201 displays a message for prompting the operator to execute image capturing with an affected part placed at a position along the image capturing assisting graphic, on the display device 204.

Figure 16:
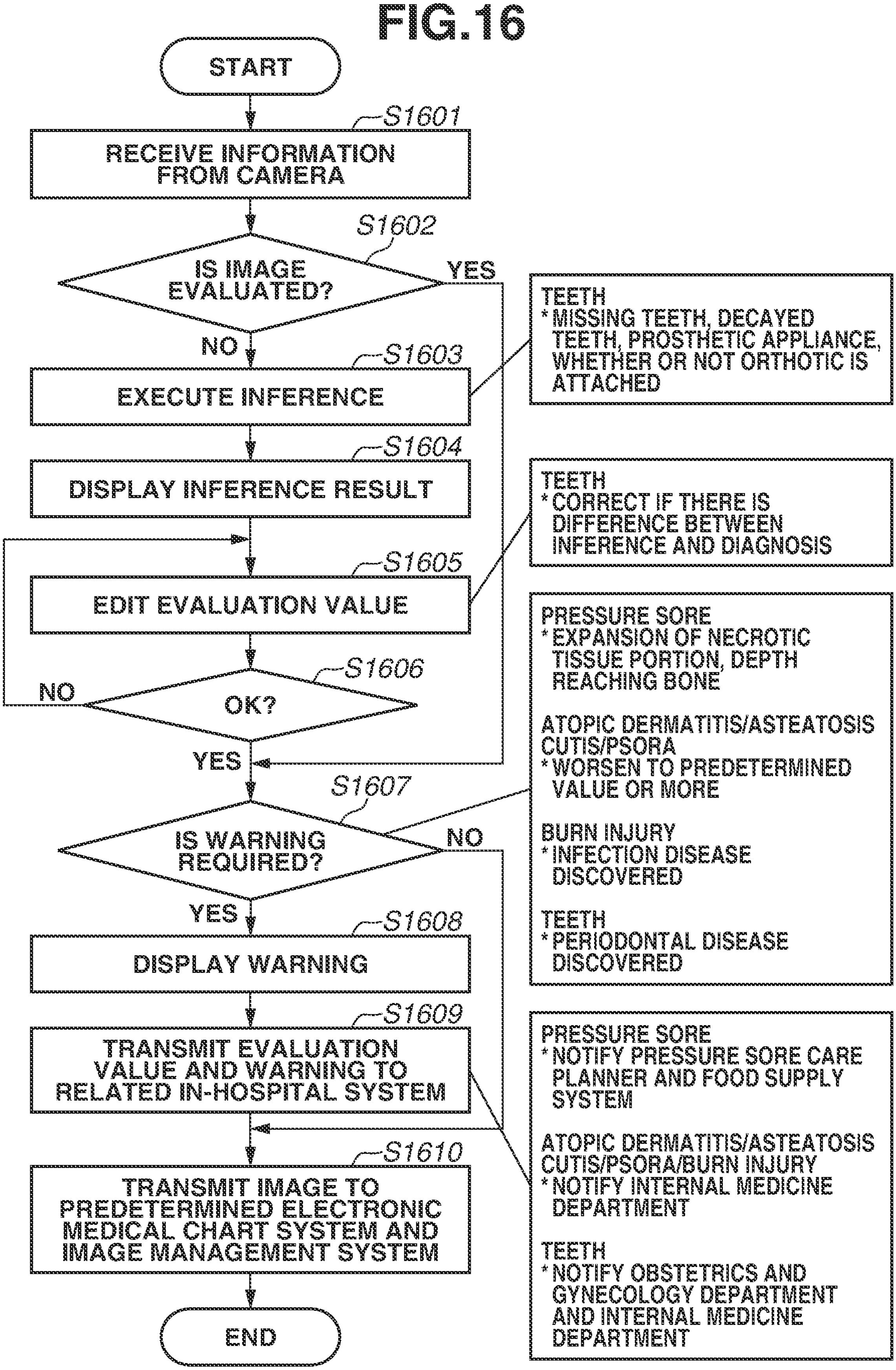
FIG. 16 is a flowchart illustrating inference execution processing in an image processing apparatus.

FIG. 16 is a flowchart illustrating inference execution processing in the image processing apparatus according to the present exemplary embodiment. In step S634 of FIG. 6, the imaging apparatus 101 transmits a result such as the evaluation value, or the image data to the image processing apparatus 106. After that, the image processing apparatus 106 executes the inference execution processing illustrated in FIG. 16.

In step S634, the CPU 201 transmits the evaluation value selected in step S627 and the evaluation value calculated in step S633 to the image processing apparatus 106 together with the image ID and the patient management number. In a case where there is no evaluation value, the CPU 201 transmits unsent image data to the image processing apparatus 106 together with the patient management number.

In step S1601, the CPU 301 receives an evaluation value, an image ID, and a patient management number, or image data and a patient management number.

In step S1602, the CPU 301 determines whether or not an image has been evaluated for an examination purpose. Whether or not the image has been evaluated is determined based on whether or not any evaluation value has been received in step S1601. In a case where it is determined that the image has not been evaluated, the processing proceeds to step S1603. In a case where it is determined that the image has been evaluated, the processing proceeds to step S1607.

In step S1603, the CPU 301 executes inference based on the examination purpose associated with the patient management number. The inference is similar to the inference in step S418. In a case where inference is executed using a plurality of images, and different inference results are output for the same region, an inference result with a higher numerical value of probability may be employed, or a result indicating a severer symptom may be employed.

In step S1604, the CPU 301 displays an inference result based on the examination purpose. In a case where the examination purpose is teeth, at the position of each teeth in a figure indicating a dental formula, an inference result such as a healthy tooth, a decayed tooth, a metal prosthetic appliance, a white prosthetic appliance, a wedge-shaped defect (WSD), an implant, and whether or not an orthotic is attached is displayed in the form of a balloon. As for a periodontal disease, at the position of gums in the figure indicating the dental formula, an inference result of a periodontal disease is displayed in the form of a balloon. The type of tooth, such as a right canine tooth and a first molar tooth of the upper jaw, is not individually displayed, but by internally associating the type of tooth with a symptom indicated by an inference result, on a figure indicating the dental formula, the symptom is displayed as a balloon for each teeth.

In step S1605, the CPU 301 shifts the screen to a screen for editing an evaluation value. The screen may transition to a screen that fulfills the function of the evaluation value edit screen of the imaging apparatus 101, or the balloon displayed as an inference result in step S1604 may be made selectable and the user may change the evaluation value using the input device 306. Then, an edit completion button is arranged within the screen.

In step S1606, the CPU 301 determines whether or not the edit completion button has been selected. In a case where it is determined that the edit completion button has been selected, the processing proceeds to step S1607. In a case where the edit completion button has not been selected, the processing returns to step S1605, and the CPU 301 continues to display the screen on which the evaluation value can be edited.

In step S1607, the CPU 301 selects whether or not a warning is required. Whether or not a warning is required is determined based on whether or not a condition preliminarily designated by the user for each examination purpose is satisfied. In addition, in a case where any other system or clinical department to be notified exists, the user also sets information regarding the system or clinical department, together with the warning. Although the information is to be used in the image processing apparatus, because the information is for each examination purpose, the information may be stored while being attached to the image capturing control information illustrated in FIG. 5. A condition and a notification destination that are set for each examination purpose are stored in the HDD 305. When the processing is executed, the condition and the notification destination are loaded into the RAM 303, and the CPU 301 makes determination. In a case where the condition designated by the user is not satisfied, the CPU 301 determines that a warning is required, and the processing proceeds to step S1608. In a case where the condition designated by the user is satisfied, the CPU 301 determines that a warning is not required, and the processing proceeds to step S1610. Examples of cases where a warning is required include a case where a necrotic tissue portion has expanded and a case where depth of pressure sore has reached a bone in a case where the examination purpose is pressure sore. In a case where the examination purpose is atopic dermatitis, asteatosis cutis, or psora, examples of the cases where a warning is required include a case where a percentage thereof with respect to an area of the entire body tends to expand, and a case where inflammation worsens to a predetermined value or more. In a case where the examination purpose is burn injury, examples of the cases where a warning is required include a case where an infection disease has been found. In a case where the examination purpose is teeth, examples of the cases where a warning is required include a case where a periodontal disease has been found.

In step S1608, the CPU 301 displays a warning.

In step S1609, the CPU 301 transmits the evaluation value and the warning to the notification destination set by the user, in association with the patient management number. Warning notification destinations may be, in a case where the examination purpose is pressure sore, a care plan management system of a pressure sore care planner and a food supply system. In a case where the examination purpose is atopic dermatitis, asteatosis cutis, psora, or burn injury, a warning notification destination may be a clinical department system of an internal medicine department. In a case where the examination purpose is teeth, warning notification destinations may be clinical department systems of an obstetrics and gynecology department and an internal medicine department.

In step S1610, in a case where there is image data, the CPU 301 transmits the image data to the predetermined electronic medical chart system 104 and the image management system 105.

In the present exemplary embodiment, the description has been provided of an example in which the inference result of teeth is displayed in the figure of the dental formula in the form of a balloon, but each tooth and a state may be paired and output in the form of a dental formula code.

In the present exemplary embodiment, the description has been provided of the example in which the inference result is displayed on the image processing apparatus, but communication may be further performed with the electronic medical chart system 104, and the inference result may be displayed on the electronic medical chart display terminal 103. In this case, after step S1603, the inference result may be transmitted to the electronic medical chart system 104, and the processing in steps S1605 to S1609 may be provided by the functions of the electronic medical chart system.

As described above, with the imaging apparatus of the present exemplary embodiment, whether or not to display an image analysis result is changed based on the image capturing control information. Thus, depending on the setting in the image capturing control information, the inference result can be displayed on the imaging apparatus or displayed on the image processing apparatus depending on the examination purpose.

As described above, with the imaging apparatus of the present exemplary embodiment, based on the image capturing control information, an image capturing assisting graphic changes depending on the examination purpose and the region. In the case of a medical examination of teeth in the present exemplary embodiment, when an image of the front side is captured, a straight line in a horizontal direction (traverse direction) for bite positions, and a straight line in a vertical direction (lengthwise direction) for a center position of teeth may be displayed. Image capturing can be executed in such a manner that bite positions of teeth are arranged along the horizontal line, and a center position of foreteeth are arranged along the vertical line. It therefore becomes possible to record stable image data based on which comparison can be easily made even if an operator or an image capturing day is different.

As described above, with the system including the imaging apparatus and the image processing apparatus of the present exemplary embodiment, whether or not a warning is required is switched depending on the examination purpose, and in a case where a warning is required, a notification is made. Furthermore, as necessary, a medical system of a related clinical department is also notified. With this configuration, it becomes possible to prevent the omission of treatment from occurring.

Third Exemplary Embodiment

In the present exemplary embodiment, a description will be provided of an example of executing more appropriate image capturing with regard to a disease with a symptom including a rash. As for the disease with a symptom including a rash, features of an affected part are minute and extensive in some cases. It is therefore desirable to capture, as a diagnosis image, a bird's-eye image for checking an overall picture in addition to an enlarged image for checking details. In view of the foregoing, the description will be provided of an example of a medical examination of atopic dermatitis to be diagnosed on the image processing apparatus based on an image captured at each field angle, by capturing images of an affected part at a plurality of field angles.

First, image capturing control processing to be executed in a case where the examination purpose is atopic dermatitis will be described with reference to FIGS. 17 and 18. The description will be mainly provided of image capturing control processing specific to the medical examination of atopic dermatitis, and in a case where the processing is the same as the processing for other examination purposes, the description will be omitted.

FIG. 17 is a conceptual diagram illustrating a correspondence relationship between image capturing control information and examination purposes according to the present exemplary embodiment. In the present exemplary embodiment, the information illustrated in FIG. 17 is stored in the HDD 305 in the image processing apparatus 106, and is information to be used when image capturing control information corresponding to the examination purpose received from the imaging apparatus 101 in step S411 is loaded in step S412. The information similar to the information illustrated in FIG. 5 is assigned the same reference numeral as that in FIG. 5, and the description will be omitted.

A column 1701 indicates an image capturing condition. An image capturing condition to be designated in the imaging apparatus 101 to capture an image appropriate for medical examination aid is held for each examination purpose. A parameter not designated in the image capturing condition is modifiable by the operator on the imaging apparatus 101. Unlike the column 502, to capture a bird's-eye image and an enlarged image, the zoom position is set to manual irrespective of the total body flag.

Figure 18A:
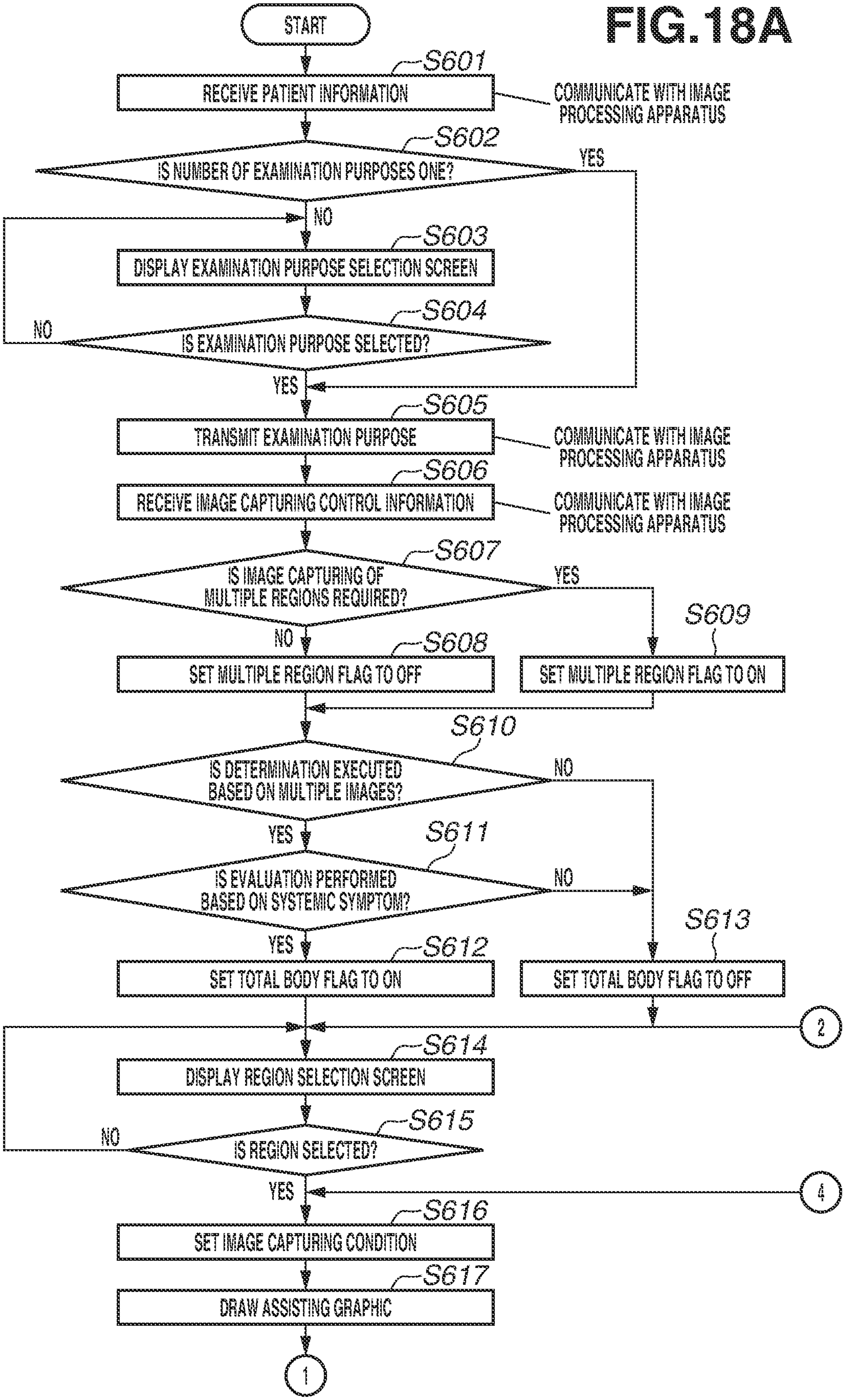
FIGS. 18A, 18B, and 18C, are flowcharts illustrating image capturing control processing.
Figure 18B:
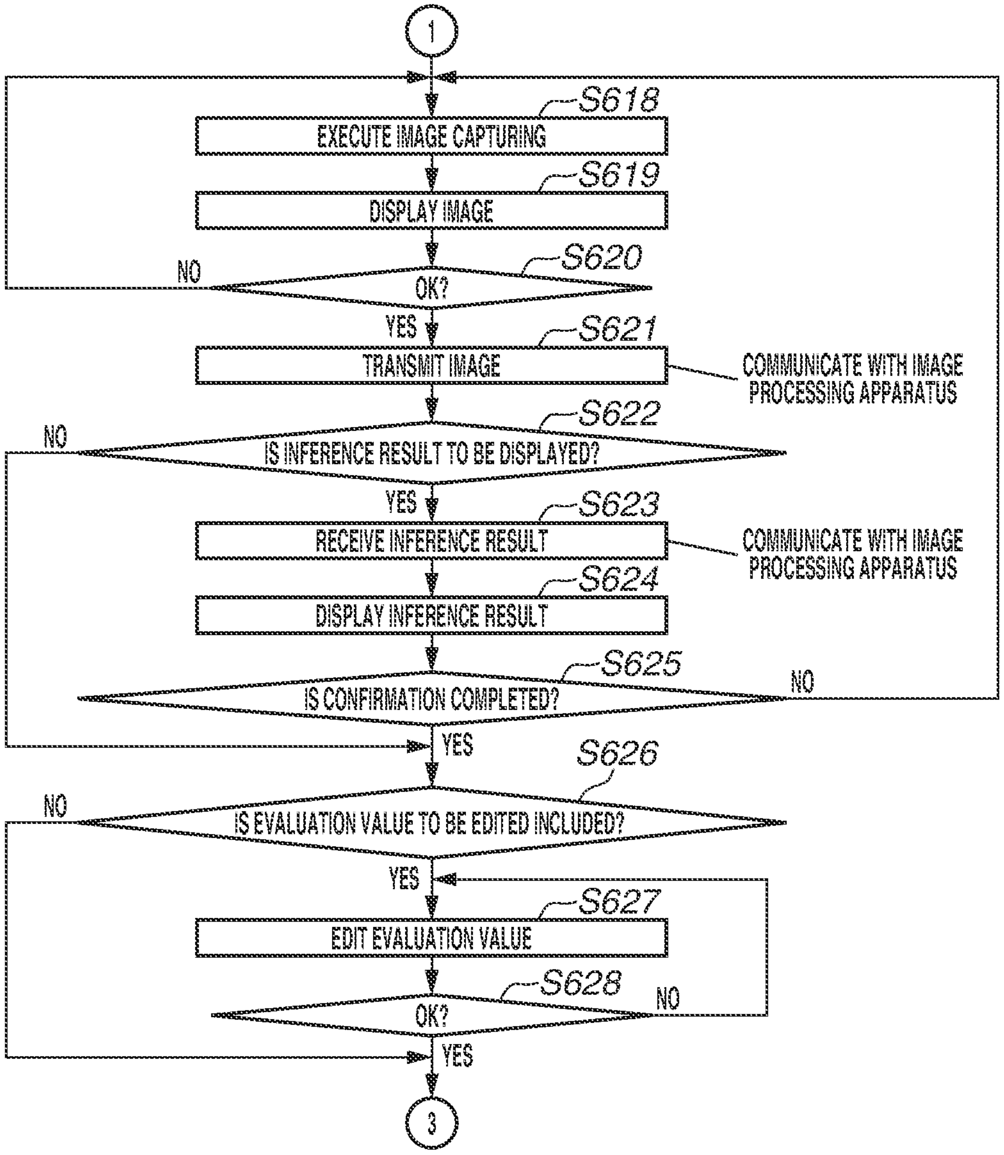
Figure 18C:
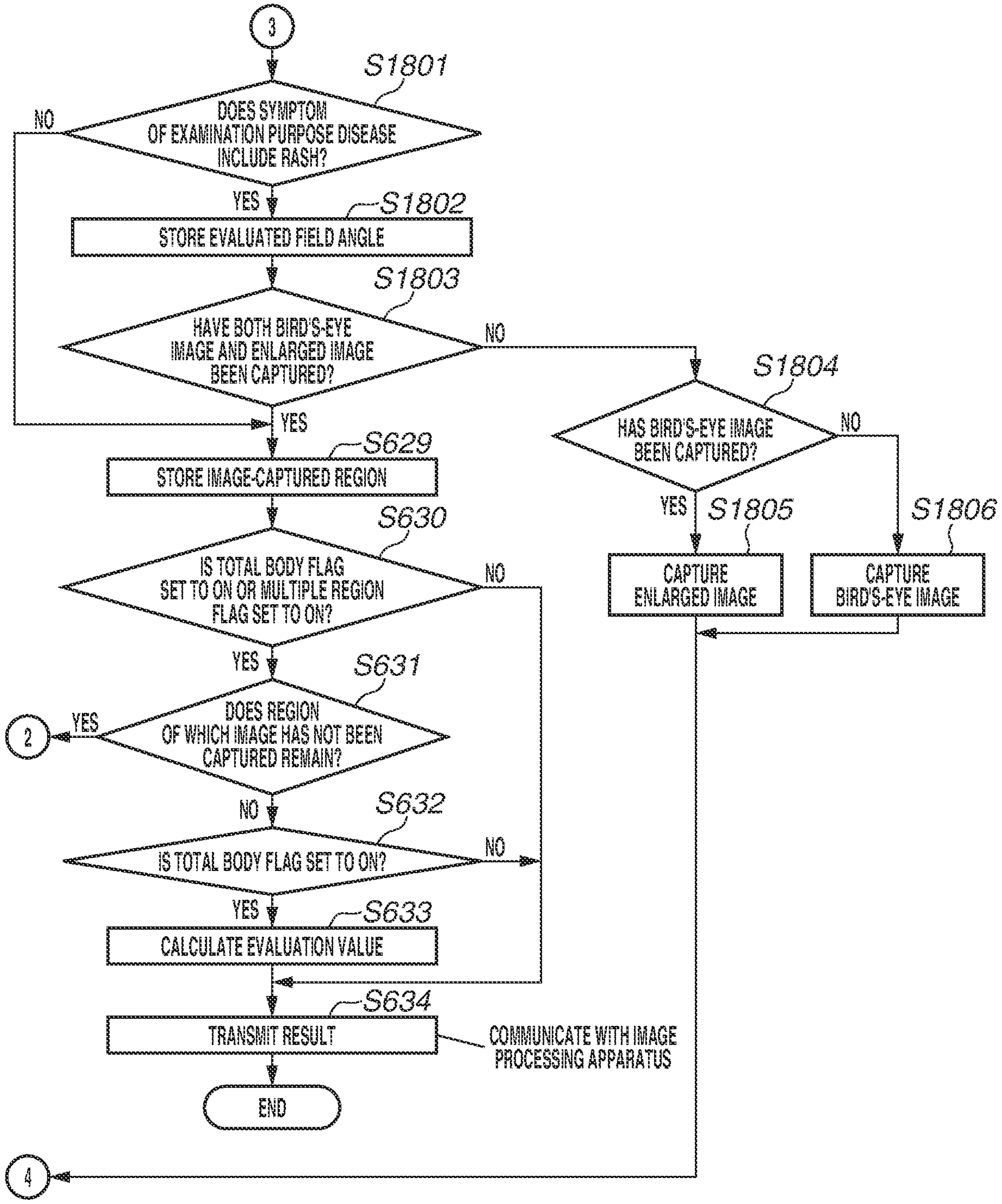

FIG. 18 is a flowchart illustrating image capturing control processing according to the present exemplary embodiment. Processing in the imaging apparatus 101 will be described in detail with reference to FIG. 18. Processes similar to the processes in FIG. 6 are assigned the same numbers as those in FIG. 6, and descriptions will be omitted except for processes specific to a medical examination of atopic dermatitis.

In step S605, the CPU 201 transmits atopic dermatitis to the image processing apparatus 106 as the examination purpose.

In step S606, the CPU 201 receives the image capturing control information from the image processing apparatus 106 and stores the received image capturing control information in the RAM 203. In a case where the examination purpose is atopic dermatitis, the CPU 201 receives information in the row 514 for a medical examination of atopic dermatitis as the image capturing control information.

In step S1801, the CPU 201 determines whether or not a symptom of a disease corresponding to the examination purpose selected by the operator in step S604, or the examination purpose uniquely identified in step S602 includes a rash. In a case where the symptom includes a rash, the processing proceeds to step S1802. In a case where the symptom does not include a rash, the processing proceeds to step S629.

In step S1802, the CPU 201 stores an evaluated field angle in the RAM 203.

The determination as to whether the evaluated field angle corresponds to a bird's-eye image or an enlarged image will be described below with reference to FIG. 20.

In step S1803, the CPU 201 determines whether or not both the bird's-eye image and the enlarged image have been captured. In a case where both of the images have been captured, the processing proceeds to step S629. In a case where both of the images have not been captured, the processing proceeds to step S1804.

In step S1804, the CPU 201 determines whether or not the bird's-eye image has been captured. In a case where the bird's-eye image has been captured, the processing proceeds to step S1805. In a case where the bird's-eye image has not been captured, the processing proceeds to step S1806.

In step S1805, to notify the operator that the enlarged image is to be captured next, the CPU 201 displays a message for prompting the operator to capture the enlarged image, on the display device 204. To execute image capturing, the processing returns to step S616.

In step S1806, to notify the operator that a bird's-eye image is to be captured next, the CPU 201 displays a message for prompting the operator to capture a bird's-eye image, on the display device 204. To execute image capturing, the processing returns to step S616.

Figure 19A:
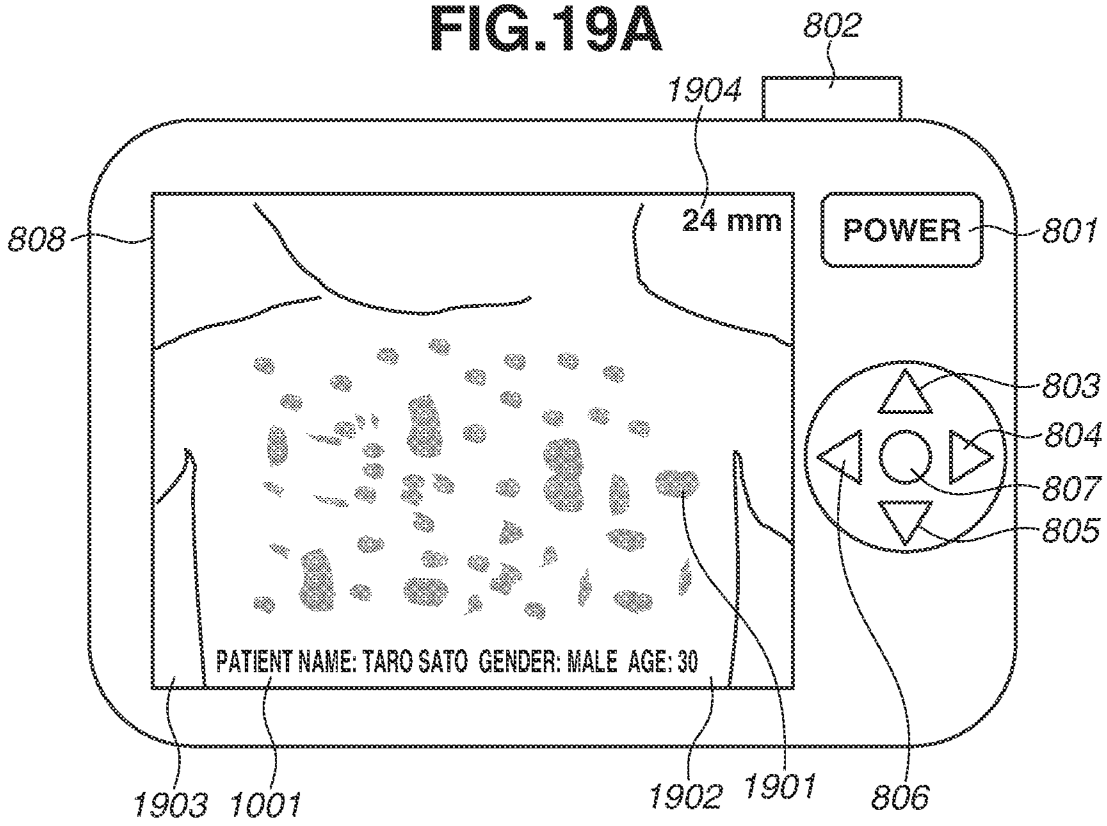
FIG. 19A is a diagram illustrating a state in which the digital still camera is viewed from the back side.
Figure 19B:
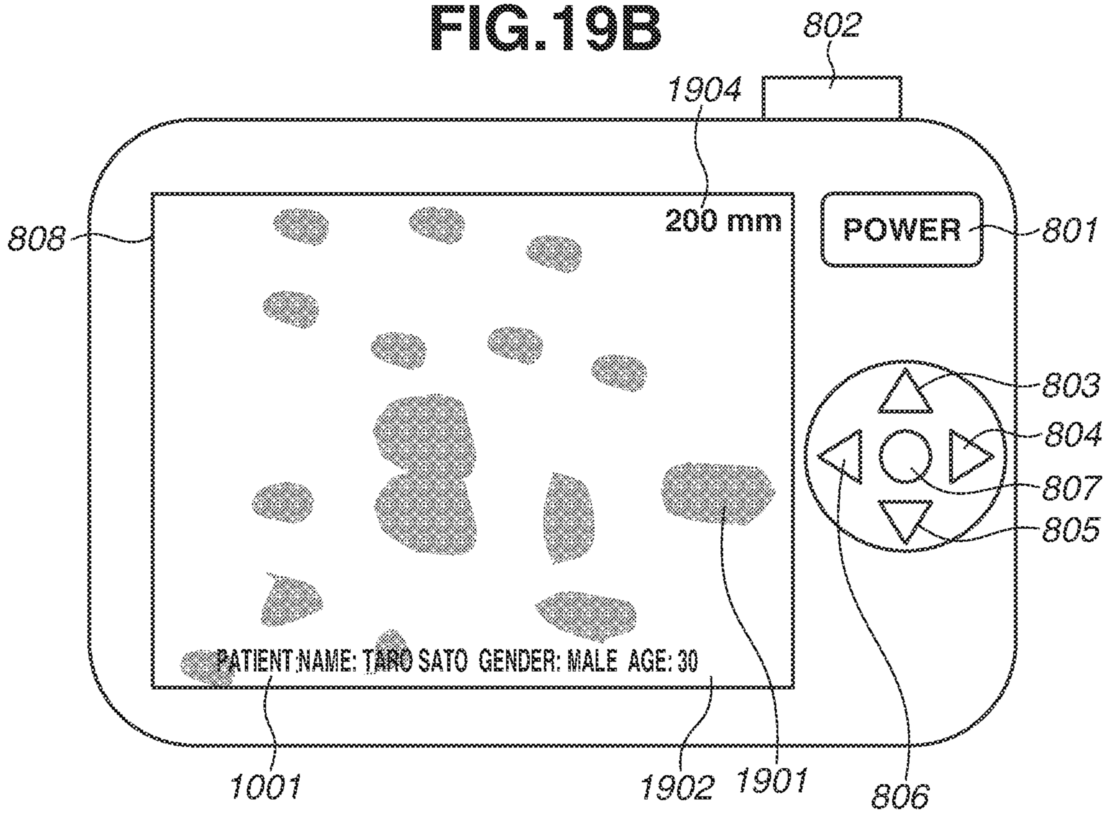
FIG. 19B is a diagram illustrating a state in which the digital still camera is viewed from the back side.

FIGS. 19A and 19B are diagrams each illustrating a state in which a digital still camera operating as an imaging apparatus according to an exemplary embodiment of the present invention is viewed from the back side. FIGS. 19A and 19B each illustrate an example of an affected part image in a case where the examination purpose is atopic dermatitis. Members fulfilling the same functions as those illustrated in FIGS. 8 and 10 are assigned the same numerals as those in FIGS. 8 and 10.

FIG. 19A illustrates an example of a bird's-eye image.

FIG. 19B illustrates an example of an enlarged image.

A portion 1901 indicates an affected part and indicates a rash portion in a case where the examination purpose is atopic dermatitis.

A portion 1902 indicates a healthy portion.

A portion 1903 indicates a background portion other than the affected part 1901 and the healthy portion 1902, and indicates a wall, for example.

A display 1904 indicates an example of field angle display, and indicates focal length information of a lens. The display 1904 needs not be displayed.

Figure 20:
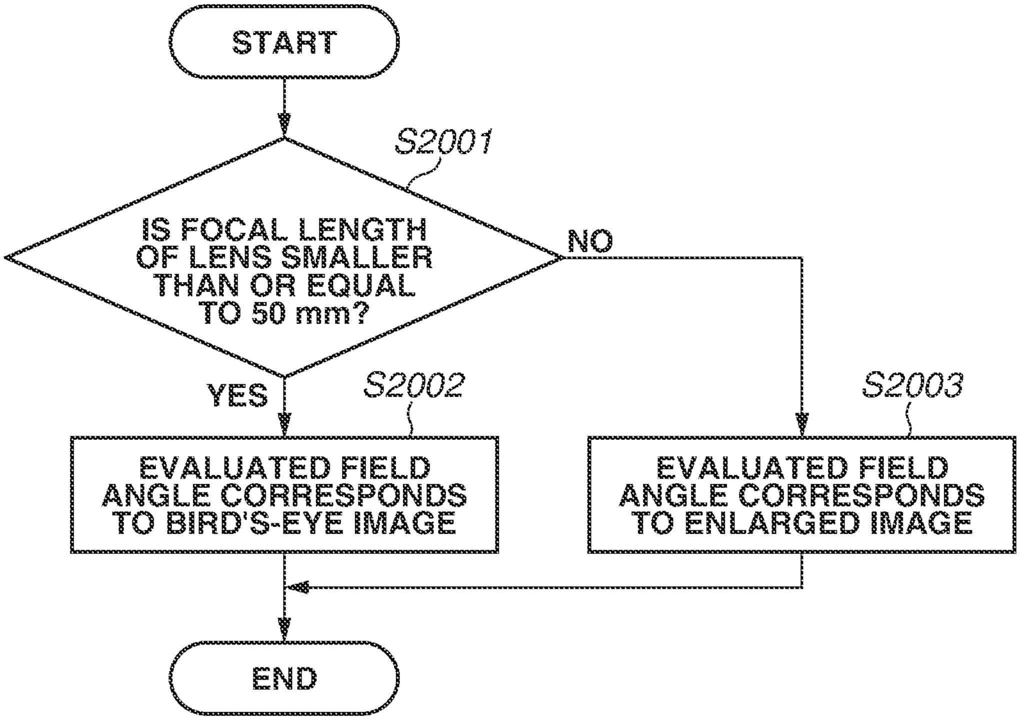
FIG. 20 is a flowchart illustrating determination processing of a bird's-eye image and an enlarged image.

FIG. 20 is a flowchart for determining whether an evaluated field angle corresponds to a bird's-eye image or an enlarged image according to the present exemplary embodiment. The processing is performed in step S1802.

In step S2001, the CPU 201 determines whether or not a focal length of the lens during the image capturing is smaller than or equal to 50 mm. In a case where a focal length of the lens is smaller than or equal to 50 mm, the processing proceeds to step S2002. In a case where a focal length of the lens is not smaller than or equal to 50 mm, the processing proceeds to step S2003.

In step S2002, the CPU 201 determines that the evaluated field angle corresponds to a bird's-eye image.

In step S2003, the CPU 201 determines that the evaluated field angle corresponds to an enlarged image.

In FIG. 20, a threshold value of the focal length of the lens is set to 50 mm, but any value other than 50 mm may be set, or a plurality of threshold values may be provided depending on a disease set as the examination purpose.

In addition, whether an evaluated field angle corresponds to a bird's-eye image or an enlarged image may be determined using a method other than the above-described method. For example, by performing image analysis based on color information or the like, in a case where the background portion 1903 exists, it may be determined that the evaluated field angle corresponds to a bird's-eye image, and in a case where the background portion 1903 does not exist, it may be determined that the evaluated field angle corresponds to an enlarged image. Furthermore, the operator may be prompted to select whether a captured image is a bird's-eye image or an enlarged image.

As described above, with the imaging apparatus of the present exemplary embodiment, in a case where the examination purpose is a disease with a symptom including a rash, the operator is prompted to capture a bird's-eye image and an enlarged image, and it is possible to prevent the operator from forgetting to capture an image.

As described above, with the imaging apparatus of the present exemplary embodiment, it can be confirmed whether an appropriate image has been captured depending on an examination purpose, and furthermore, the operator is notified of an issue in the image capturing. It accordingly becomes possible to record stable image data irrespective of the skill level of the operator.

Fourth Exemplary Embodiment

Figure 21:
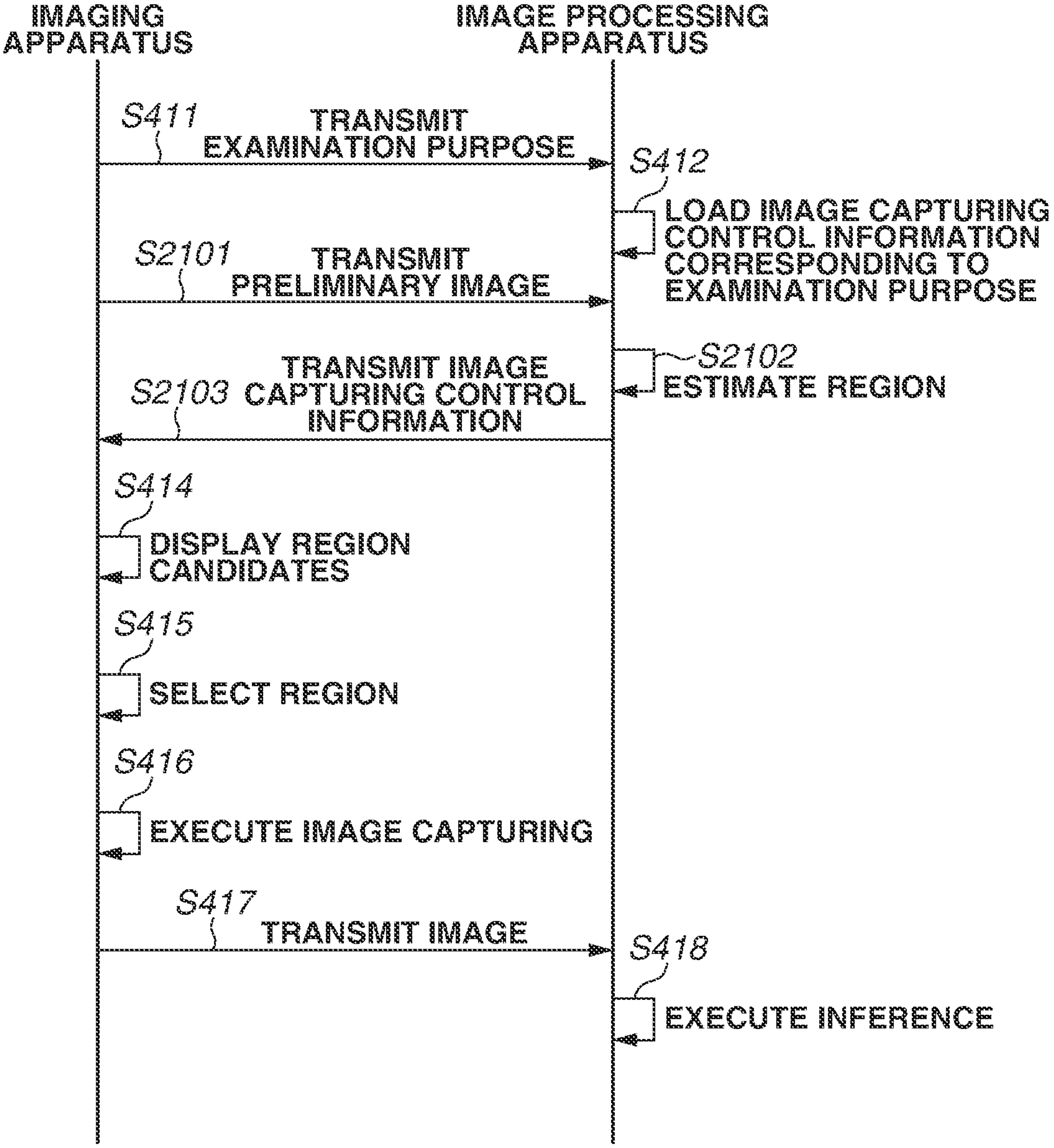
FIG. 21 is a sequence diagram illustrating processing of recording a disease state of a patient using the medical system.

In the present exemplary embodiment, referring to FIGS. 21 to 27, descriptions will be given of an example in which work of selecting a region is saved by making estimation based on a preliminary image of an imaging apparatus before image capturing, and furthermore, an image capturing condition is changed to be more desirable using a selection result. In the present exemplary embodiment, processing similar to that in the first exemplary embodiment is basically performed, and only a part of the processing is different from that in the first exemplary embodiment. In the present exemplary embodiment, the processing different from that in the first exemplary embodiment will be described with reference to FIG. 21. FIG. 21 is a diagram illustrating a flow of processing according to the present exemplary embodiment by extracting processing from examination purpose transmission in step S411 to inference execution in step S418 from the processing illustrated in FIG. 4. In the processing illustrated in FIG. 21, processes in steps S411 and S412 and processes in steps S414 to S418 are similar to processes illustrated in FIG. 4. Thus, the description will be omitted. Similarly to the processes illustrated in FIG. 4, the processes illustrated in FIG. 21 are implemented by the apparatuses and the systems executing the processes based on control programs of the apparatuses and the systems.

The imaging apparatus that has read the image capturing control information performs preliminary image transmission in step S2101. As a transmission timing of a preliminary image in this step, similarly to the operator capturing an affected part image, the imaging apparatus may capture a preliminary image upon the operator pressing a shutter button by himself or herself, and the imaging apparatus may transmit the preliminary image to the image processing apparatus. Alternatively, in a case where the imaging apparatus executes a live view function of displaying a live view image (live image) during an image capturing standby time before an affected part image is captured in step S416, an image captured for live view may be automatically transmitted to the image processing apparatus as the preliminary image.

Figure 22:
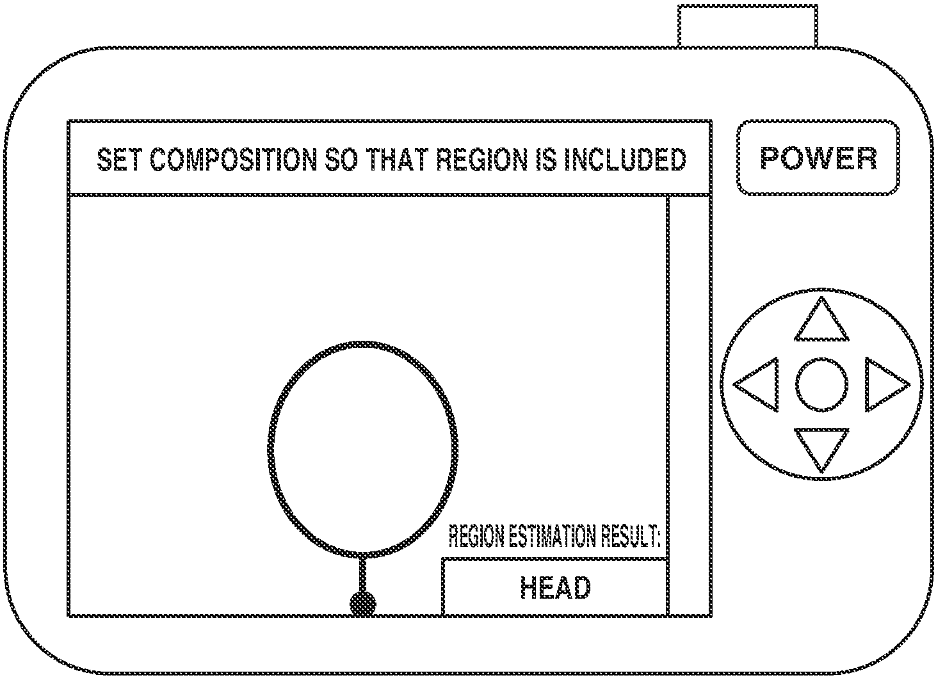
FIG. 22 is a diagram illustrating a state in which the digital still camera is viewed from the back side.

FIG. 22 illustrates an example of display on the imaging apparatus in a case where the preliminary image captured by the operator pressing a shutter button is transmitted, and FIGS. 23A to 23D each illustrate an example of display on the imaging apparatus in a case where the live view function is executed and a preliminary image is automatically transmitted during the image capturing standby time for an affected part image.

In step S2102, the image processing apparatus that has received the preliminary image in step S2101 performs region estimation. In the region estimation, a human body is extracted using luminance information, color information, hue information, gradient information, and the like of the preliminary image. After that, the region estimation is executed using the gradient information or a distribution of regional color or intensity information. Alternatively, the region estimation may be executed based on matching that uses shape feature information in a grayscale distribution or luminance gradient, or the region estimation may be executed by extracting pixels with luminance gradients of a fixed value or more as edge information, and using pixel positions, centroid, gradient, and the like. In addition, regions included in the received preliminary image may be estimated by creating supervised data of each region of the human body by machine learning that uses a neural network, such as deep learning. In addition, in the present exemplary embodiment, the region estimation is performed in the image processing apparatus, but the region estimation may be executed in the imaging apparatus. Then, in step S2103, the image processing apparatus transmits a region estimation result indicating region information estimated in the region estimation in step S2102, and the image capturing control information loaded in step S412, to the imaging apparatus. The image capturing control information and the region estimation result may be simultaneously transmitted to the imaging apparatus as illustrated in FIG. 21, or may be separately transmitted. For example, upon receiving the examination purpose in step S411, the image processing apparatus may transmit the image capturing control information corresponding to the examination purpose to the imaging apparatus. Then, upon receiving the preliminary image from the imaging apparatus in step S2101, the image processing apparatus may execute the region estimation in step S2102, and transmit the region estimation result to the imaging apparatus. In addition, the imaging apparatus may be enabled to transmit the preliminary image to the image processing apparatus before transmitting the examination purpose.

By the image processing apparatus performing the region estimation in step S2102, and the imaging apparatus acquiring the region estimation result in step S2103 (region acquisition), as illustrated in FIG. 22, a region estimated by the image processing apparatus can be displayed on the imaging apparatus together with the preliminary image. If a composition is a composition as illustrated in FIG. 22, “head” is estimated as the region, and “head” is displayed as an estimated region together with the preliminary image. In a case where a live view image is used as the preliminary image as in FIGS. 23A to 23D, in step S2101, the imaging apparatus transmits an image captured as the live view image to the image processing apparatus as the preliminary image at a predetermined interval. Then, in step S2102, the image processing apparatus executes the region estimation for each of the preliminary images received at the predetermined interval, and in step S2103, transmits region information of the estimated region to the imaging apparatus as the region estimation result. In other words, until a region is selected by the operator in steps S414 and S415, the processes in steps S2101 to S2103 are repeated, and the imaging apparatus displays a region estimated by the image processing apparatus together with a current live view image. Since the region displayed on the imaging apparatus is not a region in a current live image but a region estimated based on an image transmitted as a preliminary image, region display may sometimes be delayed to a certain degree. Then, if a live image changes with a change of a composition on the imaging apparatus, the region estimated in step S2102 also changes with the changed live image. For example, in FIGS. 23A to 23D, a region estimation result is displayed while being changed in such a manner that a total body is displayed in FIG. 23A, a lower back and an upper body is displayed in FIG. 23B, an upper body is displayed in FIG.

Figure 23A:
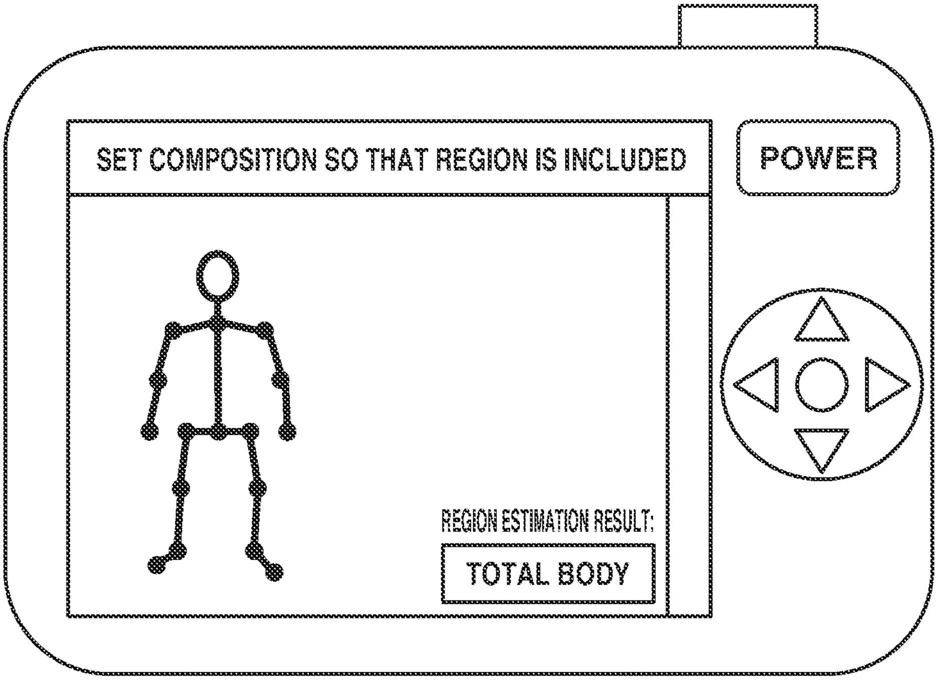
FIG. 23A is a diagram illustrating a state in which the digital still camera is viewed from the back side.
Figure 23B:
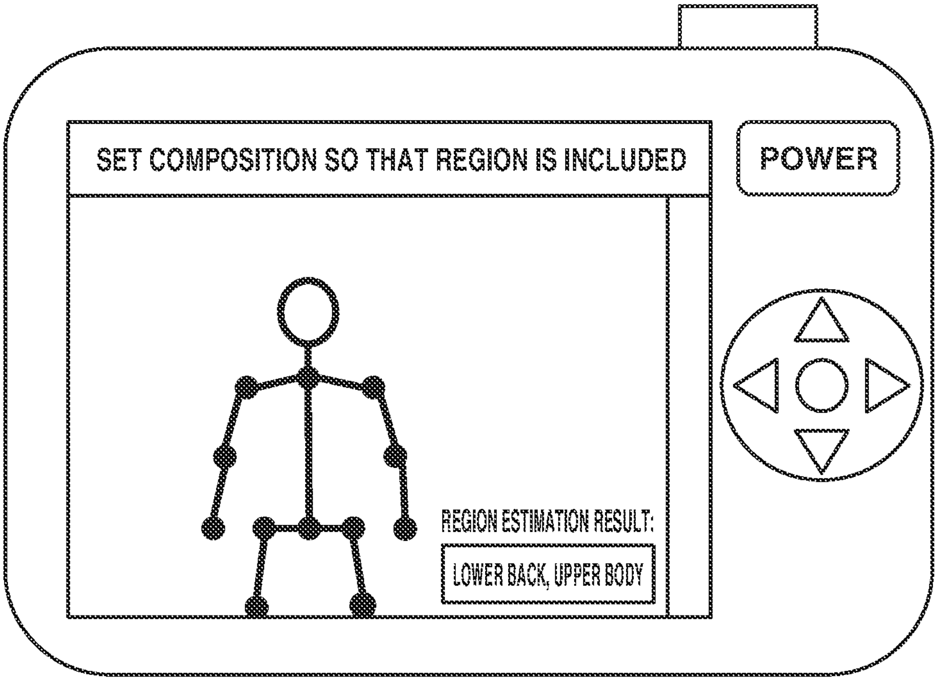
FIG. 23B is a diagram illustrating a state in which the digital still camera is viewed from the back side.
Figure 23C:
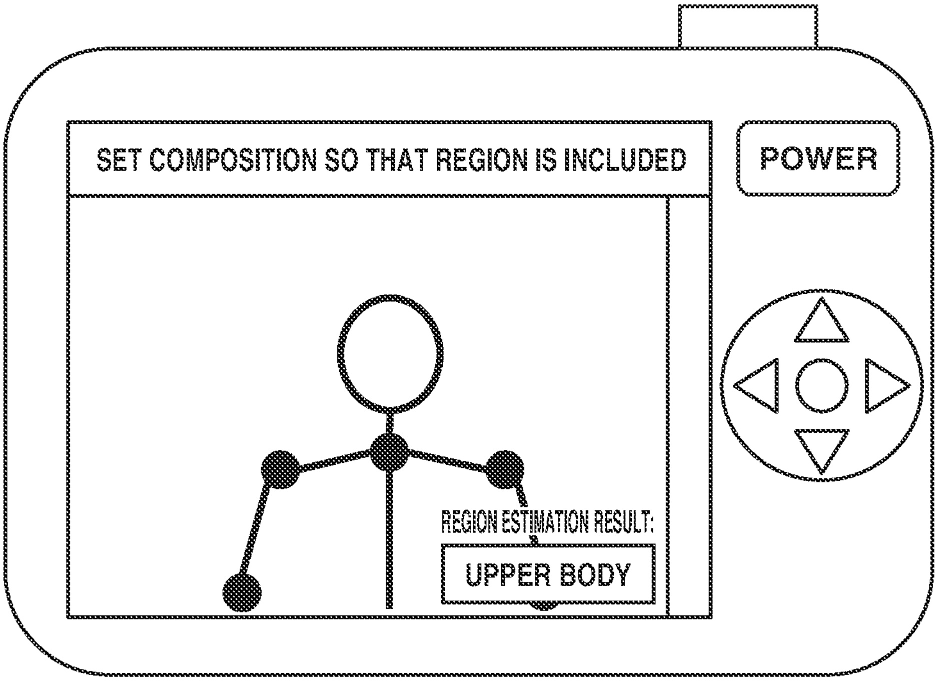
FIG. 23C is a diagram illustrating a state in which the digital still camera is viewed from the back side.
Figure 23D:
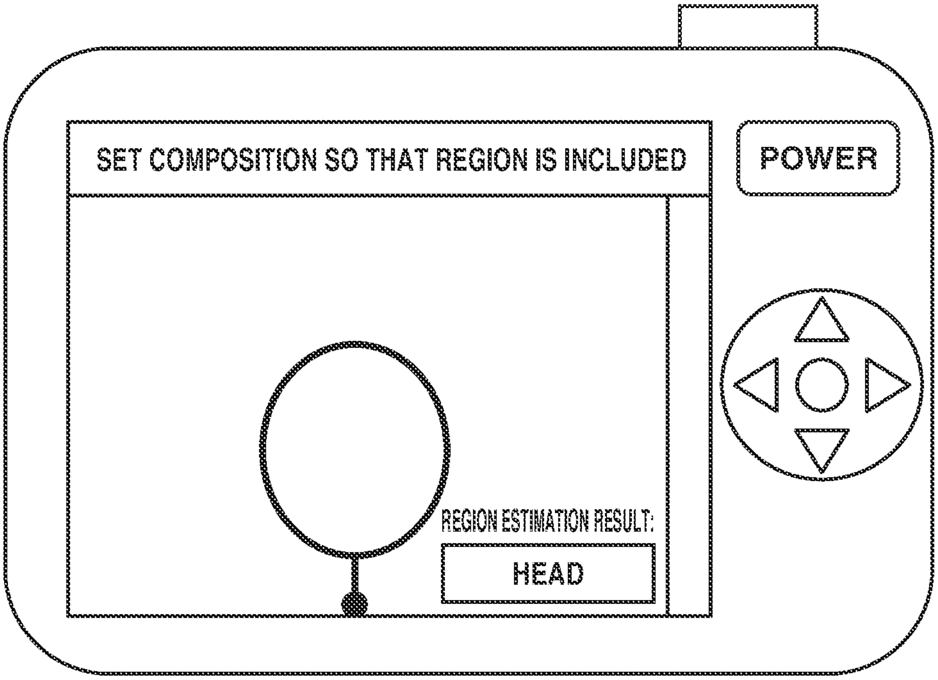
FIG. 23D is a diagram illustrating a state in which the digital still camera is viewed from the back side.
Figure 24:
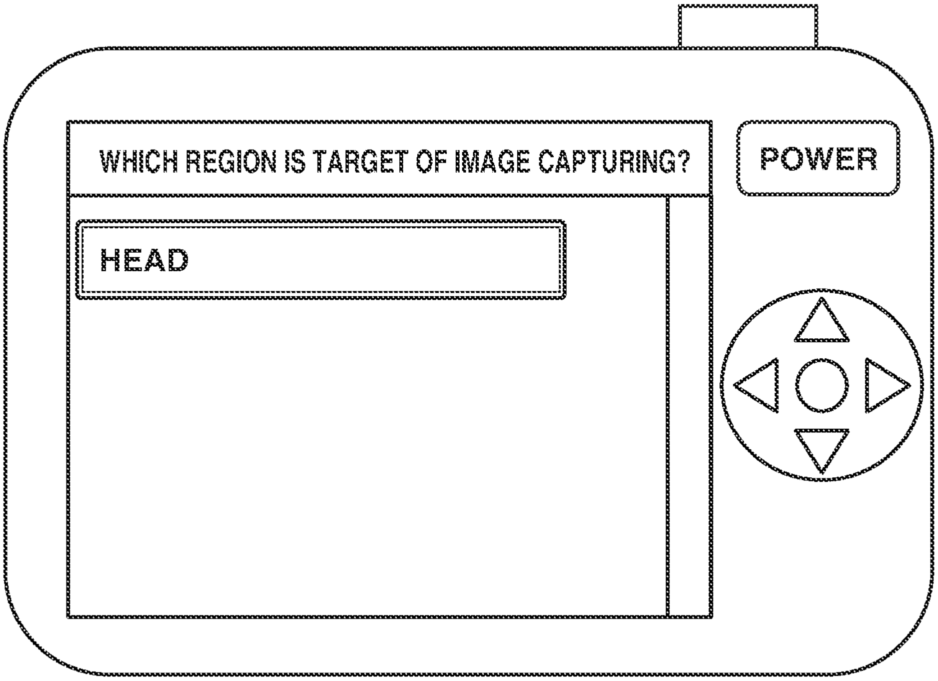
FIG. 24 is a diagram illustrating a state in which the digital still camera is viewed from the back side.

23C, and then, a head is displayed in FIG. 23D. In FIGS. 22 and 23A to 23D, an estimated region is displayed together with an image. Nevertheless, not only the estimated region but also the patient information received by the imaging apparatus in step S407 and the examination purpose selected in step S410 may be displayed.

When the region estimation is performed in step S2102, not only one region is regarded as the region estimation result but also a plurality of regions may be regarded as the estimation result. Depending on image data obtained by image capturing, it is considered that a region of a human body in a captured image is wide and an estimation result includes a plurality of regions. In this case, all of the plurality of estimated regions may be regarded as the region estimation result. In a case where the region estimation result includes the plurality of regions, the region estimation result may be generated by listing regions in descending order of certainty, or setting a flag to a region with high certainty, for example, in such a manner that a region with high estimation certainty is distinguishable, and the generated region estimation result may be transmitted to the imaging apparatus.

In addition, the region estimation may be performed using not only the preliminary image but also the examination purpose received in step S411, or the patient information received from the electronic medical chart system in step S404. For example, in a case where an image capturing target region in a medical history within one month for the examination purpose received in step S411 is "head", a head may be selected as an estimation result, or a past image capturing target region may be made easily-selectable in a case where a medical history exists. In a case where the image capturing target region in the case where a medical history exists and the estimation result obtained based on a preliminary image are different, both the image capturing target region in the medical history and a region indicated by the estimation result obtained based on a preliminary image may be transmitted to the imaging apparatus as a region estimation result.

In a case where a preliminary image is captured by the operator issuing an image capturing instruction of a preliminary image as illustrated in FIG. 22, after a region estimation result is received from the image processing apparatus in step S2103, a live view image is automatically transmitted as a preliminary image as illustrated in FIGS. 23A to 23D. In this case, upon receiving a region selection instruction from the operator, the imaging apparatus performs region candidate display in step S414.

Figure 25:
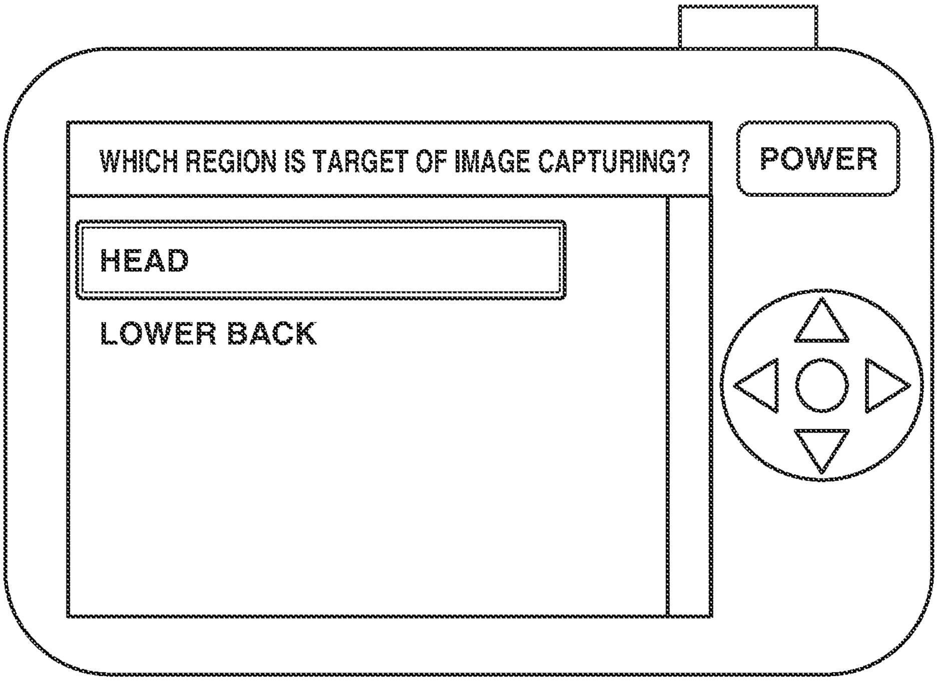
FIG. 25 is a diagram illustrating a state in which the digital still camera is viewed from the back side.

In step S414, similarly to the first exemplary embodiment, region candidates are displayed as in FIG. 25. In the present exemplary embodiment, the region estimation result received from the image processing apparatus in step S2103 is displayed as the region candidates. Similarly to the first exemplary embodiment, in a case where the number of regions in the region estimation result received in step S2103 is one, the region received as the region estimation result in step S2103 may be automatically selected and set as the image capturing target region by the imaging apparatus (the CPU 201) in step S415 without executing the display of the region candidates (region selection screen) in step S414. In addition, in a case where a region selection operation has been performed by the operator without a preliminary image being transmitted in step S2101, similarly to the first exemplary embodiment, the region candidates may be displayed without using a region estimation result. In addition, when the region candidates are displayed in step S414, or when the region indicated by the estimation result is displayed as illustrated in FIGS. 22 and 23A to 23D, a region corresponding to an examination purpose and a region not corresponding to the examination purpose may be displayed in a distinguishable manner. The region not corresponding to the examination purpose is displayed in a distinguishable manner so that the region can be identified as a region not included in the region candidates of the examination purpose selected in step S411. For example, in a case where a region included in the region estimation result received from the image processing apparatus in step S2103 is the region not included in the image capturing target region candidates of the examination purpose selected in step S411, the region may be displayed in a grayout state, or displayed in a different color or display mode. Alternatively, when the region estimation result is displayed together with an image as illustrated in FIGS. 22 and 23A to 23D, a region not corresponding to the examination purpose is displayed in a grayout state, and may be hidden in the display of the region candidates in step S414 since the region not corresponding to the examination purpose is unselectable. In addition, in a case where the region estimation result includes information regarding the certainty of estimation, in the display of the region estimation result in FIGS. 22 and 23A to 23D and the display of the region candidate in FIGS. 24 and 25 (region selection screen), a region with high estimation certainty and a region with low estimation certainty may be displayed in a distinguishable manner. For example, the region with high estimation certainty may be displayed by boldface or in a different color.

In this manner, by transmitting the preliminary image for region estimation to the image processing apparatus before the region selection (steps S414 and S415), and regarding only a region estimated by the image processing apparatus as the region candidate, the region selection can be simplified. By automatically transmitting the preliminary image using a live view image, the operator can narrow down the region candidates to the region indicated by the estimation result, without performing an extra operation. Furthermore, in the case where the number of regions in the region estimation result is one, in step S415, the imaging apparatus may automatically select the region in the estimation result, without performing the display of the region candidates in step S414. With this configuration, region selection by the operator becomes unnecessary. In addition, by displaying the region in the estimation result together with the image, the operator can confirm the estimated region. In a case where the region in the estimation result is different from the image capturing target region, the operator can change the composition so that the region in the estimation result is changed. In a case where the image capturing target region and the region in the estimation result are different, the composition may be an inappropriate composition. Thus, the operator can check whether image capturing has been executed with an appropriate composition.

It is also considered that the region estimation is used only for recording or transmitting the region information, obtained as a region estimation result, in association with the affected part image captured in step S416 without being used for selection of the region information or confirmation of the composition. In this case, without transmitting a preliminary image, the region estimation may be performed using the affected part image captured in step S416 and transmitted to the image processing apparatus in step S417.

In a case where a more suitable affected part image is desired to be captured, since a size, a depth change amount, an appropriate composition, and the like vary depending on a region of which an image is to be captured, an image capturing condition and a confirmation condition vary in some cases.

In view of the foregoing, a modified example of the fourth exemplary embodiment will be described with reference to FIGS. 26 and 27.

Figure 27:
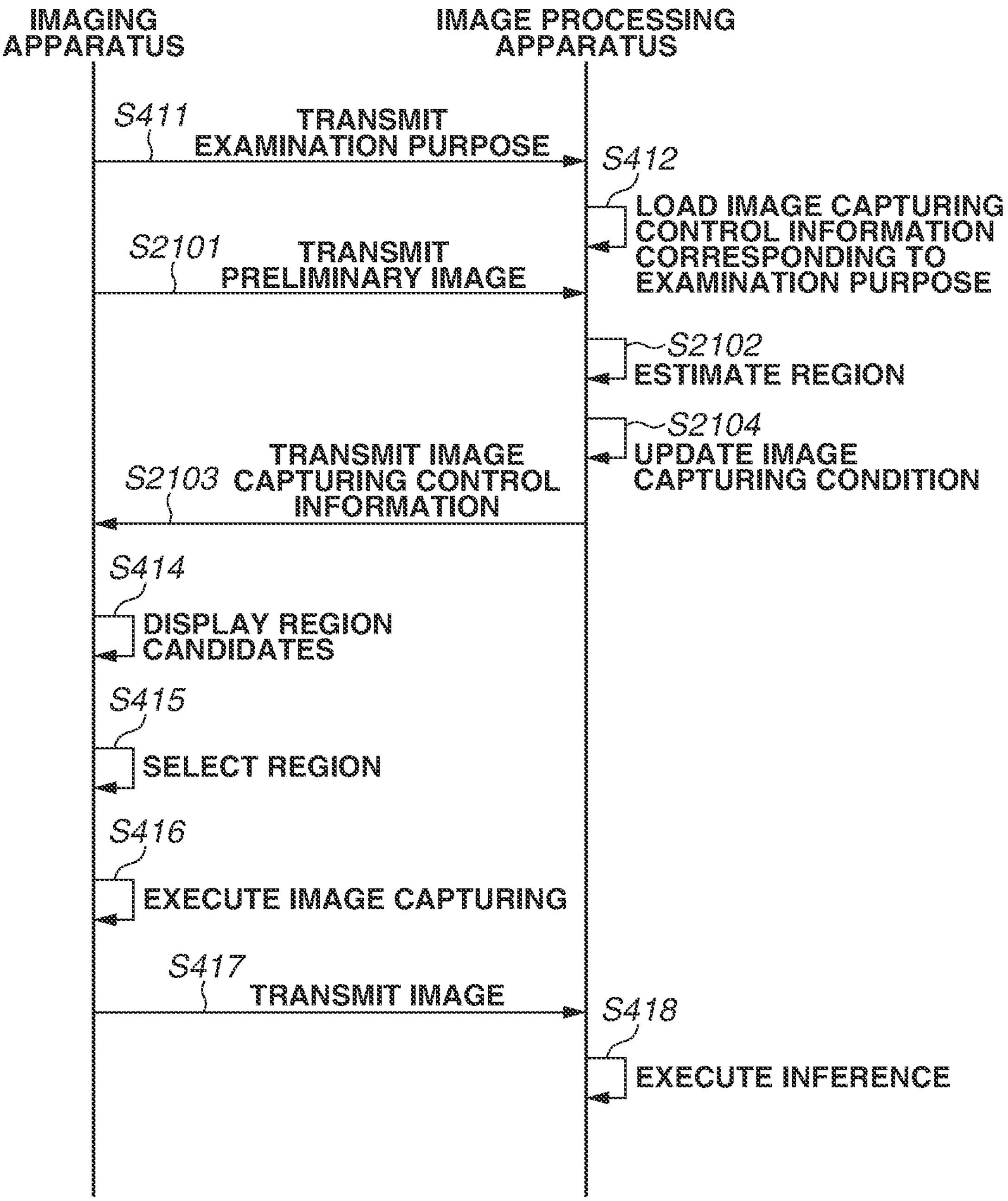
FIG. 27 is a sequence diagram illustrating processing of recording a disease state of a patient using the medical system.

In FIG. 27, image capturing condition update processing in step S2104 is added to the above-described flow illustrated in FIG. 21. In the image capturing condition update processing in step S2104, the image processing apparatus updates an image capturing condition to be transmitted to the image capturing apparatus in accordance with the region estimation result obtained in step S2102, in such a manner that the image capturing condition becomes an image capturing condition suitable for the estimated region. Then, in step S2103, the image processing apparatus transmits image capturing control information updated in step S2104, and the region estimation result obtained in step S2102. Such image capturing condition update may be executed in accordance with a region selection result in step S415, in addition to being performed in accordance with the region estimation result in step S2102. In this case, the region selected in step S415 is notified (transmitted) to the image processing apparatus, the image processing apparatus updates image capturing condition information and transmits the updated image capturing condition information to the imaging apparatus, and the imaging apparatus sets an image capturing condition of the imaging apparatus based on the received image capturing condition information. Alternatively, image capturing condition information corresponding to a plurality of region candidates corresponding to the examination purpose may be preliminarily transmitted from the image processing apparatus to the imaging apparatus, and in response to a region being selected on the imaging apparatus, an image capturing condition of the imaging apparatus may be set based on image capturing condition information corresponding to the selected region.

FIG. 26 illustrates an example of an image capturing condition and a confirmation condition of each region candidate in a case where the examination purpose is pressure sore. For example, because a head, hands, and arms are not so large in size, a subject distance needs not be so far. In a case where the subject distance is close, focus can be achieved even if an aperture is opened. Thus, a setting for reducing noise and subject blurring is made in such a manner that an aperture is opened, an ISO sensitivity is low, and a shutter speed is high. On the other hand, a back, a lower back, and leg portions have large sizes and large depth change amounts. It is therefore necessary to ensure a large subject distance and a large depth of field. Thus, an ISO value is set to a high value and a shutter speed is set to a low speed to increase brightness of a captured image.

The description has been provided of the example of updating an image capturing condition based on the examination purpose and the region estimation result, but furthermore, adjustment may be further performed based on characteristics of a patient to be the subject. For example, in a case where a skin color of a patient is a dark color and an image of an affected part of a skin disease is to be captured, an ISO sensitivity is increased within a recommended range. In a case where the patient is an infant, the region is a limb, and subject blurring is expected, a shutter speed is increased within a recommended range.

Other Exemplary Embodiment

Heretofore, the present invention has been described in detail based on the desirable exemplary embodiments, but the present invention is not limited to these specific exemplary embodiments. Various configuration not departing from the gist of the invention are also included in the present invention. The above-described exemplary embodiments may be partially combined as appropriate.

In addition, the present invention can also be implemented by processing of supplying a program for implementing one or more functions of the above-described exemplary embodiments to a system or an apparatus via a network or a storage medium, and one or more processors in a computer of the system or the apparatus reading and executing the program. In addition, the present invention can also be implemented by a circuit (for example, an application specific integrated circuit (ASIC)) for implementing the one or more functions. Accordingly, a program code to be supplied to and installed in a computer to implement the functional processing of the present invention on the computer also embodies the present invention. In other words, a computer program for implementing the functional processing of the present invention is also included in the present invention.

The present invention is not limited to the above-described exemplary embodiments, and various changes and modifications can be made without departing from the spirit and the scope of the present invention. Thus, the following claims are appended to publicize the scope of the present invention.

According to the present invention, it is possible to provide an imaging apparatus that can acquire information suitable for an examination purpose.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An imaging apparatus including an imaging sensor configured to capture an image for an examination, and a network interface configured to communicate with a predetermined system, the imaging apparatus comprising:
at least one processor; and
at least one memory storing instructions which, when the instructions are executed by the at least one processor, cause the imaging apparatus to:
select an examination purpose;
acquire image capturing control information corresponding to the examination purpose selected from the predetermined system via the network interface; and
set at least one of a setting value of an image capturing condition, display content to be displayed on a display unit together with an image to be captured by the imaging unitsensor, and an item of information to be associated with an image captured by the imaging unit sensor based on the image capturing control information acquired in accordance with the examination purpose,
wherein, based on the image capturing control information acquired in accordance with the examination purpose, the examination evaluation item is set from among a plurality of examination evaluation items including at least one of DESIGN-R, a specified symptom sum score system with grading of scaling, roughness, redness and cracks (SRRC), an Eczema Area and Severity Index (EASI), a Psoriasis Area Severity Index (PASI), and a Total Body Surface Area (TBSA),
wherein, in a case where the examination purpose is pressure sore, the DESIGN-R is set as the examination evaluation item,
wherein, in a case where the examination purpose is asteatosis cutis, the SRRC is set as the examination evaluation item,
wherein, in a case where the examination purpose is atopic dermatitis, the EASI is set as the examination evaluation item,
wherein, in a case where the examination purpose is psora, the PASI is set as the examination evaluation item, and
wherein, in a case where the examination purpose is burn injury, the TBSA and a burn depth is set as the examination evaluation item.

2. The imaging apparatus according to claim 1, wherein the imaging apparatus is a portable imaging apparatus.

3. The imaging apparatus according to claim 1,
wherein the setting value of the image capturing condition is set based on the image capturing control information acquired in accordance with the examination purpose, and
wherein the image capturing condition includes at least one of a focus position, a zoom position, an ISO sensitivity, an exposure, a shutter speed, an aperture, white balance, color adjustment, and electronic flash on/off.

4. The imaging apparatus according to claim 1, wherein an examination evaluation item is set to be associated with an image captured by the imaging sensor based on the image capturing control information acquired in accordance with the examination purpose.

5. The imaging apparatus according to claim 1, wherein the image capturing control information includes the setting value of the image capturing condition, and further includes at least one of region information regarding a candidate of a region to be image-captured, information regarding an evaluation item, and information regarding a region required to be image-captured.

6. The imaging apparatus according to claim 1, wherein a setting value of an image capturing condition is set based on the image capturing control information acquired in accordance with the examination purpose unmodifiable in accordance with a user operation, and makes a setting value of an image capturing condition not set based on the image capturing control information modifiable in accordance with a user operation.

7. The imaging apparatus according to claim 1,
wherein the image capturing control information includes information regarding a region required to be image-captured,
wherein, in a case where the examination purpose is any of asteatosis cutis, atopic dermatitis, psora, burn injury, and hives, information indicating a head/neck, a body trunk, an upper extremity, and a lower extremity as regions required to be image-captured is included in the image capturing control information, and
wherein, in a case where the examination purpose is a disease in an oral cavity, information indicating an upper jaw and a lower jaw as regions required to be image-captured is included in the image capturing control information.

8. A control method of an imaging apparatus including an imaging sensor configured to capture an image for an examination, and a network interface configured to communicate with a predetermined system, the control method comprising:
selecting an examination purpose;
acquiring image capturing control information corresponding to the selected examination purpose from the predetermined system via the network interface; and
setting at least one of a setting value of an image capturing condition, display content to be displayed on a display unit together with an image to be captured by the imaging sensor, and an item of information to be associated with the image captured by the imaging sensor based on the image capturing control information acquired in accordance with the examination purpose,
wherein, based on the image capturing control information acquired in accordance with the examination purpose, the examination evaluation item is set from among a plurality of examination evaluation items including at least one of DESIGN-R, a specified symptom sum score system with grading of scaling, roughness, redness and cracks (SRRC), an Eczema Area and Severity Index (EASI), a Psoriasis Area Severity Index (PASI), and a Total Body Surface Area (TBSA),
wherein, in a case where the examination purpose is pressure sore, the DESIGN-R is set as the examination evaluation item,
wherein, in a case where the examination purpose is asteatosis cutis, the SRRC is set as the examination evaluation item,
wherein, in a case where the examination purpose is atopic dermatitis, the EASI is set as the examination evaluation item,
wherein, in a case where the examination purpose is psora, the PASI is set as the examination evaluation item, and wherein, in a case where the examination purpose is burn injury, the TBSA and a burn depth is set as the examination evaluation item.

9. The imaging apparatus according to claim 1, wherein, based on the image capturing control information received in accordance with the examination purpose, a type of an image capturing assisting graphic is determined to be displayed together with an image to be captured by the imaging sensor, and performs control to display the determined image capturing assisting graphic on a display section of the imaging apparatus.

10. The imaging apparatus according to claim 9, wherein the type of the image capturing assisting graphic includes at least one of a graphic indicating an affected part in a last examination, a graphic indicating an outline of a region to be examined, a straight line for teeth bite position, and an outline of a dental arch.

11. The imaging apparatus according to claim 1, wherein the examination purpose is selected in accordance with a user operation from among a plurality of examination purposes acquired from the predetermined system via the network interface.

12. The imaging apparatus according to claim 11, wherein, in a case where a number of examination purposes acquired from the system is one, the examination purpose is automatically selected.

13. The imaging apparatus according to claim 1, wherein an image captured by the imaging sensor is transmitted to the predetermined system via the network interface, and receive an image analysis result of the image in the predetermined system from the predetermined system via the network interface, wherein information that is based on the image analysis result received is displayed together with the image.

14. The imaging apparatus according to claim 13, wherein control is performed in such a manner that:

in a case where the examination purpose is pressure sore, at least any of an area of an affected part, a pressure sore portion, a necrotic portion, an inflamed/infected portion, a granulation tissue portion, and depth information is displayed;

in a case where the examination purpose is asteatosis cutis, at least any of an area of an affected part, an asteatosis cutis portion, skin roughness, skin redness, a skin cracks and fissures portion is displayed;

in a case where the examination purpose is atopic dermatitis, at least any of an area of an affected part, an erythematous portion, an erosion/papular portion, a scratched portion, and a lichenified portion is displayed;

in a case where the examination purpose is psora, at least any of an area of an affected part, an erythematous portion, an erosion portion, and a desquamated portion is displayed;

in a case where the examination purpose is burn injury, at least any of an area of an affected part, a burn portion, and a burn depth is displayed;

in a case where the examination purpose is hives, at least any of an area of an affected part, a wheal portion, and a number of hives is displayed; and in a case where the examination purpose is a disease in an oral cavity, at least any of a type of tooth, presence or absence of a tooth, presence or absence of a prosthetic appliance, presence or absence of a decayed tooth, a decayed portion, and a periodontal disease portion is displayed.

15. The imaging apparatus according to claim 1, wherein a patient image captured by the imaging sensor is transmitted to the predetermined system via the network interface, and receive and acquire patient information corresponding to a patient of the patient image from the predetermined system via the network interface.

16. The imaging apparatus according to claim 15, wherein a captured image of a code related to a patient is transmitted to the predetermined system as the patient image, and receives, from the predetermined system, patient information corresponding to a code obtained by the predetermined system analyzing the patient image.

17. The imaging apparatus according to claim 15, wherein an examination purpose is selected from among examination purposes corresponding to the patient information.

18. The imaging apparatus according to claim 17, wherein, in a case where an examination purpose corresponding to the patient information does not exist, an examination purpose is selected from among a plurality of examination purposes not related to the patient information.

19. The imaging apparatus according to claim 1, wherein, in a case where a symptom of a disease to be the examination purpose includes a rash, the imaging unit is controlled to capture images at a plurality of different field angles.

20. The imaging apparatus according to claim 19, wherein, in the case where the symptom of the disease to be the examination purpose includes a rash, if the images at the plurality of different field angles have not been captured, capturing of an image is prompted at a field angle at which image capturing has not been executed.

21. The imaging apparatus according to claim 19, wherein, in the case where the symptom of the disease to be the examination purpose includes a rash, control to capture a bird's-eye image and an enlarged image.

22. The imaging apparatus according to claim 21, wherein whether or not the bird's-eye image and the enlarged image have been captured is determined based on focal length information of a lens of a captured image.

23. The imaging apparatus according to claim 1, wherein an image capturing target region is selected, wherein a region estimated based on an image captured by the imaging sensor is selected as an image capturing target region.

24. The imaging apparatus according to claim 23, wherein the region estimated based on an image captured by the imaging sensor is acquired, wherein an image captured by the imaging sensor is transmitted during an image capturing standby time to the predetermined system, and acquires a region estimated based on the image from the predetermined system.

25. The imaging apparatus according to claim 23, wherein a user to selectselects a region via a region selection screen from among a plurality of regions acquired.

26. The imaging apparatus according to claim 23, wherein a region estimated based on an image captured by the imaging sensor is selected during an image capturing standby time as an image capturing target region, and wherein control to display the selected region on the display is performed together with a live image captured by the imaging sensor.

27. The imaging apparatus according to claim 23, wherein a region estimated based on an image captured by the imaging sensor is selected during an image capturing standby time as the image capturing target region, and wherein an affected part image captured by the imaging sensor is transmitted in accordance with an image capturing instruction from a user and information regarding a region selected to the predetermined system in association with each other.

28. The imaging apparatus according to claim 27, wherein a setting value of an image capturing condition is set based on the image capturing control information acquired in accordance with the examination purpose, and a region selected.

29. The imaging apparatus according to claim 1, wherein an image capturing target region is selected based on region information included in the image capturing control information.

30. The imaging apparatus according to claim 29, wherein the image capturing target region is selected from among region candidates determined based on the image capturing control information.

31. The imaging apparatus according to claim 30, wherein a granularity of the region candidates made selectable is changed depending on whether or not a disease to be the examination purpose is to be evaluated based on a total body of a patient.

32. The imaging apparatus according to claim 31, wherein, in a case where the disease to be the examination purpose is to be evaluated based on the total body of a patient, a region indicating a wide range of a body is set as the region candidate, and wherein, in a case where the disease to be the examination purpose is not to be evaluated based on the total body of a patient, a region indicating a narrow range of the body is set as the region candidate.

33. The imaging apparatus according to claim 30, wherein control to display a region selection screen is performed for selecting the image capturing target region from among the region candidates on the display.

34. The imaging apparatus according to claim 33, wherein, based on information regarding a region required to be image-captured that is included in the image capturing control information, control to display the region selection screen is performed in such a manner that a candidate of the region required to be image-captured is distinguishable.

35. The imaging apparatus according to claim 30, wherein a granularity of the region candidates is changed depending on whether or not a disease to be the examination purpose includes a rash.

36. The imaging apparatus according to claim 35, wherein the disease including a rash is any of asteatosis cutis, atopic dermatitis, psora, and hives.

37. A non-transitory computer-readable storage medium storing a program for causing a computer to unitexecute a control method according to claim 8.

* * * * *